United States Patent
Ye et al.

(10) Patent No.: US 9,410,188 B2
(45) Date of Patent: Aug. 9, 2016

(54) METHOD AND KIT FOR DISCRIMINATING BETWEEN BREAST CANCER AND BENIGN BREAST DISEASE

(75) Inventors: Xun Ye, Shanghai (CN); Fei Wu, Shanghai (CN); Qinghua Xu, Hangzhou (CN); Xia Meng, Shanghai (CN); Bruno Mougin, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 0 days.

(21) Appl. No.: 13/696,937

(22) PCT Filed: May 28, 2010

(86) PCT No.: PCT/CN2010/073342
§ 371 (c)(1),
(2), (4) Date: Nov. 28, 2012

(87) PCT Pub. No.: WO2011/147096
PCT Pub. Date: Dec. 1, 2011

(65) Prior Publication Data
US 2013/0072399 A1    Mar. 21, 2013

(51) Int. Cl.
*C12Q 1/68* (2006.01)
(52) U.S. Cl.
CPC ............ *C12Q 1/6837* (2013.01); *C12Q 1/6886* (2013.01); *C12Q 2600/112* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 7,171,311 B2 * | 1/2007 | Dai et al. .................. | 702/19 |
| 7,842,467 B1 * | 11/2010 | Heidbrink et al. ............. | 435/7.1 |
| 2007/0015148 A1 | 1/2007 | Orr et al. | |
| 2007/0224201 A1 | 9/2007 | Wu et al. | |
| 2009/0123924 A1 * | 5/2009 | Krause et al. .................... | 435/6 |
| 2010/0003189 A1 | 1/2010 | Tlsty et al. | |
| 2010/0209928 A1 * | 8/2010 | Mirza et al. .................. | 435/6 |
| 2011/0217297 A1 * | 9/2011 | Kao et al. ................... | 424/133.1 |

FOREIGN PATENT DOCUMENTS

| | | |
|---|---|---|
| CN | 101354393 A | 1/2009 |
| WO | 2007067813 A2 | 6/2007 |
| WO | 2009039023 A2 | 3/2009 |

OTHER PUBLICATIONS

Tamimi et al., Cancer, Nov. 1, 2010, pp. 4944-4953.*
Hartmann et al., New England Journal of Medicine, Jul. 21, 2005, 353(3), pp. 229-237.*
Brenton et al., Journal of Clinical Oncology, Oct. 10, 2005, 23(29), pp. 7350-7360.*
André et al., Lancet Oncol, 2009, 10, pp. 381-390.*
GeneChip Human Genome U133 Arrays Data Sheet ( Affymetrix, 2003-2007, pp. 1-8.*
Arce et al., "Molecular and Genomic Characterization of Human DLEC, a Novel Member of the C-type Lectin Receptor Gene Family Preferentially Expressed on Monocyte-Derived Dendritic Cells," Eur. J. Immunol., vol. 31, pp. 2733-2740, 2001.
Bourgon, "Diagnostic Plots for Independent Filtering," pp. 1-5, Oct. 25, 2009.
Drucker et al., "Support Vector Regression Machines," Advances in Neural Information Processing Systems, pp. 155-161, 1996.
Haram et al., "Gene Expression Profile of Mouse Prostate Tumors Reveals Dysregulations in Major Biological Processes and Identifies Potential Murine Targets for Preclinical Development of Human Prostate Cancer Therapy," The Prostate, vol. 68, pp. 1517-1530, 2008.
Qin et al., "Increased Expression of the Inflammatory Protein YK:-40 in Precancers of the Breast," Int. J. Cancer, vol. 121, pp. 1536-1542, 2007.
Roslind et al., "YKL-40 Expression in Benign and Malignant Lesions of the Breast: A Methodologic Study," Appl Immunohistochem Mol Morphol, vol. 15, No. 4, pp. 371-381, Dec. 2007.
Whitney et al., "Individuality and Variation in Gene Expression Patterns in Human Blood," PNAS, vol. 100, No. 4, pp. 1896-1901, Feb. 18, 2003.
Wisniewski et al., "Distribution of LILRA3 (ILT6/LIR4) Deletion in Psoriatic Patients and Healthy Controls," Human Immunology, vol. 64, pp. 458-461, 2003.
Yang et al., "Using Peripheral Blood mRNA Signature to Distinguish Between Breast Cancer and Benign Breast Disease in Non-Conclusive Mamaography Patients," Cancer Biology & Therapy, vol. 10, No. 12, pp. 1235-1239, Dec. 15, 2010.
Mar. 10, 2011 International Search Report issued in International Application No. PCT/CN2010/073342.
Mar. 10, 2011 Written Opinion issued in International Application No. PCT/CN2010/073342.
Wilson et al., "QC and Affymetrix Data," Paterson Institute for Cancer Research, pp. 1-14, 2009.

* cited by examiner

Primary Examiner — Juliet Switzer
(74) Attorney, Agent, or Firm — Oliff PLC

(57) ABSTRACT

A method and kit are related to discriminating between breast cancer and benign breast disease by the determination of the expression level of at least one target gene including a nucleic acid sequence selected from the nucleic acid sequences set forth in SEQ ID NOs: 1, 2 or 3, 4 and 5 or 6 to obtain an expression profile for the patient, and the comparison of the expression profile of the patient with expression profiles of target genes from patients previously clinically classified as breast cancer and expression profiles of target genes from patients previously clinically classified as benign breast disease.

13 Claims, No Drawings

METHOD AND KIT FOR DISCRIMINATING BETWEEN BREAST CANCER AND BENIGN BREAST DISEASE

FIELD OF THE INVENTION

The present invention relates to the field of the discrimination between breast cancer and benign breast disease. Particularly, the present invention relates to a method and kit for discriminating between breast cancer and benign breast disease.

BACKGROUND

Breast cancer is the most common cancer in women in the world. As the pathogenesis of breast cancer is inadequately understood, the early diagnosis seemed much of significance. Currently, mammogram screening is the most frequent method for the breast cancer detection. It can be used to reduce breast cancer morbidity by 20 to 40 percent in the age of 40 to 69 women, which has been proved by several large randomized trials. Mammography is currently the gold standard for early breast cancer detection while the reported overall sensitivity is significantly reduced in certain subsets of women, particularly in women with radiographically dense breasts and those at increased risk of breast cancer. Estimates of film mammographic sensitivity in women with extremely dense breasts range from 48 to 63%. Mammography has the disadvantage of low sensitivity and specificity, especially in the young group, and a compression pain during the process. In addition, due to small volume and high-density breast, many cases failed to obtain a clear result of their mammography in the screening, which are often classified as BI-RADS 0 (BI-RADS: Breast Imaging Reporting and Data System) in their mammographic diagnosis.

The BI-RADS was developed in 1993 by the American College of Radiology (ACR) to standardize mammographic reporting, to improve communication, to reduce confusion regarding mammographic findings, to aid research, and to facilitate outcomes monitoring. According to the Mammography Quality Standards Act (MQSA) of 1997 [Final Rule 62(208):55988], all mammograms in the United States must be reported using one of these assessment categories. Each mammographic study should be assigned a single assessment based on the most concerning findings. Classifications are divided into an incomplete assessment (category 0) and completed assessments (categories 1, 2, 3, 4, 5, 6). BI-RADS Category 0 is defined as an incomplete assessment, which means additional imaging needed. Follow-up is usually recommended, which requires a long, expensive and anxiety producing process, based on ultrasonography or magnetic resonance imaging (MRI) or even biopsy. Ultrasonography, even combined with mammography, is associated with high rate of false positive results which led to unnecessary invasive steps. The long term of reservation of MRI is detrimental to the patients. MRI also brings a high rate of false positive result, together with a high cost. With such a variety of factors, the need of a new easy-to go test that would improve breast cancer detection and demonstrate the risk of patients, particularly when mammography cannot be identified, is highly important.

The serum biomarker, such as CEA, CA15-3, does not show a good performance in the cancer screening [1]. Recently, there is some literature describe the possibility of early diagnosis of breast cancer using gene-expression patterns in peripheral blood cells [2]. The result of these pilot studies indicate that cancer would cause characteristic changes in the biochemical environment of blood, and as a result of that the expression pattern of some identified genes can be used to discriminate cancer and control group with high accuracy. However, no alternative based on blood biomarkers has yet succeeded to discriminate within the BI-RADS 0 patients, between breast cancer (BC) and benign breast disease (BBD).

SUMMARY OF THE INVENTION

The present invention provides a method for discriminating between breast cancer and benign breast disease in a biological sample from a patient, wherein it comprises the following steps: a) obtaining the biological sample comprising a biological material from the patient, b) contacting the biological material from the biological sample with at least one specific reagent for at least one target gene and no more than 28 specific reagents for 28 target genes comprising the nucleic acid sequences set forth in SEQ ID NOs 1 to 44, wherein the at least one reagent is specific for at least a target gene comprising a nucleic acid sequence selected from the nucleic acid sequences set forth in SEQ ID NOs: 1, 2 or 3, 4 and 5 or 6, and c) determining the expression level of at least one target gene comprising a nucleic acid sequence selected from the nucleic acid sequences set forth in SEQ ID NOs: 1, 2 or 3, 4 and 5 or 6 to obtain an expression profile for the patient, and d) performing analysis of the expression profile of the patient with expression profiles of target genes from patients previously clinically classified as breast cancer and expression profiles of target genes from patients previously clinically classified as benign breast disease, wherein: if the expression profile of the patient is clustered with the expression profiles from patients previously clinically classified as breast cancer, then the patient is prognosticated to have breast cancer, and if the expression profile of the patient is clustered with the expression profiles from patients previously clinically classified as benign breast disease, then the patient is prognosticated to have a benign breast disease.

In one embodiment, in step b) the biological material is brought into contact with reagents specific for a combination of at least 4 and no more than 28 target genes, wherein the reagents include at least reagents specific for the target genes comprising the nucleic acid sequence set forth in SEQ ID NOs 1, 2 or 3, 4 and 5 or 6, respectively, and the expression level of at least said 4 genes is determined in step c) to obtain the expression profile for the patient.

In another embodiment, in step b) the biological material is brought into contact with reagents specific for a combination of 28 genes, wherein the reagents include reagents specific for the target genes comprising the nucleic acid sequence set forth in SEQ ID NOs 1 to 44 respectively, and the expression level of the 28 genes is determined in step c) to obtain the expression profile for the patient.

Particularly, the biological sample taken from the patient is a blood sample. More particularly, the biological material comprises nucleic acids.

In one embodiment, the at least one specific reagent of step b) comprises at least one hybridization probe. In another embodiment, the specific reagents of step b) comprises at least one hybridization probe and at least one primer. In a further embodiment, the specific reagents of step b) comprises one hybridization probe and two primers.

The present invention also provides a kit for discriminating breast cancer from benign breast disease in a biological sample from a patient comprises at least one specific reagent for at least one target gene and no more than 28 specific reagents for 28 target genes comprising the nucleic acid sequences set forth in SEQ ID NOs 1 to 44, wherein the at least one reagent is specific for at least a target gene comprising a nucleic acid sequence selected from the nucleic acid sequences set forth in SEQ ID NOs: 1, 2 or 3, 4 and 5 or 6.

In one embodiment, the kit of the present invention comprises reagents specific for a combination of at least 4 and no more than 28 target genes, wherein the reagents include at least reagents specific for the target genes comprising the nucleic acid sequence set forth in SEQ ID NOs 1, 2 or 3, 4 and 5 or 6, respectively.

In another embodiment, the kit of the present invention comprises reagents specific for a combination of 28 target genes, wherein the reagents include reagents specific for the target genes comprising the nucleic acid sequence set forth in SEQ ID NOs 1 to 44.

The present invention also relates to the use of at least one specific reagent for at least one target gene and no more than specific reagents for 28 target genes comprising the nucleic acid sequences set forth in SEQ ID NOs 1 to 44 in the manufacture of a composition for discriminating breast cancer from benign breast disease in a biological sample from a patient, wherein the at least one reagent is specific for at least a target gene comprising a nucleic acid sequence selected from the nucleic acid sequences set forth in SEQ ID NOs: 1, 2 or 3, 4 and 5 or 6.

In one embodiment, the present invention relates to use of reagents specific for a combination of at least 4 and no more than 28 target genes in the manufacture of a composition for discriminating breast cancer from benign breast disease in a biological sample from a patient, wherein the reagents include at least reagents specific for the target genes comprising the nucleic acid sequence set forth in SEQ ID NOs 1, 2 or 3, 4 and 5 or 6, respectively.

In another embodiment, the present invention relates to use of a combination of 28 target genes in the manufacture of a composition for discriminating breast cancer from benign breast disease in a biological sample from a patient, wherein the reagents include reagents specific for the target genes comprising the nucleic acid sequence set forth in SEQ ID NOs 1 to 44.

DETAILED DESCRIPTION OF THE INVENTION

The present invention proposes to solve all the drawbacks of the prior art by providing a diagnostic tool for discriminating within BI-RADS 0 patients, between BC and BBD. Considering most of the patients whose mammography classified as BI-RADS 0 have breast lesion, the present study aims to discriminate BC from BBD. This is very different from the earlier researches which focused on the expression pattern of breast cancer patients and patients with no signs of this disease. That eliminates some not cancer-specific factors to the detection of cancer such as some inflammatory response regulation.

Surprisingly, the inventors have demonstrated that the analysis of the expression of at least one target gene selected from CHI3, CLEC4C, LILRA3 and TUBB2A gives an information that is sufficient for distinguishing BDD patients from BC. Of course, the analysis of the expression of the above target genes, taken in combination, improves the sensitivity and the specificity of the result, likewise the analysis of the expression profile of 28 target genes, such as described below in table 1, including CHI3, CLEC4C, LILRA3 and TUBB2A.

TABLE 1

| SEQ ID NOs: | Abbreviated name | Name of gene | Accession number |
|---|---|---|---|
| 1 | CHI3L1 | Chitinase 3-like 1 (cartilage glycoprotein-39) | ENST00000255409 |
| 2 | CLEC4C | C-type lectin domain family 4, member C | ENST00000354629 |
| 3 | | | ENST00000360345 |
| 4 | LILRA3 | Leukocyte immunoglobulin-like receptor, subfamily A (without TM domain), member 3 | ENST00000251390 |
| 5 | TUBB2A | Tubulin, beta 2A | ENST00000259218 |
| 6 | | | ENST00000333628 |
| 7 | ADAM12 | ADAM metallopeptidase domain 12 | ENST00000368676 |
| 8 | CHURC1 | Churchill domain containing 1 | ENST00000359118 |
| 9 | RNF182 | Ring finger protein 182 | ENST00000313403 |
| 10 | TMEM176B | Transmembrane protein 176B | ENST00000326442 |
| 11 | | | ENST00000429904 |
| 12 | | | ENST00000434545 |
| 13 | | | ENST00000447204 |
| 14 | FAM118A | Family with sequence similarity 118, member A | ENST00000216214 |
| 15 | | | ENST00000441876 |
| 16 | ANKRD20A | Ankyrin repeat domain 20 family, member A1/2/3/4/5 | ENST00000377477 |
| 17 | KLRC1/2 | Killer cell lectin-like receptor subfamily C, | ENST00000347831 |
| 18 | | member 1/2 | ENST00000359151 |
| 19 | | | ENST00000381902 |
| 20 | KIAA1671 | KIAA1671 protein | ENST00000358431 |
| 21 | ZBTB44 | Zinc finger and BTB domain containing 44 | ENST00000454539 |
| 22 | LQK1 | LQK1 hypothetical protein short isoform | NR_027285 |
| 23 | | | NR_027286 |
| 24 | APOBEC3A | Apolipoprotein B mRNA editing enzyme, catalytic | ENST00000249116 |
| 25 | | polypeptide-like 3A | ENST00000402255 |
| 26 | LOC283788 | Homo sapiens cDNA FLJ90087 fis, clone HEMBA1005230, weakly similar to zinc protein 140 | NR_027436 |
| 27 | FAM87A/B | Family with sequence similarity 87, member A/B | ENST00000330148 |
| 28 | LOC642236 | Similar to FRG1 protein (FSHD region gene 1 protein) | ENST00000226798 |
| 29 | C4A/B | Complement component 4A/B | ENST00000428596 |
| 30 | ENTPD5 | Ectonucleoside triphosphate diphosphohydrolase5 | ENST00000334696 |
| 31 | LOC728263 | Similar to hCG1818012 | NG_008780 |
| 32 | MGC15705 | Putative uncharacterized protein MGC15705. | ENST00000425084 |
| 33 | FAM160A1 | Family with sequence similarity 160 A1 | ENST00000340515 |

TABLE 1-continued

| SEQ ID NOs: | Abbreviated name | Name of gene | Accession number |
|---|---|---|---|
| 34 | | | ENST00000435205 |
| 35 | PLXDC1 | Plexin domain containing 1 | ENST00000315392 |
| 36 | SFN | Stratifin | ENST00000339276 |
| 37 | CLU | Clusterin | ENST00000316403 |
| 38 | | | ENST00000380446 |
| 39 | | | ENST00000405140 |
| 40 | PSPH | Phosphoserine phosphatase | ENST00000275605 |
| 41 | | | ENST00000395471 |
| 42 | | | ENST00000437355 |
| 43 | HLA-DQB1 | Major Histocompatibility Complex, class II, DQB1 | ENST00000399084 |
| 44 | | | ENST00000434651 |

Several variants sometimes exist for the same target gene, as revealed, for example, in table 1. In the present invention, all the variants are relevant and are indifferently analyzed. It is clearly understood that, if various isoforms of these genes exist, all the isoforms are relevant for the present invention.

The inventors have identified peripheral blood mRNA signatures which can help to discriminate breast cancer from benign breast disease, with a particular interest in patients with non-conclusive mammography.

Accordingly the present invention relates to a method for discriminating between breast cancer and benign breast disease in a biological sample from a patient, wherein it comprises the following steps:

a) obtaining the biological sample comprising a biological material from the patient, b) contacting the biological material from the biological sample with at least one specific reagent for at least one target gene and no more than 28 specific reagents for 28 target genes comprising the nucleic acid sequences set forth in SEQ ID NOs 1 to 44, wherein the at least one reagent is specific for at least a target gene comprising a nucleic acid sequence selected from the nucleic acid sequences set forth in SEQ ID NOs: 1, 2 or 3, 4 and 5 or 6, and c) determining the expression level of at least one target gene comprising a nucleic acid sequence selected from the nucleic acid sequences set forth in SEQ ID NOs: 1, 2 or 3, 4 and 5 or 6 to obtain an expression profile for the patient, and d) performing analysis of the expression profile of the patient with expression profiles of target genes from patients previously clinically classified as breast cancer and expression profiles of target genes from patients previously clinically classified as benign breast disease, wherein: if the expression profile of the patient is clustered with the expression profiles from patients previously clinically classified as breast cancer, then the patient is prognosticated to have breast cancer, and if the expression profile of the patient is clustered with the expression profiles from patients previously clinically classified as benign breast disease, then the patient is prognosticated to have a benign breast disease.

In one or more embodiments it is possible in step b) to bring the biological material into contact with reagents specific for a combination of at least 2, or at least 3 or at least 4 target genes and no more than 28 target genes, wherein the reagents include at least reagents specific for the target genes comprising the nucleic acid sequence set forth in any one of SEQ ID NOs 1, 2 or 3, 4 and 5 or 6, respectively, and the expression level of at least 2, 3 or 4 genes is determined in step c).

Examples of combination of target genes are described below:
SEQ ID NO: 1 and SEQ ID NO: 2 or 3
SEQ ID NO: 1 and SEQ ID NO: 4
SEQ ID NO: 1 and SEQ ID NO: 5 or 6
SEQ ID NO: 2 or 3 and SEQ ID NO: 4
SEQ ID NO: 2 or 3 and SEQ ID NO: 5 or 6
SEQ ID NO: 4 and SEQ ID NO: 5 or 6
SEQ ID NO: 1, SEQ ID NO: 2 or 3 and SEQ ID NO: 4
SEQ ID NO: 1, SEQ ID NO: 2 or 3 and SEQ ID NO: 5 or 6
SEQ ID NO: 1, SEQ ID NO: 4 and SEQ ID NO: 5 or 6
SEQ ID NO: 2 or 3, SEQ ID NO: 4 and SEQ ID NO: 5 or 6
SEQ ID NO: 4, SEQ ID NO: 5 or 6 and SEQ ID NO: 2 or 3, and
SEQ ID NO: 1, SEQ ID NO: 2 or 3, SEQ ID NO: 4 and SEQ ID NO: 5 or 6; the following combinations of target genes SEQ ID NO: 1,
SEQ ID NO: 2, SEQ ID NO: 4 and SEQ ID NO: 5 and SEQ ID NO: 1,
SEQ ID NO: 3, SEQ ID NO: 4 and SEQ ID NO: 6 being preferred.

Consequently, in one embodiment of the method of the present invention in step b) the biological material is brought into contact with reagents specific for a combination of at least 4 and no more than 28 target genes, wherein the reagents include at least reagents specific for the target genes comprising the nucleic acid sequence set forth in SEQ ID NOs 1, 2 or 3, 4 and or 6, respectively, and the expression level of at least said 4 genes is determined in step c) to obtain the expression profile for the patient.

In another embodiment of the method in step b) the biological material is brought into contact with reagents specific for a combination of 28 genes, wherein the reagents include reagents specific for the target genes comprising the nucleic acid sequence set forth in SEQ ID NOs 1 to 44 respectively, and the expression level of the 28 genes is determined in step c) to obtain the expression profile for the patient.

The biological sample taken from the patient is any sample liable to contain a biological material as defined hereinafter, in particular blood, plasma, serum, tissue, circulating cells sample, blood sample being preferred. This biological sample is provided by any type of sampling known to those skilled in the art.

In an embodiment of the method of the invention, the biological material can be extracted from the biological sample by any of the nucleic acid extraction and purification protocols well known to those skilled in the art. In another embodiment of the present invention the target biological material is not extracted from the biological sample and its analysis is directly performed from the sample.

The term "biological material" is intended to mean any material that makes it possible to detect the expression of a target gene. The biological material may in particular comprise proteins, or nucleic acids, such as, in particular, deoxyribonucleic acids (DNA) or ribonucleic acids (RNA). The nucleic acid may in particular be an RNA (ribonucleic acid).

According to a preferred embodiment of the invention, the biological material is extracted in step and comprises nucleic acids, preferably RNAs, and even more preferably total RNA. Total RNA comprises transfer RNAs (tRNA), messenger RNAs (mRNAs), such as the mRNAs transcribed from the target gene, but also transcribed from any other gene, and ribosomal RNAs. This biological material comprises material specific for a target gene, such as in particular the mRNAs transcribed from the target gene or the proteins derived from these mRNAs.

By way of indication, the nucleic acid extraction can be carried out by: a step consisting of lysis of the cells present in the biological sample, in order to release the nucleic acids contained in the cells of the patient. By way of example, use may be made of the methods of lysis as described in patent applications: WO 00/05338 regarding mixed magnetic and mechanical lysis, WO 99/53304 regarding electrical lysis, WO 99/15321 regarding mechanical lysis. Those skilled in the art may use other well-known methods of lysis, such as thermal or osmotic shocks or chemical lyses using chaotropic agents such as guanidinium salts (U.S. Pat. No. 5,234,809); a purification step, for separating the nucleic acids from the other cellular constituents released in the lysis step. This generally makes it possible to concentrate the nucleic acids, and can be adapted to the purification of DNA or of RNA. By way of example, use may be made of magnetic particles optionally coated with oligonucleotides, by adsorption or covalence (in this respect, see U.S. Pat. No. 4,672,040 and U.S. Pat. No. 5,750,338), and the nucleic acids which are bound to these magnetic particles can thus be purified by means of a washing step. This nucleic acid purification step is particularly advantageous if it is desired to subsequently amplify said nucleic acids. A particularly advantageous embodiment of these magnetic particles is described in patent applications: WO-A-97/45202 and WO-A-99/35500.

The term "specific reagent" is intended to mean a reagent which, when it is brought into contact with biological material as defined above, binds with the material specific for said target gene. By way of indication, when the specific reagent and the biological material are of nucleic origin, bringing the specific reagent into contact with the biological material allows the specific reagent to hybridize with the material specific for the target gene. The term "hybridization" is intended to mean the process during which, under appropriate conditions, two nucleotide fragments bind with stable and specific hydrogen bonds so as to form a double-stranded complex. These hydrogen bonds form between the complementary adenine (A) and thymine (T) (or uracile (U)) bases (this is referred to as an A-T bond) or between the complementary guanine (G) and cytosine (C) bases (this is referred to as a G--C bond). The hybridization of two nucleotide fragments may be complete (reference is then made to complementary nucleotide fragments or sequences), i.e. the double-stranded complex obtained during this hybridization comprises only A-T bonds and C-G bonds. This hybridization may be partial (reference is then made to sufficiently complementary nucleotide fragments or sequences), i.e. the double-stranded complex obtained comprises A-T bonds and C-G bonds that make it possible to form the double-stranded complex, but also bases not bound to a complementary base. The hybridization between two nucleotide fragments depends on the working conditions that are used, and in particular on the stringency. The stringency is defined in particular as a function of the base composition of the two nucleotide fragments, and also by the degree of mismatching between two nucleotide fragments. The stringency can also depend on the reaction parameters, such as the concentration and the type of ionic species present in the hybridization solution, the nature and the concentration of denaturing agents and/or the hybridization temperature. All these data are well known and the appropriate conditions can be determined by those skilled in the art. In general, depending on the length of the nucleotide fragments that it is intended to hybridize, the hybridization temperature is between approximately 20 and 70.degree. C., in particular between 35 and 65.degree. C. in a saline solution at a concentration of approximately 0.5 to 1 M. A sequence, or nucleotide fragment, or oligonucleotide, or polynucleotide, is a series of nucleotide motifs assembled together by phosphoric ester bonds, characterized by the informational sequence of the natural nucleic acids, capable of hybridizing to a nucleotide fragment, it being possible for the series to contain monomers having different structures and to be obtained from a natural nucleic acid molecule and/or by genetic recombination and/or by chemical synthesis. A motif is a derivative of a monomer which may be a natural nucleotide of nucleic acid, the constitutive elements of which are a sugar, a phosphate group and a nitrogenous base; in DNA, the sugar is deoxy-2-ribose, in RNA, the sugar is ribose; depending on whether DNA or RNA is involved, the nitrogenous base is selected from adenine, guanine, uracile, cytosine and thymine; alternatively the monomer is a nucleotide that is modified in at least one of the three constitutive elements; by way of example, the modification may occur either at the level of the bases, with modified bases such as inosine, methyl-5-deoxycytidine, deoxyuridine, dimethylamino-5-deoxyuridine, diamino-2,6-purine, bromo-5-deoxyuridine or any other modified base capable of hybridization, or at the level of the sugar, for example the replacement of at least one deoxyribose with a polyamide (P. E. Nielsen et al, Science, 254, 1497-1500 (1991)[3]), or else at the level of the phosphate group, for example its replacement with esters in particular selected from diphosphates, alkyl- and arylphosphonates and phosphorothioates.

According to a specific embodiment of the invention, the specific reagent comprises at least one hybridization probe or at least one hybridization probe and at least one primer which is specific for the target gene or at least one hybridization probe and two primers specific for the target genes.

For the purpose of the present invention, the term "amplification primer" is intended to mean a nucleotide fragment comprising from 5 to 100 nucleotides, preferably from 15 to 30 nucleotides that allow the initiation of an enzymatic polymerization, for instance an enzymatic amplification reaction. The term "enzymatic amplification reaction" is intended to mean a process which generates multiple copies of a nucleotide fragment through the action of at least one enzyme. Such amplification reactions are well known to those skilled in the art and mention may in particular be made of the following techniques: PCR (polymerase chain reaction), as described in U.S. Pat. No. 4,683,195, 4,683,202 and 4,800,159, LCR (ligase chain reaction), disclosed, for, example, in patent application EP 0 201 184, RCR (repair chain reaction), described in patent application WO 90/01069, 3SR (self sustained sequence replication) with patent application WO 90/06995, NASBA (nucleic acid sequence-based amplification) with patent application WO 91/02818, TMA (transcription mediated amplification) with U.S. Pat. No. 5,399,491 and RT-PCR.

When the enzymatic amplification is a PCR, the specific reagent comprises at least two amplification primers, specific for a target gene, that allow the amplification of the material specific for the target gene. The material specific for the target gene then preferably comprises a complementary DNA obtained by reverse transcription of messenger RNA derived from the target gene (reference is then made to target-gene-specific cDNA) or a complementary RNA obtained by transcription of the cDNAs specific for a target gene (reference is then made to target-gene-specific cRNA). When the enzymatic amplification is a PCR carried out after a reverse transcription reaction, reference is made to RT-PCR.

The term "hybridization probe" is intended to mean a nucleotide fragment comprising at least 5 nucleotides, such as from 5 to 100 nucleotides, in particular from 10 to 75 nucleotides, such as 15-35 nucleotides and 60-70 nucleotides, having a hybridization specificity under given conditions so as to form a hybridization complex with the material specific for a target gene. In the present invention, the material specific for the target gene may be a nucleotide sequence included in a messenger RNA derived from the target gene (reference is then made to target-gene-specific mRNA), a nucleotide sequence included in a complementary DNA obtained by reverse transcription of said messenger RNA (reference is then made to target-gene-specific cDNA), or else a nucleotide sequence included in a complementary RNA obtained by transcription of said cDNA as described above (reference will then be made to target-gene-specific cRNA). The hybridization probe may include a label for its detection. The term "detection" is intended to mean either a direct detection such as a counting method, or an indirect detection by a method of detection using a label. Many methods of detection exist for detecting nucleic acids (see, for example, Kricka et al., Clinical Chemistry, 1999, no 45 (4), p. 453-458 [4] or Keller G. H. et al., DNA Probes, 2nd Ed., Stockton Press, 1993, sections 5 and 6, p. 173-249 [5]). The term "label" is intended to mean a tracer capable of generating a signal that can be detected. A non limiting list of these tracers includes enzymes which produce a signal that can be detected, for example, by colorimetry, fluorescence or luminescence, such as horseradish peroxidase, alkaline phosphatase, beta-galactosidase, glucose-6-phosphate dehydrogenase; chromophores such as fluorescent, luminescent or dye compounds; electron dense groups detectable by electron microscopy or by virtue of their electrical properties such as conductivity, by amperometry or voltametry methods, or by impedance measurement; groups that can be detected by optical methods such as diffraction, surface plasmon resonance, or contact angle variation, or by physical methods such as atomic force spectroscopy, tunnel effect, etc.; radioactive molecules such as 32P, 35S or 125I.

For the purpose of the present invention, the hybridization probe may be a "detection" probe. In this case, the "detection" probe is labeled by means of a label. The detection probe may in particular be a "molecular beacon" detection probe as described by Tyagi & Kramer (Nature biotech, 1996, 14:303-308 [6]). These "molecular beacons" become fluorescent during the hybridization. They have a stem-loop-type structure and contain a fluorophore and a "quencher" group. The binding of the specific loop sequence with its complementary target nucleic acid sequence causes the stem to unroll and the emission of a fluorescent signal during excitation at the appropriate wavelength. The detection probe in particular may be a "reporter probe" comprising a "color-coded barecode" according to NanoStringTM's technology.

For the detection of the hybridization reaction, use may be made of target sequences that have been labeled, directly (in particular by the incorporation of a label within the target sequence) or indirectly (in particular using a detection probe as defined above). It is in particular possible to carry out, before the hybridization step, a step consisting in labeling and/or cleaving the target sequence, for example using a labeled deoxy-ribonucleotide triphosphate during the enzymatic amplification reaction. The cleavage may be carried out in particular by the action of imidazole or of manganese chloride. The target sequence may also be labeled after the amplification step, for example by hybridizing a detection probe according to the sandwich hybridization technique described in document WO 91/19812. Another specific preferred method of labeling nucleic acids is described in application FR 2780059.

According to a preferred embodiment of the invention, the detection probe comprises a fluorophore and a quencher.

According to an even more preferred embodiment of the invention, the hybridization probe comprises an FAM (6-carboxy-fluorescein) or ROX (6-carboxy-X-rhodamine) fluorophore at its 5' end and a quencher (Dabsyl) at its 3' end.

The hybridization probe may also be a "capture" probe. In this case, the "capture" probe is immobilized or can be immobilized on a solid substrate by any appropriate means, i.e. directly or indirectly, for example by covalence or adsorption. As solid substrate, use may be made of synthetic materials or natural materials, optionally chemically modified, in particular polysaccharides such as cellulose-based materials, for example paper, cellulose derivatives such as cellulose acetate and nitrocellulose or dextran, polymers, copolymers, in particular based on styrene-type monomers, natural fibers such as cotton, and synthetic fibers such as nylon; inorganic materials such as silica, quartz, glasses or ceramics; latices; magnetic particles; metal derivatives, gels, etc. The solid substrate may be in the form of a microtitration plate, of a membrane as described in application WO-A-94/12670 or of a particle. It is also possible to immobilize on the substrate several different capture probes, each being specific for a target gene. In particular, a biochip on which a large number of probes can be immobilized may be used as substrate. The term "biochip" is intended to mean a solid substrate that is small in size, to which a multitude of capture probes are attached at predetermined positions. The biochip, or DNA chip, concept dates from the beginning of the 1990s. It is based on a multidisciplinary technology that integrates microelectronics, nucleic acid chemistry, image analysis and information technology. The operating principle is based on a foundation of molecular biology: the hybridization phenomenon, i.e. the pairing, by complementarity, of the bases of two DNA and/or RNA sequences. The biochip method is based on the use of capture probes attached to a solid substrate, on which probes a sample of target nucleotide fragments directly or indirectly labeled with fluorochromes is made to act. The capture probes are positioned specifically on the substrate or chip and each hybridization gives a specific piece of information, in relation to the target nucleotide fragment. The pieces of information obtained are cumulative, and make it possible, for example, to quantify the level of expression of one or more target genes. In order to analyze the expression of a target gene, a substrate comprising a multitude of probes, which correspond to all or part of the target gene, which is transcribed to mRNA, can then be prepared. For the purpose of the present invention, the term "low-density substrate" is intended to mean a substrate comprising fewer than 50 probes. For the purpose of the present invention, the term "medium-density substrate" is intended to mean a substrate comprising from 50 probes to 10 000 probes. For the purpose of the present invention, the term "high-density substrate" is intended to mean a substrate comprising more than 10 000 probes.

The cDNAs or cRNAs specific for a target gene that it is desired to analyze are then hybridized, for example, to specific capture probes. After hybridization, the substrate or chip is washed and the labeled cDNA or cRNA/capture probe complexes are revealed by means of a high-affinity ligand bound, for example, to a fluorochrome-type label. The fluorescence is read, for example, with a scanner and the analysis of the fluorescence is processed by information technology. By way of indication, mention may be made of the DNA chips developed by the company Affymetrix ("Accessing Genetic Information with High-Density DNA arrays", M. Chee et al., Science, 1996, 274, 610-614 [7]. "Light-generated oligonucleotide arrays for rapid DNA sequence analysis", A. Caviani Pease et al., Proc. Natl. Acad. Sci. USA, 1994, 91, 5022-5026 [8]), for molecular diagnoses. In this technology, the capture probes are generally small in size, around 25 nucleotides. Other examples of biochips are given in the publications by G. Ramsay, Nature Biotechnology, 1998, No. 16, p. 40-44 [9]; F. Ginot, Human Mutation, 1997, No. 10, p. 1-10 [10]; J. Cheng et al, Molecular diagnosis, 1996, No. 1 (3), p. 183-200 [11]; T. Livache et al, Nucleic Acids Research, 1994, No. 22 (15), p. 2915-2921 [12]; J. Cheng et al, Nature Biotechnology, 1998, No. 16, p. 541-546 [13] or in U.S. Pat. Nos. 4,981,783, 5,700,637, 5,445,934, 5,744,305 and 5,807,522. The main characteristic of the solid substrate should be to conserve the hybridization characteristics of the capture probes on the target nucleotide fragments while at the same time generating a minimum background noise for the method of detection. Three main types of fabrication can be distinguished for immobilizing the probes on the substrate.

First of all, there is a first technique which consists in depositing pre-synthesized probes. The attachment of the probes is carried out by direct transfer, by means of micropipettes or of microdots or by means of an inkjet device. This technique allows the attachment of probes having a size ranging from a few bases (5 to 10) up to relatively large sizes of 60 bases (printing) to a few hundred bases (microdeposition).

Printing is an adaptation of the method used by inkjet printers. It is based on the propulsion of very small spheres of fluid (volume <1 nl) at a rate that may reach 4000 drops/second. The printing does not involve any contact between the system releasing the fluid and the surface on which it is deposited.

Microdeposition consists in attaching long probes of a few tens to several hundred bases to the surface of a glass slide. These probes are generally extracted from databases and are in the form of amplified and purified products. This technique makes it possible to produce chips called microarrays that carry approximately ten thousand spots, called recognition zones, of DNA on a surface area of a little less than 4 cm.sup.2. The use of nylon membranes, referred to as "macroarrays", which carry products that have been amplified, generally by PCR, with a diameter of 0.5 to 1 mm and the maximum density of which is 25 spots/cm.sup.2, should not however be forgotten. This very flexible technique is used by many laboratories. In the present invention, the latter technique is considered to be included among biochips. A certain volume of sample can, however, be deposited at the bottom of a microtitration plate, in each well, as in the case in patent applications WO-A-00/71750 and FR 00/14896, or a certain number of drops that are separate from one another can be deposited at the bottom of one and the same Petri dish, according to another patent application, FR 00/14691.

The second technique for attaching the probes to the substrate or chip is called in situ synthesis. This technique results in the production of short probes directly at the surface of the chip. It is based on in situ oligonucleotide synthesis (see, in particular, patent applications WO 89/10977 and WO 90/03382) and is based on the oligonucleotide synthesizer process. It consists in moving a reaction chamber, in which the oligonucleotide extension reaction takes place, along the glass surface.

Finally, the third technique is called photolithography, which is a process that is responsible for the biochips developed by Affymetrix. It is also an in situ synthesis. Photolithography is derived from microprocessor techniques. The surface of the chip is modified by the attachment of photolabile chemical groups that can be light-activated. Once illuminated, these groups are capable of reacting with the 3' end of an oligonucleotide. By protecting this surface with masks of defined shapes, it is possible to selectively illuminate and therefore activate areas of the chip where it is desired to attach one or other of the four nucleotides. The successive use of different masks makes it possible to alternate cycles of protection/reaction and therefore to produce the oligonucleotide probes on spots of approximately a few tens of square micrometers (μm2). This resolution makes it possible to create up to several hundred thousand spots on a surface area of a few square centimeters (cm2). Photolithography has advantages: in bulk in parallel, it makes it possible to create a chip of N-mers in only 4.times.N cycles. All these techniques can be used with the present invention. According to a preferred embodiment of the invention, the at least one specific reagent of step b) defined above comprises at least one hybridization probe which is preferably immobilized on a substrate. This substrate is preferably a low-, high- or medium-density substrate as defined above.

These hybridization steps on a substrate comprising a multitude of probes may be preceded by an enzymatic amplification reaction step, as defined above, in order to increase the amount of target genetic material. In step c), the determination of the expression level of a target gene can be carried out by any of the protocols known to those skilled in the art. In general, the expression of a target gene can be analyzed by detecting the mRNAs (messenger RNAs) that are transcribed from the target gene at a given moment or by detecting the proteins derived from these mRNAs.

The invention preferably relates to the determination of the expression level of a target gene by detection of the mRNAs derived from this target gene according to any of the protocols well known to those skilled in the art. According to a specific embodiment of the invention, the expression level of several target genes is determined simultaneously, by detection of several different mRNAs, each mRNA being derived from a target gene.

When the specific reagent comprises at least one amplification primer, it is possible, to determine the expression level of the target gene in the following way: 1) After having extracted, as biological material, the total RNA (comprising the transfer RNAs (tRNAs), the ribosomal RNAs (rRNAs) and the messenger RNAs (mRNAs)) from a biological sample as presented above, a reverse transcription step is carried out in order to obtain the complementary DNAs (or cDNAs) of said mRNAs. By way of indication, this reverse transcription reaction can be carried out using a reverse transcriptase enzyme which makes it possible to obtain, from an RNA fragment, a complementary DNA fragment. The reverse transcriptase enzyme from AMV (Avian Myoblastosis Virus) or from MMLV (Moloney Murine Leukaemia Virus) can in particular be used. When it is more particularly desired to obtain only the cDNAs of the mRNAs, this reverse transcription step is carried out in the presence of nucleotide fragments comprising only thymine bases (polyT), which hybridize by complementarity to the polyA sequence of the mRNAs so as to form a polyT-polyA complex which then serves as a starting point for the reverse transcription reaction carried out by the reverse transcriptase enzyme. cDNAs complementary to the mRNAs derived from a target gene (target-gene-specific cDNA) and cDNAs complementary to the mRNAs derived from genes other than the target gene (cDNAs not specific for the target gene) are then obtained. 2) The amplification primer(s) specific for a target gene is (are) brought into contact with the target-gene-specific cDNAs and the cDNAs not specific for the target gene. The amplification primer(s) specific for a target gene hybridize(s) with the target-gene-specific cDNAs and a predetermined region, of known length, of the cDNAs originating from the mRNAs derived from the target gene is specifically amplified. The cDNAs not specific for the target gene are not amplified, whereas a large amount of target-gene-specific cDNAs is then obtained. For the purpose of the present invention, reference is made, without distinction, to "target-gene-specific cDNAs" or to "cDNAs originating from the mRNAs derived from the target gene". This step can be carried out in particular by means of a PCR-type amplification reaction or by any other amplification technique as defined above. By PCR, it is also possible to simultaneously amplify several different cDNAs, each one being specific for different target genes, by using several pairs of different amplification primers, each one being specific for a target gene: reference is then made to multiplex amplification. 3) The expression of the target gene is determined by detecting and quantifying the target-gene-specific cDNAs obtained in step 2) above. This detection can be carried out after electrophoretic migration of the target-gene-specific cDNAs according to their size. The gel and the medium for the migration can include ethidium bromide so as to allow direct detection of the target-gene-specific cDNAs when the gel is placed, after a given migration period, on a UV (ultraviolet)-ray light table, through the emission of a light signal. The greater the amount of target-gene-specific cDNAs, the brighter this light signal. These electrophoresis techniques are well known to those skilled in the art. The target-gene-specific cDNAs can also be detected and quantified using a quantification range obtained by means of an amplification reaction carried out until saturation. In order to take into account the variability in enzymatic efficiency that may be observed during the various steps (reverse transcription, PCR, etc.), the expression of a target gene of various groups of patients can be normalized by simultaneously determining the expression of a "housekeeping" gene, the expression of which is similar in the various groups of patients. By realizing a ratio of the expression of the target gene to the expression of the housekeeping gene, i.e. by realizing a ratio of the amount of target-gene-specific cDNAs to the amount of housekeeping-gene-specific cDNAs, any variability between the various experiments is thus corrected. Those skilled in the art may refer in particular to the following publications: Bustin S A, J Mol Endocrinol, 2002, 29: 23-39; Giulietti A Methods, 2001, 25: 386-401.

When the specific reagent comprises at least one hybridization probe, the expression of a target gene can be determined in the following way: 1) After having extracted, as biological material, the total RNA from a biological sample as presented above, a reverse transcription step is carried out as described above in order to obtain cDNAs complementary to the mRNAs derived from a target gene (target-gene-specific cDNA) and cDNAs complementary to the mRNAs derived from genes other than the target gene (cDNA not specific for the target gene). 2) All the cDNAs are brought into contact with a substrate, on which are immobilized capture probes specific for the target gene whose expression it is desired to analyze, in order to carry out a hybridization reaction between the target-gene-specific cDNAs and the capture probes, the cDNAs not specific for the target gene not hybridizing to the capture probes. The hybridization reaction can be carried out on a solid substrate which includes all the materials as indicated above. According to a preferred embodiment, the hybridization probe is immobilized on a substrate. Preferably, the substrate is a low-, high- or medium-density substrate as defined above. The hybridization reaction may be preceded by a step consisting of enzymatic amplification of the target-gene-specific cDNAs as described above, so as to obtain a large amount of target-gene-specific cDNAs and to increase the probability of a target-gene-specific cDNA hybridizing to a capture probe specific for the target gene. The hybridization reaction may also be preceded by a step consisting in labeling and/or cleaving the target-gene-specific cDNAs as described above, for example using a labeled deoxyribonucleotide triphosphate for the amplification reaction. The cleavage can be carried out in particular by the action of imidazole and manganese chloride. The target-gene-specific cDNA can also be labeled after the amplification step, for example by hybridizing a labeled probe according to the sandwich hybridization technique described in document WO-A-91/19812. Other preferred specific methods for labeling and/or cleaving nucleic acids are described in applications WO 99/65926, WO 01/44507, WO 01/44506, WO 02/090584, WO 02/090319. 3) A step consisting of detection of the hybridization reaction is subsequently carried out. The detection can be carried out by bringing the substrate on which the capture probes specific for the target gene are hybridized with the target-gene-specific cDNAs into contact with a "detection" probe labeled with a label, and detecting the signal emitted by the label. When the target-gene-specific cDNA has been labeled beforehand with a label, the signal emitted by the label is detected directly.

When the at least one specific reagent is brought into contact in step b) comprises at least one hybridization probe, the expression of a target gene can also be determined in the following way: 1) After having extracted, as biological material, the total RNA from a biological sample as presented above, a reverse transcription step is carried out as described above in order to obtain the cDNAs of the mRNAs of the biological material. The polymerization of the complementary RNA of the cDNA is subsequently carried out using a T7 polymerase enzyme which functions under the control of a promoter and which makes it possible to obtain, from a DNA template, the complementary RNA. The cRNAs of the cDNAs of the mRNAs specific for the target gene (reference is then made to target-gene-specific cRNA) and the cRNAs of the cDNAs of the mRNAs not specific for the target gene are then obtained. 2) All the cRNAs are brought into contact with a substrate on which are immobilized capture probes specific for the target gene whose expression it is desired to analyze, in order to carry out a hybridization reaction between the target-gene-specific cRNAs and the capture probes, the cRNAs not specific for the target gene not hybridizing to the capture probes. When it is desired to simultaneously analyze the expression of several target genes, several different capture probes can be immobilized on the substrate, each one being specific for a target gene. The hybridization reaction may also be preceded by a step consisting in labeling and/or cleaving the target-gene-specific cRNAs as described above. 3) A step consisting of detection of the hybridization reaction is subsequently carried out. The detection can be carried out by bringing the substrate on which the capture probes specific for the target gene are hybridized with the target-gene-specific cRNA into contact with a "detection" probe labeled with a label, and detecting the signal emitted by the label. When the target-gene-specific cRNA has been labeled beforehand with a label, the signal emitted by the label is detected directly. The use of cRNA is particularly advantageous when a substrate of biochip type on which a large number of probes are hybridized is used.

The invention also relates to a substrate, comprising at least 4 hybridization probes selected from probes specific for the target genes with a nucleic sequence having any one of SEQ ID NOs 1 to 44 and in particular 4 hybridization probes specific for the target genes with a nucleic acid sequence having any one of SEQ ID NOs 1, 2 or 3, 4 and 5 or 6.

The invention further relates to the use of a substrate as defined above, for discriminating BC from BBD.

The present invention also concerns a kit for discriminating breast cancer from benign breast disease in a biological sample from a patient comprises at least one specific reagent for at least one target gene and no more than 28 specific reagents for 28 target genes comprising the nucleic acid sequences set forth in SEQ ID NOs 1 to 44, wherein the at least one reagent is specific for at least a target gene comprising a nucleic acid sequence selected from the nucleic acid sequences set forth in SEQ ID NOs: 1, 2 or 3 4 and 5 or 6.

The specific reagents can targeted a combination of at least two, three or four genes as described above in more detail but no more than 28 genes and in one embodiment the kit comprises reagents specific for a combination of at least 4 and no more than 28 target genes, wherein the reagents include at least reagents specific for the target genes comprising the nucleic acid sequence set forth in SEQ ID NOs 1, 2 or 3, 4 and 5 or 6, respectively. In another embodiment the kit comprises reagents specific for a combination of 28 target genes, wherein the reagents include reagents specific for the target genes comprising the nucleic acid sequence set forth in SEQ ID NOs 1 to 28.

EXAMPLES

I) Materials and Methods
1. Characteristic of Patients and Samples

Blood samples were collected from 84 patients with breast cancer and 94 patients with breast benign disease in this study. All patients had been referred to the Breast Surgery Department of Cancer Hospital, Fudan University (Shanghai, China) with suspected breast cancer between July 2007 and December 2008. Each of them went through the mammographic screening in the hospital, while all the BI-RADS category of the patients was determined by three professional radiologists. About 2.5 ml of peripheral blood were collected from each of 84 women with BC and 94 women with BBD, in Paxgene™ Blood RNA tubes (PreAnalytix) containing an RNA stabilizing solution. All blood samples were collected before fine-needle aspiration operation or any invasive steps which was indicated for cytological investigation on suspected breast lesion. Diagnosis of breast cancer was on the basis of identification of cancer cells on the core-needle biopsy or surgical specimen. Diagnosis of benign disease on the basis of lack of cancer cells at open biopsy. The protocol was approved by the local Ethical Committee for Clinical Research and written informed consent was obtained from all the patients recruited for the study. Final pathologic tumor stage was determined with the TNM staging system and graded using the Nottingham system. In addition tumor type and tumor grade, estrogen receptor (ER), progesterone receptor (PR) and Human Epidermal growth factor Receptor 2 (HER2) status and lymph node status were assessed in each tumor.

2. RNA Extraction and Microarray Analysis

Total RNA was extracted with the PAXGene Blood RNA® kit (PreAnalytix) according to the manufacturer's instruction. The quantity of total RNA was measured by spectrophotometer at optical density (OD) 260 nm and the quality was assessed using the RNA 6000 Nano LabChip on a 2100 Bioanalyzer (Agilent Technologies). Only samples with RNA Integrity Number (RIN) between 7 and 10 were analyzed. 50 ng of total RNA was then reversely transcribed and linearly amplified to single strand cDNA using Ribo-SPIA Ovation technology with WT-Ovation RNA Amplification System (NuGen Technologies), according to the manufacturer's standard protocol and the products were purified with QIAquick PCR purification kit (Qiagen GmbH). 2 μg amplified and purified cDNA was subsequently fragmented with RQ1 RNase-Free DNase (Promega corporation) and labeled with biotinylated deoxynucleoside triphosphates by Terminal Transferase (Roche Diagnostics GmbH) and DNA labeling reagent (Affymetrix). The labeled cDNA was hybridized onto HG U133 plus 2.0 Array (Affymetrix) in a Hybridization Oven 640 (Affymetrix) at 60 rpm, 50° C. for 18 h. The HG U133 plus 2.0 Array contains 54,675 probe sets representing approximately 39,000 best characterized human genes. After hybridization, the arrays were washed and stained according to the Affymetrix protocol EukGE-WS2v4 using an Affymetrix fluidic station FS450. The arrays were scanned with the Affymetrix scanner 3000.

3. Microarray Data Analysis

Quality Control and Preprocessing. Quality control analyses were performed according to the suggestions of standard Affymetrix quality control parameters. Based on the evaluation criteria, all blood sample measurements fulfilled the minimal quality requirements. The Affymetrix expression arrays were preprocessed by RMA (Robust Multi-chip Average) [10] with background correction, quantile normalization and median polish summarization. Probesets with extreme signal intensity (lower than 50 or higher than 214) were filtered out. Then, sequence information based filtering was performed according to the Entrez Gene database information. Probesets without Entrez Gene ID annotation were removed. For multiple probesets mapping to the same Entrez Gene ID, only the probeset with the largest value of Interquartile Range was retained and the others were removed. After all, to reduce the likelihood of batch, a normalization algorithm, ComBat [11] was applied. The ComBat method (statistics.byu.edu/johnson/ComBat/) applies either parametric or nonparametric empirical Bayes framework for adjusting batch effects in a given data set.

4. Molecular Signature Identification.

After appropriate pre-processing to reduce redundant probesets and batch variation across expression data, Molecular Signature Identification was performed based on the preprocessed expression data. 84 BC and 94 BBD samples with mammographic results and confirmed pathologic information were categorized into two groups, 79 BC+73 BBD with BI-RADS 1-5, and 5 BC+21 BBD with BI-RADS 0. 79 BC+73 BBD with BI-RADS 1-5 were used as train set to identify interesting genes by Recursive Feature Elimination (RFE) procedure, and build the classification model by Support Vector Machine (SVM) [12-13]. Inside train set, 5-fold cross validation process was conducted to determine the optimal gene sets. A list of top-100 genes was identified by RFE based on four of the fifth train set. The classification model was created based on the top-100 genes and the model was tested using another one of the fifth train set. This process was run for 1000 iterations, thus one thousand of top 100 gene sets were generated. Eventually, the genes appeared in entire one thousand of 100-top gene lists were identified as the most robust genes to generate the final model using the whole train set. And the model was then applied to completely unseen samples 5 BC+21 BBD with BI-RADS 0.

The preprocessing and statistical steps were executed using R-environment with Bioconductor libraries [14-18].

II) Results

1. Patient Characteristics

The present study was performed on 178 samples from 84 BC and 94 BBD patients with mammographic results and confirmed pathologic information, which then categorized in two groups, 79 BC+73 BBD with BI-RADS 1-5, and 5 BC+21 BBD with BI-RADS 0. Table 2 summarizes the clinical characteristics of these BC and BBD patient populations. Briefly, 92% of the cancer patients presented a T0-T2 tumor; 70% and 32% of the tumors were hormone receptor positive and Her2 positive respectively. Benign findings included 51.1% of breast disease, 27.7% of breast fibroadenoma and 21.2% intracanalicular papilloma respectively.

TABLE 2

Characteristics of the population

Benign Breast Disease (BBD): 94 patients

| Age (years) | | |
|---|---|---|
| Median | 47.4 | |
| Range | 34-75 | |
| Menopausal status | | |
| Postmenopausal | 30 | 33.7 |
| Premenoposal | 59 | 66.3 |
| Non determined | 5 | |
| Type of disease | | |
| Breast disease | 48 | 51.1% |
| Breast fiboadenoma | 26 | 27.7% |
| Intracanalicular papilloma | 20 | 21.2% |

Breast cancer (BD): 84 patients

| Age (years) | | |
|---|---|---|
| Median | 42.5 | |
| Range | 31-77 | |

TABLE 2-continued

Characteristics of the population

| Tumor type | | |
|---|---|---|
| Ductal carcinoma in Situ (DCIS) | 11 | 13.1% |
| Intra Ductal carcinoma (IDC) | 73 | 86.9% |
| Tumor size | | |
| T1 (0.1-2 cm) | 44 | 52.4% |
| T2 (>2-5 cm) | 34 | 40.5% |
| T3 (>5 cm) | 1 | 1.2% |
| unknown | 5 | 5.9% |
| Nodal status | | |
| Positive | 25 | 29.8% |
| Negative | 57 | 67.8% |
| Unknow | 2 | 2.4% |
| TNM Stage | | |
| 0 | 10 | 11.9% |
| I | 28 | 33.3% |
| II | 33 | 39.3% |
| III | 11 | 13.1% |
| Unknow | 2 | 2.4% |
| Histological grade | | |
| I | 1 | 1.2% |
| I-II | 3 | 3.6% |
| II | 43 | 51.2% |
| II-III | 8 | 9.5% |
| III | 18 | 21.4% |
| Unknow | 11 | 13.1% |
| Estrogen receptor status | | |
| Negative | 19 | 22.6% |
| Positive | 65 | 77.4% |
| Progeterone receptor status | | |
| Negative | 20 | 23.8% |
| Positive | 64 | 7.2% |
| Her-2 status | | |
| Negative | 53 | 63.1% |
| Positive | 31 | 36.9% |

*pValue

2. Construction and Performance of the Model

By using Recursive Feature Elimination (RFE) procedure and Support Vector Machine (SVM) classification, a set of 28-gene panel (Table 1) was developed, to discriminate BC and BBD patients with BI-RADS 1-5. This 28-gene panel was then tested in the BI-RADS 0 group.

Among the 28 predictive genes, the expression of 15 of them are down-expressed in BC compared to BBD and 13 are up-expressed in BC versus BBD, as summarized in table 3.

TABLE 3

| SEQ ID NOs: | Affymetrix probeset | Abbreviated name | Mean signal | P-value | Fold change | Expression in BC versus BBD |
|---|---|---|---|---|---|---|
| 1 | 209395_at | CHI3L1 | 271 | $5.74\ 10^{-3}$ | 1.22 | Down-regulated |
| 2-3 | 1552552_s_at | CLEC4C | 49 | $5.59\ 10^{-3}$ | 1.20 | Down-regulated |
| 4 | 206881_s_at | LILRA3 | 73 | $4\ 10^{-6}$ | 1.43 | Down-regulated |
| 5-6 | 204141_at | TUBB2A | 684 | $5.82\ 10^{-2}$ | 1.30 | Down-regulated |
| 7 | 213790_at | ADAM12 | 74 | $2.53\ 10^{-3}$ | 1.13 | Up-regulated |
| 8 | 226736_at | CHURC1 | 124 | $5.54\ 10^{-4}$ | 1.26 | Up-regulated |
| 9 | 230720_at | RNF182 | 49 | $3.52\ 10^{-3}$ | 1.58 | Up-regulated |

TABLE 3-continued

| SEQ ID NOs: | Affymetrix probeset | Abbreviated name | Mean signal | P-value | Fold change | Expression in BC versus BBD |
|---|---|---|---|---|---|---|
| 10-13 | 220532_at | TMEM176B | 97 | $1.70\ 10^{-2}$ | 1.21 | Up-regulated |
| 14-15 | 219629_at | FAM118A | 100 | $1.49\ 10^{-1}$ | 1.12 | Up-regulated |
| 16 | 156960_s_at | ANKRD20A | 70 | $7.80\ 10^{-2}$ | 1.11 | Down-regulated |
| 17-19 | 206785_s_at | KLRC1/2 | 93 | $4.87\ 10^{-2}$ | 1.15 | Down-regulated |
| 20 | 225525_at | KIAA1671 | 69 | $1.75\ 10^{-2}$ | 1.12 | Up-regulated |
| 21 | 1554469_at | ZBTB44 | 58 | $2.16\ 10^{-3}$ | 1.13 | Down-regulated |
| 22-23 | 235126_at | LQK1 | 83 | $2.66\ 10^{-2}$ | 1.14 | Up-regulated |
| 24-25 | 210873_x_at | APOBEC3A | 335 | $3.52\ 10^{-1}$ | 1.12 | Down-regulated |
| 26 | 229187_at | LOC283788 | 94 | $1.91\ 10^{-1}$ | 1.08 | Up-regulated |
| 27 | 1559140_at | FAM87A/B | 68 | $2.32\ 10^{-2}$ | 1.09 | Up-regulated |
| 28 | 242770_at | LOC642236 | 49 | $2.35\ 10^{-2}$ | 1.14 | Up-regulated |
| 29 | 214428_x_at | C4A/B | 55 | $4.77\ 10^{-2}$ | 1.11 | Down-regulated |
| 30 | 1554094_at | ENTPD5 | 87 | $4.70\ 10^{-5}$ | 1.11 | Down-regulated |
| 31 | 215610_at | LOC728263 | 89 | $2.03\ 10^{-3}$ | 1.09 | Up-regulated |
| 32 | 1553623_at | MGC15705 | 79 | $2.57\ 10^{-2}$ | 1.08 | Down-regulated |
| 33-34 | 242687_at | FAM160A1 | 50 | $2.48\ 10^{-2}$ | 1.08 | Up-regulated |
| 35 | 219700_at | PLXDC1 | 107 | $3.82\ 10^{-3}$ | 1.14 | Down-regulated |
| 36 | 33323_r_at | SFN | 54 | $1.26\ 10^{-1}$ | 1.09 | Down-regulated |
| 37-39 | 208791_at | CLU | 112 | $2.37\ 10^{-1}$ | 1.08 | Up-regulated |
| 40-42 | 205048_s_at | PSPH | 68 | $4.18\ 10^{-1}$ | 1.06 | Down-regulated |
| 43-44 | 212999-_x_at | HLA-DQB1 | 120 | $1.00\ 10^{-1}$ | 1.23 | Down-regulated |

4-Genes Signature

In a first training set, the 4-gene panel CHI3L1, CLEC4C, LILRA3 and TUBB2A was classified malignant and benign with an estimated accuracy of 71% (76% sensitivity and 66% specificity).

Of the 79 breast cancer samples, 60 were classified correctly, while 48 of the 73 benign samples were assigned to the correct class (Table 4a).

TABLE 4a

Classification value for the identified signature on Training Dataset

| Training set | | Prediction outcome | |
|---|---|---|---|
| | | BBD | BC |
| Pathological diagnosis | BBD | 48 | 25 |
| | BC | 19 | 60 |

Accuracy = 71%, Sensitivity = 76%, Specificity = 66%

The metric performance of the model in the independent BI-RADS 0 test set was reported in Table 4b. Three of the five cancer samples were correctly classified, while 8 out of 21 benign patients were accurately classified, with a sensitivity of 60% and specificity of 38% respectively. The accuracy of the model in the test set of BI-RADS 0 is 42%.

TABLE 4b

Classification value for the identified signature on Independent Test Dataset

| Training set | | Prediction outcome | |
|---|---|---|---|
| | | BBD | BC |
| Pathological diagnosis | BBD | 8 | 13 |
| | BC | 2 | 3 |

Accuracy = 42%, Sensitivity = 60%, Specificity = 38%

28-Genes Signature

In the training set, the 28-gene panel was classified malignant and benign with an estimated accuracy of 88% (94% sensitivity and 84% specificity).

Of the 79 breast cancer samples, 74 were classified correctly, while 61 of the 73 benign samples were assigned to the correct class (Table 5a).

TABLE 5a

Classification value for the identified signature on Training Dataset

| Training set | | Prediction outcome | |
|---|---|---|---|
| | | BBD | BC |
| Pathological diagnosis | BBD | 61 | 12 |
| | BC | 5 | 74 |

Accuracy = 88%, Sensitivity = 94%, Specificity = 84%

The metric performance of the model in the independent BI-RADS 0 test set was reported in Table 5b. Four of the five cancer samples were correctly classified, while 15 out of 21 benign patients were accurately classified, with a sensitivity of 80% and specificity of 71% respectively. The accuracy of the model in the test set of BI-RADS 0 is 73%.

TABLE 5b

Classification value for the identified signature on Independent Test Dataset

| Training set | | Prediction outcome | |
|---|---|---|---|
| | | BBD | BC |
| Pathological diagnosis | BBD | 15 | 6 |
| | BC | 1 | 4 |

Accuracy = 73%, Sensitivity = 80%, Specificity = 71%

The inventors have also analyzed whether any of the clinical characteristics were significantly overrepresented among the subjects incorrectly predicted. They found that the only false negative case in the test set was a 46 years old woman who had Paget's disease and DCIS.

BIBLIOGRAPHIC REFERENCES

1. Margaret M. Eberl, M P H, Chester H. Fox, Stephen B. Edge, Cathleen A. Carter, and Martin C. Mahoney. BI-RADS Classification for Management of Abnormal Mammograms, The Journal of the American Board of Family Medicine 19:161-1
2. Whitney A R, Diehn M, Popper S J, Alizadeh A A, Boldrick J C, Relman D A, Brown P O. Individuality and variation in gene expression patterns in human blood. Proc Natl Acad Sci USA. 2003, 18;100(4):1896-901.
  3. P. E. Nielsen et al, Science, 254, 1497-1500 (1991).
  4. Kricka et al., Clinical Chemistry, 1999, no 45 (4), p. 453-458.
  5. Keller G. H. et al., DNA Probes, 2nd Ed., Stockton Press, 1993, sections 5 and 6, p. 173-249.
  6. Tyagi & Kramer, Nature Biotech, 1996, 14:303-308.
  7. M. Chee et al., Science, 1996, 274, 610-614].
  8. A. Caviani Pease et al., Proc. Natl. Acad. Sci. USA, 1994, 91, 5022-5026.
  9. G. Ramsay, Nature Biotechnology, 1998, No. 16, p. 40-44.
  10. F. Ginot, Human Mutation, 1997, No. 10, p. 1-10.
  11. J. Cheng et al, Molecular diagnosis, 1996, No. 1 (3), p. 183-200.
  12. T. Livache et al, Nucleic Acids Research, 1994, No. 22 (15), p. 2915-2921.
  13. J. Cheng et al, Nature Biotechnology, 1998, No. 16, p. 541-546.
  14. Harris Drucker, Chris J. C. Burges, Linda Kaufman, Alex Smola and Vladimir Vapnik (1997). "Support Vector Regression Machines". Advances in Neural Information Processing Systems 9, NIPS 1996, 155-161, MIT Press.
  15. R Development Core Team (2009). R: A language and environment for statistical computing. R Foundation for Statistical Computing, Vienna, Austria. ISBN 3-900051-07-0, URL www.R-project.org
  16. Gentleman R C, Carey V J, Bates D M, Bolstad B, Dettling M, Dudoit S, Ellis B, Gautier L, Ge Y, Gentry J, et al.: Bioconductor: open software development for computational biology and bioinformatics.
  17. Crispin J Miller. simpleaffy (2009): Very simple high level analysis of Affymetrix data. R package version 2.22.0. www.bioconductor.org, bioinformatics.picr.man.ac.uk/simpleaffy/
  18. R. Gentleman, V. Carey, W. Huber and F. Hahne (2009). genefilter: genefilter: methods for filtering genes from microarray experiments. R package version 1.28.0.

The invention claimed is:

1. A method comprising the following steps:
   a) obtaining a biological sample comprising mRNA from a patient and optionally reverse transcribing the mRNA to produce cDNA,
   b) contacting the mRNA or the cDNA from the biological sample with at least four reagents, each reagent comprising at least one oligonucleotide respectively specific for each of at least four different target genes, wherein the at least four reagents comprise reagents specific for no more than 28 target genes, the no more than 28 target genes selected from the group consisting of genes respectively comprising the full length nucleic acid sequences set forth in SEQ ID NO: 1 to 44, and the at least four reagents being specific for at least four different target genes that comprise the full length nucleic acid sequences set forth in:
   1) SEQ ID NO: 1 and
   2) SEQ ID NO: 2 or 3; and
   3) SEQ ID NO: 4; and
   4) SEQ ID NO: 5 or 6; and
   c) measuring an expression level for each of the at least four target genes to obtain an expression profile for the patient.

2. The method as claimed in claim 1, wherein in step b) the mRNA or cDNA is brought into contact with reagents specific for a combination of 28 target genes, and the expression level of the 28 genes is measured in step c) to obtain the expression profile for the patient.

3. The method as claimed in claim 1, wherein the biological sample taken from the patient is a blood sample.

4. The method as claimed in claim 1, wherein each of the specific reagents of step b) comprises at least one hybridization probe.

5. The method as claimed in claim 4, wherein each of the specific reagents of step b) further comprises at least one primer.

6. The method as claimed in claim 5, wherein each of the reagents specific for a target gene of step b) comprises one hybridization probe and two primers.

7. A kit comprising at least four reagents, each reagent comprising at least one oligonucleotide respectively specific for each of at least four different target genes, wherein the at least four reagents comprise reagents specific for no more than 28 target genes, the no more than 28 target genes selected from the group consisting of genes respectively comprising the full length nucleic acid sequences set forth in SEQ ID NO: 1 to 44, and the at least four reagents being specific for at least four different target genes that comprise the full length nucleic acid sequences set forth in:
   1) SEQ ID NO: 1 and
   2) SEQ ID NO: 2 or 3; and
   3) SEQ ID NO: 4; and
   4) SEQ ID NO: 5 or 6, and
   wherein at least one oligonucleotide has a detectable label directly attached thereto or wherein the oligonucleotides are immobilized to a solid substrate.

8. The kit as claimed in claim 7, comprising reagents specific for a combination of 28 target genes.

9. A method comprising manufacturing the kit of claim 7.

10. A method comprising manufacturing the kit of claim 8.

11. The method as claimed in claim 9, wherein each of the reagents comprises at least one hybridization probe.

12. The method as claimed in claim 11, wherein each of the reagents further comprises at least one primer.

13. The method as claimed in claim 12, wherein each of the reagents comprises one hybridization probe and two primers.

* * * * *

SEQUENCE LISTING

```
<160> NUMBER OF SEQ ID NOS: 44

<210> SEQ ID NO 1
<211> LENGTH: 1792
<212> TYPE: DNA
<213> ORGANISM: Homo sapiens

<400> SEQUENCE: 1
agtggagtgg gacaggtata taaaggaagt acagggcctg gggaagaggc cctgtctagg      60
tagctggcac caggagccgt gggcaaggga agaggccaca ccctgccctg ctctgctgca     120
gccagaatgg gtgtgaaggc gtctcaaaca ggctttgtgg tcctggtgct gctccagtgc     180
tgctctgcat acaaactggt ctgctactac accagctggt cccagtaccg ggaaggcgat     240
gggagctgct tcccagatgc ccttgaccgc ttcctctgta cccacatcat ctacagcttt     300
gccaatataa gcaacgatca catcgacacc tgggagtgga tgatgtgac  gctctacggc     360 atgctcaaca cactcaagaa caggaacccc aacctgaaga ctctcttgtc tgtcggagga     420
tggaactttg gtctcaaag attttccaag atagcctcca cacccagag tcgccggact      480 ttcatcaagt cagtaccgcc atttctgcgc acccatggct ttgatgggct ggaccttgcc     540
tggctctacc ctggacggag agacaaacag cattttacca ccctaatcaa ggaaatgaag     600
gccgaattta taaaggaagc ccagccaggg aaaaagcagc tcctgctcag cgcagcactg     660
tctgcgggga aggtcaccat tgacagcagc tatgacattg ccaagatatc ccaacacctg     720
gatttcatta gcatcatgac ctacgatttt catggagcct ggcgtgggac cacaggccat     780
cacagtcccc tgttccgagg tcaggaggat gcaagtcctg acagattcag caacactgac     840
tatgctgtgg ggtacatgtt gaggctgggg gctcctgcca gtaagctggt gatgggcatc     900
cccaccttcg ggaggagctt cactctggct tcttctgaga ctggtgttgg agccccaatc     960
tcaggaccgg gaattccagg ccggttcacc aaggaggcag ggaccccttgc ctactatgag    1020 atctgtgact tcctccgcgg agccacagtc catagaatcc tcggccagca ggtcccctat    1080
gccaccaagg gcaaccagtg ggtaggatac gacgaccagg aaagcgtcaa aagcaaggtg    1140
cagtacctga aggacaggca gctggcgggc gccatggtat gggcctgga cctggatgac    1200 ttccagggct ccttctgtgg ccaggatctg cgcttccctc tcaccaatgc catcaaggat    1260
gcactcgctg caacgtagcc ctctgttctg cacacagcac ggggggccaag gatgccccgt    1320
```

```
cccccctctgg ctccagctgg ccgggagcct gatcacctgc cctgctgagt cccaggctga    1380
gcctcagtct ccctcccttg gggcctatgc agaggtccac aacacacaga tttgagctca    1440
gccctggtgg gcagagaggt agggatgggg ctgtggggat agtgaggcat cgcaatgtaa    1500
gactcgggat tagtacacac ttgttgatta atggaaatgt ttacagatcc ccaagcctgg    1560
caagggaatt tcttcaactc cctgcccccc agccctcctt atcaaggac  accattttgg    1620 caagctctat caccaaggag ccaaacatcc tacaagacac agtgaccata ctaattatac    1680 ccccctgcaaa gcccagcttg aaaccttcac ttaggaacgt aatcgtgtcc cctatcctac   1740
ttccccttcc taattccaca gctgctcaat aaagtacaag agcttaacag tg            1792

<210> SEQ ID NO 2
<211> LENGTH: 922
<212> TYPE: DNA
<213> ORGANISM: Homo sapiens

<400> SEQUENCE: 2
aattgaaagc tttagctcac tgcagagtct cctaagtcac atctcttcct ttgcaagagt     60
aggcgaagaa ggatctaagg gcttggcttg tttgaaagaa ccacaccccg aaagtaacat    120
ctttggagaa agtgatacaa gagcttctgc acccacctga tagaggaagt ccaaagggtg    180
tgcgcacaca caatggtgcc tgaagaagag cctcaagacc gagtgcctca caattttatg    240
tatagcaaaa ctgtcaagag gctgtccaag ttacgagagt atcaacagta tcatccaagc    300
ctgacctgcg tcatggaagg aaaggacata gaagattgga gctgctgccc aaccccttgg    360
acttcatttc agtctagttg ctactttatt tctactggga tgcaatcttg gactaagagt    420
caaaagaact gttctgtgat gggggctgat ctggtggtga tcaacaccag ggaagaacag    480
gatttcatca ttcagaatct gaaaagaaat tcttcttatt ttctggggct gtcagatcca    540
gggggtcggc gacattggca atgggttgac cagacaccat acaatgaaaa tgtcacattc    600
tggcactcag gtgaacccaa taaccttgat gagcgttgtg cgataataaa tttccgttct    660
tcagaagaat ggggctggaa tgacattcac tgtcatgtac ctcagaagtc aatttgcaag    720
atgaagaaga tctacatata aatgaaatat tctccctgga aatgtgtttg ggttggcatc    780
caccgttgta gaaagctaaa ttgatttttt aatttatgtg taagttttgt acaaggaatg    840
cccctaaaat gtttcagcag gctgtcacct attcacttta tgatataatc cattcacaca    900
ttcatttatt catttattca tt                                             922

<210> SEQ ID NO 3
<211> LENGTH: 1015
<212> TYPE: DNA
<213> ORGANISM: Homo sapiens

<400> SEQUENCE: 3
aattgaaagc tttagctcac tgcagagtct cctaagtcac atctcttcct ttgcaagagt     60
aggcgaagaa ggatctaagg gcttggcttg tttgaaagaa ccacaccccg aaagtaacat    120
ctttggagaa agtgatacaa gagcttctgc acccacctga tagaggaagt ccaaagggtg    180
tgcgcacaca caatggtgcc tgaagaagag cctcaagacc gagagaaagg actctggtgg    240
ttccagttga aggtctggtc catggcagtc gtatccatct tgctcctcag tgtctgtttc    300
actgtgagtt ctgtggtgcc tcacaatttt atgtatagca aaactgtcaa gaggctgtcc    360
aagttacgag agtatcaaca gtatcatcca agcctgacct gcgtcatgga aggaaaggac    420
```

-continued

| | |
|---|---|
| atagaagatt ggagctgctg cccaacccct tggacttcat ttcagtctag ttgctacttt | 480 |
| atttctactg ggatgcaatc ttggactaag agtcaaaaga actgttctgt gatgggggct | 540 |
| gatctggtgg tgatcaacac cagggaagaa caggatttca tcattcagaa tctgaaaaga | 600 |
| aattcttctt attttctggg gctgtcagat ccagggggtc ggcgacattg gcaatgggtt | 660 |
| gaccagacac catacaatga aaatgtcaca ttctggcact caggtgaacc caataacctt | 720 |
| gatgagcgtt gtgcgataat aaatttccgt tcttcagaag aatggggctg gaatgacatt | 780 |
| cactgtcatg tacctcagaa gtcaatttgc aagatgaaga agatctacat ataaatgaaa | 840 |
| tattctccct ggaaatgtgt ttgggttggc atccaccgtt gtagaaagct aaattgattt | 900 |
| tttaatttat gtgtaagttt tgtacaagga atgcccctaa aatgtttcag caggctgtca | 960 |
| cctattacac ttatgatata atccattcac acattcattt attcatttat tcatt | 1015 |

<210> SEQ ID NO 4
<211> LENGTH: 1604
<212> TYPE: DNA
<213> ORGANISM: Homo sapiens

<400> SEQUENCE: 4

| | |
|---|---|
| gagcctccaa gtgtccacac cctgtgtgtc ctctgtcctg ccagcaccga gggctcatcc | 60 |
| atccacagag cagtgcagtg ggaggagacg ccatgacccc catcctcacg gtcctgatct | 120 |
| gtctcgggct gagcctggac cccaggaccc acgtgcaggc agggcccctc cccaagccca | 180 |
| ccctctgggc tgagccaggc tctgtgatca cccaagggag tcctgtgacc ctcaggtgtc | 240 |
| aggggagcct ggagacgcag gagtaccatc tatatagaga aaagaaaaca gcactctgga | 300 |
| ttacacggat cccacaggag cttgtgaaga agggccagtt ccccatccta tccatcacct | 360 |
| gggaacatgc agggcggtat tgctgtatct atggcagcca cactgcaggc ctctcagaga | 420 |
| gcagtgaccc cctggagctg gtggtgacag agcctacag caaacccacc ctctcagctc | 480 |
| tgcccagccc tgtggtgacc tcaggaggga atgtgaccat ccagtgtgac tcacaggtgg | 540 |
| catttgatgg cttcattctg tgtaaggaag agaagatga acacccacaa tgcctgaact | 600 |
| cccattccca tgcccgtggg tcatcccggg ccatcttctc cgtgggcccc gtgagcccaa | 660 |
| gtcgcaggtg gtcgtacagg tgctatggtt atgactcgcg cgctccctat gtgtggtctc | 720 |
| tacccagtga tctcctgggg ctcctggtcc caggtgtttc taagaagcca tcactctcag | 780 |
| tgcagccggg tcctgtcgtg gcccctgggg agaagctgac cttccagtgt ggctctgatg | 840 |
| ccggctacga cagatttgtt ctgtacaagg agtggggacg tgacttcctc cagcgccctg | 900 |
| gccggcagcc ccaggctggg ctctcccagg ccaacttcac cctgggccct gtgagccgct | 960 |
| cctacggggg ccagtacaca tgctccggtg catacaacct ctcctccgag tggtcggccc | 1020 |
| ccagcgaccc cctggacatc ctgatcacag gacagatccg tgccagaccc ttcctctccg | 1080 |
| tgcggccggg ccccacagtg gcctcaggag agaacgtgac cctgctgtgt cagtcacagg | 1140 |
| gagggatgca cactttcctt ttgaccaagg aggggcagc tgattcccg ctgcgtctaa | 1200 |
| aatcaaagcg ccaatctcat aagtaccagg ctgaattccc catgagtcct gtgacctcgg | 1260 |
| cccacgcggg gacctacagg tgctacggct cactcagctc caacccctac ctgctgactc | 1320 |
| accccagtga ccccctggag ctcgtggtct caggagcagc tgagaccctc agcccaccac | 1380 |
| aaaacaagtc cgactccaag gctggtgagt gaggagatgc ttgccgtgat gacgctgggc | 1440 |
| acagagggtc aggtcctgtc aagaggagct gggtgtcctg ggtggacatt tgaagaatta | 1500 |
| tattcattcc aacttgaaga attattcaac acctttaaca atgtatatgt gaagtacttt | 1560 | attctttcat attttaaaaa taaaagataa ttatccatga gaaa    1604

<210> SEQ ID NO 5
<211> LENGTH: 1998
<212> TYPE: DNA
<213> ORGANISM: Homo sapiens

<400> SEQUENCE: 5

| | |
|---|---|
| gggggctcg gctgggggc gcggcctgtg ccggccgccc caccctcctt gcataaaagc | 60 |
| cggagcccgc ggggccggcg ctctcagccc gtcggttccc gagcgccttc ccggtgaccc | 120 |
| cgcagtgggt gtgtgagggg aggacggaca gacccagacg ccgccggacc aggaggacgc | 180 |
| tgacgaggca ccatgcgtga gatcgtgcac atccaggcgg gccagtgcgg caaccagatc | 240 |
| ggcgccaagt tttgggaggt catcagtgat gagcatggga ttgaccccac tggcagttac | 300 |
| catggagaca gtgatttgca gctggagaga atcaatgttt actacaatga agccactggt | 360 |
| aacaaatatg ttcctcgggc catcctcgtg gatctggagc caggcacgat ggattcggtt | 420 |
| aggtctggac cattcggcca gatcttcaga ccagacaatt tcgtgtttgg ccagagtgga | 480 |
| gccgggaata actgggccaa gggccactac acagagggag ccgagctggt cgactcggtc | 540 |
| ctggatgtgg tgaggaagga gtcagagagc tgtgactgtc tccagggctt ccagctgacc | 600 |
| cactctctgg ggggcggcac ggggtccggg atgggcaccc tgctcatcag caagatccgg | 660 |
| gaagagtacc cagaccgcat catgaacacc ttcagcgtca tgccctcacc caaggtgtca | 720 |
| gacacggtgg tggagcccta caacgccacc ctctccggtcc accagctggt ggaaaacaca | 780 |
| gatgaaacct actgcattga aacgaggcc ctgtatgaca tctgcttccg caccctgaag | 840 |
| ctgaccaccc ccacctacgg ggacctcaac cacctggtgt cggccaccat gagcggggtc | 900 |
| accacctgcc tgcgcttccc gggccagctg aacgcagacc tgcgcaagct ggcggtgaac | 960 |
| atggtgccct tccctcgcct gcacttcttc atgcccggct tcgcgcccct gaccagccgg | 1020 |
| ggcagccagc agtaccgggc gctcacggtg cccgagctca cccagcagat gttcgactcc | 1080 |
| aagaacatga tggccgcctg cgacccgcgc cacggccgct acctgacggt ggctgccatc | 1140 |
| ttccggggcc gcatgtccat gaaggaggtg gacgagcaga tgctcaacgt gcagaacaag | 1200 |
| aacagcagct acttcgtgga gtggatcccc aacaacgtga agacggccgt gtgcgacatc | 1260 |
| ccgcccgcg gcctgaagat gtcggccacc ttcatcggca acagcacggc catccaggag | 1320 |
| ctgttcaagc gcatctccga gcagttcacg gccatgttcc ggcgcaaggc cttcctgcac | 1380 |
| tggtacacgg gcgagggcat ggacgagatg gagttcaccg aggccgagag caacatgaac | 1440 |
| gacctggtgt ccgagtacca gcagtaccag gacgccacgg ccgacgaaca aggggagttc | 1500 |
| gaggaggagg agggcgagga cgaggcgtag atgcccccgc gagacgggtt agggaaagcg | 1560 |
| gaggaggaaa gcgaggggt gggggcttc ccgggacgat aacctggcag tggaaggaaa | 1620 |
| gaagcatggc ctactttagg tgtgcgctgg gtctctggtg ctcttcactg ttgcctgtca | 1680 |
| cttttttttt cctttttttgt aatattgatg acatcaatgt aacatttgag atatttctga | 1740 |
| attactgttg taatggctaa atcacataa acgtttgtgt cggaatggtg tcctctcttt | 1800 |
| ctcttccttt ttctctttat taacgattta aatgtaactt tctgaacaca ttgcattgaa | 1860 |
| ttcttccttt aacaaaaagc aaaggcgtag gtaaaagctc aaatgaattt attctttcgg | 1920 |
| tatggtaaaa ttgaaccaat cacagttaag atgagagatc aacctgagtt ttaaaatacc | 1980 |
| tttaataaat attagttg | 1998 |

<210> SEQ ID NO 6
<211> LENGTH: 1595
<212> TYPE: DNA
<213> ORGANISM: Homo sapiens

<400> SEQUENCE: 6

```
gcccgccggt ccacgccgcg caccgctccg agggccagcg ccacccgctc cgcagccggc      60
accatgcgcg agatcgtgca catccaggcg ggccagtgcg gcaaccagat cggcgccaag     120
ttttgggagg tcatcagcga tgagcatggg atcgacccca caggcagtta ccatggagac     180
agtgacttgc agctggagag aatcaacgtg tactacaatg aggctgctgg taacaaatat     240
gtacctcggg ccatcctggt ggatctggag cctggcacca tggactctgt caggtctgga     300
cccttcggcc agatcttcag accagacaac ttcgtgttcg ccagagtgg agccgggaat     360
aactgggcca agggccacta cacagaggga gccgagctgg tcgactcggt cctggatgtg     420
gtgaggaagg agtcagagag ctgtgactgt ctccagggct ccagctgac ccactctctg     480
gggggcggca cggggtccgg gatgggcacc ctgctcatca gcaagatccg ggaagagtac     540
ccagaccgca tcatgaacac cttcagcgtc atgccctcac ccaaggtgtc agacacggtg     600
gtggagcccc acaacgccac cctctctgtc caccagctgg tggaaaacac agatgaaacc     660
tactccattg ataacgaggc cctgtatgac atctgcttcc gcaccctgaa gctgaccacc     720
cccacctacg gggacctcaa ccacctggtg tcggccacca tgagcggggt caccacctgc     780
ctgcgcttcc cgggccagct gaacgcagac ctgcgcaagc tggcggtgaa catggtgccc     840
ttccctcgcc tgcacttctt catgcccggc ttcgcgcccc tgaccagccg gggcagccag     900
cagtaccggg cgctcacggt gcccgagctc acccagcaga tgttcgactc caagaacatg     960
atggccgcct cgaccccgcg ccacggccgc tacctgacgg tggctgccat cttccggggc    1020
cgcatgtcca tgaaggaggt ggacgagcag atgctcaacg tgcagaacaa gaacagcagc    1080
tacttcgtgg agtggatccc caacaacgtg aagacggccg tgtgcgacat cccgcccgc    1140
ggcctgaaga tgtcggccac cttcatcggc aacagcacgg ccatccagga gctgttcaag    1200
cgcatctccg agcagttcac ggccatgttc cggcgcaagg ccttcctgca ctggtacacg    1260
ggcgagggca tggacgagat ggagttcacc gaggccgaga gcaacatgaa cgacctggtg    1320
tccgagtacc agcagtacca ggacgccacg gccgacgaac aagggagtt cgaggaggag    1380
gagggcgagg acgaggctta aaaacttctc agatcaatcg tgcatcctta gtgaacttct    1440
gttgtcctca agcatggtct ttctacttgt aaactatggt gctcagtttt gcctctgtta    1500
gaaattcaca ctgttgatgt aatgatgtgg aactcctcta aaaattacag tattgtctgt    1560
gaaggtatct atactaataa aaaagcatgt gtaga                                1595
```

<210> SEQ ID NO 7
<211> LENGTH: 3313
<212> TYPE: DNA
<213> ORGANISM: Homo sapiens

<400> SEQUENCE: 7

```
cactaacgct cttcctagtc cccgggccaa ctcggacagt ttgctcattt attgcaacgg      60
tcaaggctgg cttgtgccag aacggcgcgc gcgcgcgcac gcacgcacac acacgggggg     120
aaactttttt aaaaatgaaa ggctagaaga gctcagcggc ggcgcgggcg ctgcgcgagg     180
gctccggagc tgactcgccg aggcaggaaa tccctccggt cgcgacgccc ggccccggct     240
cggcgcccgc gtgggatggt gcagcgctcg ccgccgggcc cgagagctgc tgcactgaag     300
```

-continued

```
gccggcgacg atggcagcgc gcccgctgcc cgtgtccccc gcccgcgccc tcctgctcgc    360
cctggccggt gctctgctcg cgccctgcga ggcccgaggg gtgagcttat ggaaccaagg    420
aagagctgat gaagttgtca gtgcctctgt tgggagtggg gacctctgga tcccagtgaa    480
gagcttcgac tccaagaatc atccagaagt gctgaatatt cgactacaac gggaaagcaa    540
agaactgatc ataaatctgg aaagaaatga aggtctcatt gccagcagtt tcacggaaac    600
ccactatctg caagacggta ctgatgtctc cctcgctcga aattacacgg taattctggg    660
tcactgttac taccatggac atgtacgggg atattctgat tcagcagtca gtctcagcac    720
gtgttctggt ctcaggggac ttattgtgtt tgaaaatgaa agctatgtct tagaaccaat    780
gaaaagtgca accaacagat acaaactctt cccagcgaag aagctgaaaa gcgtccgggg    840
atcatgtgga tcacatcaca acacaccaaa cctcgctgca agaatgtgt tccaccacc      900 ctctcagaca tgggcaagaa ggcataaaag agagaccctc aaggcaacta agtatgtgga    960
gctggtgatc gtggcagaca accgagagtt cagaggcaa ggaaaagatc tggaaaaagt    1020
taagcagcga ttaatagaga ttgctaatca cgttgacaag ttttacagac cactgaacat    1080
tcggatcgtg ttggtaggcg tggaagtgtg gaatgacatg gacaaatgct ctgtaagtca    1140
ggacccattc accagcctcc atgaatttct ggactggagg aagatgaagc ttctacctcg    1200
caaatcccat gacaatgcgc agcttgtcag tggggtttat ttccaaggga ccaccatcgg    1260
catggcccca atcatgagca tgtgcacggc agaccagtct ggggggaattg tcatggacca    1320 ttcagacaat ccccttggtg cagccgtgac cctggcacat gagctgggcc acaatttcgg    1380
gatgaatcat gacacactgg acaggggctg tagctgtcaa atggcggttg agaaaggagg    1440
ctgcatcatg aacgcttcca ccgggtaccc atttcccatg gtgttcagca gttgcagcag    1500
gaaggacttg gagaccagcc tggagaaagg aatgggggtg tgcctgttta acctgccgga    1560
agtcagggag tctttcgggg gccagaagtg tgggaacaga tttgtggaag aaggagagga    1620
gtgtgactgt ggggagccag aggaatgtat gaatcgctgc tgcaatgcca ccacctgtac    1680
cctgaagccg gacgctgtgt gcgcacatgg gctgtgctgt gaagactgcc agctgaagcc    1740
tgcaggaaca gcgtgcaggg actccagcaa ctcctgtgac ctcccagagt tctgcacagg    1800
ggccagccct cactgcccag ccaacgtgta cctgcacgat gggcactcat gtcaggatgt    1860
ggacggctac tgctacaatg gcatctgcca gactcacgag cagcagtgtg tcacgctctg    1920
gggaccaggt gctaaacctg cccctgggat ctgctttgag agagtcaatt ctgcaggtga    1980
tccttatggc aactgtggca aagtctcgaa gagttccttt gccaaatgcg agatgagaga    2040
tgctaaatgt ggaaaaatcc agtgtcaagg aggtgccagc cggccagtca ttggtaccaa    2100 tgccgttttcc atagaaacaa acatcccct gcagcaagga ggccggattc tgtgccgggg    2160
gacccacgtg tacttgggcg atgacatgcc ggacccaggg cttgtgcttg caggcacaaa    2220
gtgtgcagat ggaaaaatct gcctgaatcg tcaatgtcaa atattagtg tctttgggt    2280 tcacgagtgt gcaatgcagt gccacggcag aggggtgtgc aacaacagga agaactgcca    2340
ctgcgaggcc cactgggcac ctcccttctg tgacaagttt ggctttggag aagcacaga    2400 cagcggcccc atccggcaag cagaagcaag gcaggaagct gcagagtcca acagggagcg    2460
cggccagggc caggagcccg tgggatcgca ggagcatgcg tctactgcct cactgacact    2520
catctgagcc ctcccatgac atggagaccg tgaccagtgc tgctgcagag gaggtcacgc    2580
gtccccaagg cctcctgtga ctggcagcat tgactctgtg gctttgccat cgtttccatg    2640
```

| | |
|---|---|
| acaacagaca caacacagtt ctcggggctc aggaggggaa gtccagccta ccaggcacgt | 2700 |
| ctgcagaaac agtgcaagga agggcagcga cttcctggtt gagcttctgc taaaacatgg | 2760 |
| acatgcttca gtgctgctcc tgagagagta gcaggttacc actctggcag gccccagccc | 2820 |
| tgcagcaagg aggaagagga ctcaaaagtc tggcctttca ctgagcctcc acagcagtgg | 2880 |
| gggagaagca agggttgggc ccagtgtccc ctttccccag tgacacctca gccttggcag | 2940 |
| ccctgatgac tggtctctgg ctgcaactta atgctctgat atggctttta gcatttatta | 3000 |
| tatgaaaata gcagggtttt agtttttaat ttatcagaga ccctgccacc cattccatct | 3060 |
| ccatccaagc aaactgaatg gcaatgaaac aaactggaga agaaggtagg agaaagggcg | 3120 |
| gtgaactctg gctcttttgct gtggacatgc gtgaccagca gtactcaggt ttgagggttt | 3180 |
| gcagaaagcc agggaaccca cagagtcacc aacccttcat ttaacaagta agaatgttaa | 3240 |
| aaagtgaaaa caatgtaaga gcctaactcc atccccgtg gccattactg cataaaatag | 3300 |
| agtgcatttg aaa | 3313 |

<210> SEQ ID NO 8
<211> LENGTH: 3381
<212> TYPE: DNA
<213> ORGANISM: Homo sapiens

<400> SEQUENCE: 8

| | |
|---|---|
| aaccgtatct cagttctcgc gaggtttcgt cttcccggaa gcgttggagg acattccctg | 60 |
| ttgactgcgt cgcgatgtgt ggcgactgtg tggagaagga atatcccaac cggggtaata | 120 |
| cctgcctgga gaatggatct ttcttactga actttacagg ctgtgcagtg tgcagtaagc | 180 |
| gggattttat gctgatcaca aacaaatcct tgaaagaaga agatggagaa gaaatagtta | 240 |
| cctatgatcc agatttgtgt aagaattgtc atcatgtaat agccagacat gagtatacat | 300 |
| tcagtatcat ggatgaattt caggagtata ccatgctgtg tctgttatgc ggcaaagccg | 360 |
| aagatactat cagtattctc cctgatgacc cccgacaaat gactctctta ttctaaggat | 420 |
| ccttctacag atctgttata actatattgt gttggtttac aatacagcaa gcctgatggt | 480 |
| ttgtcttatt tcattcatac tgaaaattct ttgcatattt tttttctgct tagacttact | 540 |
| tattctttga ggaaaaaagg taatgtagga gctcattgtt ctctagagct gagctcttct | 600 |
| gctaaagttc aaagttcaca tcagtgtagc cagagtgaag catctttgtt agcagttatg | 660 |
| tggtcagaaa acaactagaa tgggagcaca cctggtgccc agattttggt ttccaataaa | 720 |
| aggaaccagg actccttaga aaatgaactg attctagaac tgggatatga actgtacaag | 780 |
| atgagcctag agtatcttgt gccacagaaa aatgaagtac tgaaattaaa aaaaaaaat | 840 |
| catagtgatt gggagtatgt cagcatgatc gaactgaagg atctctgaaa ggccacagct | 900 |
| ggagcaattt gagtaacaaa ataaagtagt attgggttat aacccaaact atataataaa | 960 |
| tatttacaag cccaaactaa tataaatgat tgaatgggaa caaatctctt gtgcagaaga | 1020 |
| atttcaaata atttatgtag atactcccca cttagtgggc tctgcatagt gacttccttg | 1080 |
| cagagtataa tatggaaagg ggggaaaaga gtaactttac agtggagaaa tctgacagac | 1140 |
| accagctcag ccaggtgatt gaggttaaca tcatccatga taagcccttt tgatagcatg | 1200 |
| tatccttgat agcatcacat catacagaat gtgataagaa tggcacttta cctctgtggt | 1260 |
| cctcctcccc agaactcaga acccaagtct gatcaggaga aaacatcac acaaattcca | 1320 |
| attgagaagc attcttttaaa atacctaacc agtacttctc aaaactatca aggccataaa | 1380 |
| aaacaaggaa aatctgagac atggtcacag ccaagaggag cctgagaaga catgactgct | 1440 |

```
agatgtaatg tggtatccta catggaatta tataccacga aaagaaaaaa aggtcatttg    1500
gtagaaacta gggaaatctg aatacagtgt ggacttcagt taatataaat gagaaaatgg    1560
tttcattggc tttaaaggga ttttagaata tcttactttg catagtttca tgagcactgg    1620
ccaggaggtt ataaactggc atttaggcct ctctgccatt tagtagcagt atagtcatta    1680
agcaaagcat tactctggac tttattgtcc tgtttctatc aaattggact aacaaaaatt    1740
gatataatac attcatcaca gtattgttag gagatttaaa tgaattagtg aatgtaagat    1800
actttagaaa gcatgtaaag tactagaaac aatgaggtgg cttcaattag tgctcattct    1860
gagacctaaa tttaaagggt caggcattag aaacaaaagt gtttcttcat atctaggaga    1920
tttggaaatt ctgaactaag gtcttataag aacaagaaat gagcaaagtg ttcattgtag    1980
atactaggga aaagctttgt tgaataacag taatgatgat aatatctgag ctttattaag    2040
tacttactac atgctaagag ctttttaagc acttatttaa tcctcattaa caaattcata    2100
aggtaggtgc tattgatagt ttagccataa ccagatatgg cttgttattt gtaagttatc    2160
atgaaaaggt ttatattcac tattctttat ttcagtgtag cacttttaga gccaaaaaaa    2220
ctcaggcaca aagaagttaa ataacttgcc gggtgcggtg gctcacccct gtaatcccag    2280
cactttggga ggccaaagca ggcggatcac ctgaggtcag gagtttgaga ccagccgggc    2340
caacatggtg caacctcgtc tttactaaaa atacaaaaac aaaaattagc cagggggtggt    2400 ggtatgcacc tgcagtccca gcaacatggg aggctgaaca ggagaatcgc ttgaacccgc    2460
gacagggagg ttgtgatgag ccaaggtcat gccactgcac tccagcctgg gagacagagc    2520
aagactccat ctcaaaaaca aaacaaaac aaaacaacaa caaaaaaga gttaaataa      2580 cttgtttaag atcacacagc tagtgcagtt acccccctctc agtaattatg tttggcaaat    2640
atgaaataca aggatctggc aaggttagga agaggttaag aatatcagtg acagtactct    2700
gaggcatctg ggcatgtcag atgaagattt attattcaga aaagtaagt cagctgttgc     2760 agggatcagt tgttttattc ctggaaaatg ttttttcattt tgctgcaaat ctatatctga   2820
cctgctgagg aaatcgtttg gtgaaatgaa tccagaaagc agagaaaatg cttcattact    2880
ttaaatagca gcattaagcc cattatagcc tctgaattgt cccttccttg agtttgctaa    2940
tgcttccaac ttagtcattt gaagcccaag agtctaattt tatatgccct gccaatgtcc    3000
tcatctattg cagaatgtat aattatctat ttgttttgga ctatatgtta caaaaattta    3060
aaacataaga tcctctctct atatttcatt attggtgaac ccacattgtg ctgtgttttg    3120
tgatatttta tcattttcta gattcttatg tggatctaat aacgaccact tgaacccagt    3180
ttcacagaat ccttattttt ctgttcaaat taggaattag ggacatggat gaaattggaa    3240
atcttcattc tcagtaaact atcgcaagga caaaaaacca acaccacat gttctcactc     3300 atagatagga attgaacaat gagaacacat ggagacagga aggggaacat cacactctag    3360
ggactgttgt ggggtgaggg g                                              3381
```

<210> SEQ ID NO 9
<211> LENGTH: 3301
<212> TYPE: DNA
<213> ORGANISM: Homo sapiens

<400> SEQUENCE: 9

```
aggcgccgcc gcagccggag cggctcccgg gccctgggcc gccgccggcc aggaagaaat     60
acttgtgttg gctgcatttc cagggatgct accagagctc aaggctgtca cctggtcttg   120
```

```
cccagaagag ccgttcttag aggcaggact tgatgaaggc tttcctgctg atggaatagg    180
tttgctagag ctggccttgg aattagaacc cttcatgtgg cctttataaa tatgcgtttg    240
agacagagtt atatgcagaa gttgaaaatg cctggaagat ttctggtttc tttcactact    300
tatcctgcct ttttgcatcg ctgccagatt tggatgatat gatattcaga ggggcacctt    360
aatcaaagcc attcttcaac aagacccacc tggcataaga ttgcacacat aattcaagat    420
ggccagtcaa cctcctgaag acactgcgga gtctcaggcc tctgatgagc tggagtgcaa    480
aatctgttac aatcgataca atctgaaaca gaggaaaccc aaagtgctgg agtgttgtca    540
tagggtttgt gccaaatgcc tctacaagat catagacttt ggggactccc cacaaggtgt    600
cattgtctgt cctttctgca ggtttgagac gtgcctgcca gatgatgaag ttagtagcct    660
gcccgatgac aacaacatcc ttgtaaactt gacttgtgga ggcaaaggga gaaagtgcct    720
gccagagaac cctactgagc tgctgctcac ccccaagagg ctggcctctc tggtcagtcc    780
ttctcacacg tcctccaact gcctggtcat aaccatcatg gaggtgcaga gagagagctc    840
cccgtccctg agctccactc ctgtggtaga attttatagg cctgcgagtt tcgactctgt    900
caccactgtg tcacacaact ggactgtgtg gaactgcacg tccctgctgt ttcagacatc    960
catccgggtg ttagtgtggt tgctaggttt gctctacttc agctccttac ccttaggaat   1020
ctacttactg gtgtctaaga aagtcaccct tggggtcgtc tttgtcagcc tggtcccttc   1080
gagcctcgtt attcttatgg tgtatggttt ttgccagtgt gtttgtcatg aatttctaga   1140
ctgtatggca cctccttctt aactgatatg caaaataaga aattggacac acattgccct   1200
gtttgagtgt gaagttagat aatttataat ttatttcctt ttatgttctt tatgattagt   1260
atccatgaca ttaacaaaac ccttggccac atgttgactt gattggtttt cctgtaggct   1320
ggaagtaaaa atgttcattt ctacttaggg gttagcaaaa ttgtataagc tcacacttca   1380
tggagcactg acagcagtga gtcttcccag agaaaggaca gggtttctct cagcactgcc   1440
agacagacgg caggggtgtg gtgtgttata ctatagggag agcatggatc cctcctttcg   1500
tattcatgga tgttctatga tggcagttgg acacaagagg aaagttgctc tgagacacaa   1560
agtgtgtact ccttttcccac cccatacccc tggtattgga acaccctaga attgtcttca   1620
ggtgttttct ctcttaagtc actctctgtg gtcggcgatc ccattgagat acttgtttcc   1680
tctgcccatt ctcccttgcc aagaggaaac tcggttccat tcccttgggt agtttcaact   1740
gaataccagt tttgccacat tactaaggag aatgaaaagc actgaggaat ttgcatcaca   1800
gtcagcttca tggcagaatg tggccatttg tccttgagac acactctttc ctccatgtct   1860
gttttcctct ctcctcagtc ttatctgaga agaatggagg agaaggaact tctcatacag   1920
cggttattat tgatgaaaac cttcatttga gtctttcctt ataacatctt agttttggtt   1980
tttttaaacc acattgccca atcagcctca cccttgtcc tgaaaaggtt ccatttaaat   2040
tagttgctat aaattcatca atactttttt tccctattat attttggtt ctattaggat   2100
ttacttaact gaatcttata acaattcgag gtgaactgtg gcaatgaaaa ccagaaacag   2160
ttaatgagat gcttcagctc acagtttgaa gtgctgagaa cctaagtatt tgctgtacg    2220
gtactgagct gtaccaaaat atgatggttt aggtttatgt gcaagacttt gtgttgtagt   2280
ctagacaaag gggtgggcaa gagacatgca aagctgaagc cctgcttgaa aagacccttc   2340
aaggaagtaa aatggcaggg gcagagtgca gcttaacatg ttgctatccc tgttgttttt   2400
gagttggttt tggaatggat tcaagttctt acacaattta ttttgaatac aagcataatc   2460
taggtgattt gagttaatga acttcttttc atgatgtagg gaaagttgaa tgtatatatt   2520
```

-continued

```
tctaagaaga atttgtttag cagattacaa gttggcaaaa tagactgttc acagaaacta    2580
ggcaaaaatt taaaaaaaca ttctagtctc taaaacccat tactaatgat taacattaaa    2640
atatttgtaa ctcttagaaa gggggcatta ctaagacgac tttaacttgt tatgaaatct    2700
ttgttgtgtg atgcaggtac agtgcgccca ttccaactgg aatagcagtt tgattttaat    2760
tgtaaaacta aacttcggga atatgtatgc ccaaagtaag taggatgaga atagtataca    2820
tgggatatgg tccaatgaat ttaagcccca agatacagct aaatacattt atgatttcat    2880
aaaatctagt ttagatagca ttgtgatgca atttccagaa atccattgt gtttagagta     2940 aataccatgt ttagaagatg ttttgtggtt tggatttata tatttgtaag gttttttta    3000 aaaaatgttc gttttgtttg aaatgtaaca ttgagtaaat tggtgagtta tataatgaga    3060
tttctagaaa gctctggaca tgggtacgat gtgttttgct tctctgtata atgtctacag    3120
tgataaactt gtgtctccgt gtattgtggc agtcttttt tctagttaat ttggctttag     3180
agagcaatct ttgtatgaca ccagaaaact cttcatgcta ttgaatgata aaagataat     3240 gctttaatat tttattcact gtgatactat tttgtttgtc tattaaattg ttattatttc    3300
c                                                                    3301
```

```
<210> SEQ ID NO 10
<211> LENGTH: 1129
<212> TYPE: DNA
<213> ORGANISM: Homo sapiens

<400> SEQUENCE: 10
```

```
gtcgctcccc tgctcggggt cagctagtgt ccgctctgct cggccgcggg ctcccggagg      60
actgcaggca ggatgacgca aaacacggtg attgtgaatg gagttgctat ggcctctagg    120
ccatcccagc ccacccacgt caacgtccac atccaccagg agtcagcttt gacacaactg    180
ctgaaagctg gaggttctct gaagaagttt ctttttcacc ctggggacac tgtgccttcc    240
acagccagga ttggttatga gcagctggct ctaggggtga ctcagatatt gctgggggtt    300
gtgagttgtg ttcttggagt gtgtctcagc ttggggccct ggactgtgct gagtgcctca    360
ggctgtgcct tctgggcggg gtctgtggtg atcgcagcag gagctgggc cattgtccat     420 gagaagcacc cgggcaaact tgctggctat atatccagcc tgctcaccct ggcaggcttt    480
gctacagcta tggctgctgt tgtcctctgc gtgaatagct tcatctggca aactgaaccc    540
tttttataca tcgacactgt gtgtgatcgc tcagaccctg tcttccctac cactgggtac    600
agatggatgc ggcgaagtca agagaaccaa tggcagaagg aggagtgtag agcttacatg    660
cagatgctga ggaagttgtt cacagcaatc cgtgccctgt tcctggctgt ctgtgtcttg    720
aaggtcattg tgtccttggt ttccttggga gtaggtcttc gaaacttgtg tggccagagc    780
tcccagcccc tgaatgagga aggatcagag aagaggctac tggggagaa ttcagtgccc     840 ccttcgccct ctagggagca gacctccact gccattgtcc tgtgagctgc caaagacccc    900
acggggtgcc cgcatgtccc tgtctagggc agcccagggc ccccactcct ggctcctcac    960
acttgcctcc cctatggccg ctctccagac cctcctcctt tcttctcccc acatccgcac   1020
ctgctgttcc cactctgggg ttctcaagtc catgaacaga tattgttgca ttttccacaa   1080
tgctgattaa acataataaa caatccagaa aagcagtttt gcccagaaa              1129
```

```
<210> SEQ ID NO 11
<211> LENGTH: 1206
<212> TYPE: DNA
```

<213> ORGANISM: Homo sapiens

<400> SEQUENCE: 11

| | | | | | |
|---|---|---|---|---|---|
| cccacctcag | cctcccaaag | cactgggatt | acaggcgtga | gctattgtgc | ccagctggga | 60 |
| tcttgacaaa | gacactattt | ctctcctttc | acctgtgctg | tgtatttttc | cctcgcctag | 120 |
| ttcccagacc | tcactgctat | atgtcttctc | cctggcaggc | aggatgacgc | aaaacacggt | 180 |
| gattgtgaat | ggagttgcta | tggcctctag | gccatcccag | cccacccacg | tcaacgtcca | 240 |
| catccaccag | gagtcagctt | tgacacaact | gctgaaagct | ggaggttctc | tgaagaagtt | 300 |
| tcttttttcac | cctggggaca | ctgtgccttc | cacagccagg | attggttatg | agcagctggc | 360 |
| tctaggggtg | actcagatat | tgctgggggt | tgtgagttgt | gttcttggag | tgtgtctcag | 420 |
| cttggggccc | tggactgtgc | tgagtgcctc | aggctgtgcc | ttctgggcgg | ggtctgtggt | 480 |
| gatcgcagca | ggagctgggg | ccattgtcca | tgagaagcac | ccgggcaaac | ttgctggcta | 540 |
| tatatccagc | ctgctcaccc | tggcaggctt | tgctacagct | atggctgctg | ttgtcctctg | 600 |
| cgtgaatagc | ttcatctggc | aaactgaacc | cttttatac | atcgacactg | tgtgtgatcg | 660 |
| ctcagaccct | gtcttcccta | ccactgggta | cagatggatg | cggcgaagtc | aagagaacca | 720 |
| atggcagaag | gaggagtgta | gagcttacat | gcagatgctg | aggaagttgt | tcacagcaat | 780 |
| ccgtgccctg | ttcctggctg | tctgtgtctt | gaaggtcatt | gtgtccttgg | tttccttggg | 840 |
| agtaggtctt | cgaaacttgt | gtggccagag | ctcccagccc | ctgaatgagg | aaggatcaga | 900 |
| gaagaggcta | ctgggggaga | attcagtgcc | cccttcgccc | tctagggagc | agacctccac | 960 |
| tgccattgtc | ctgtgagctg | ccaaagaccc | acggggtgc | ccgcatgtcc | ctgtctaggg | 1020 |
| cagcccaggg | cccccactcc | tggctcctca | cacttgcctc | ccctatggcc | gctctccaga | 1080 |
| ccctcctcct | ttcttctccc | cacatccgca | cctgctgttc | ccactctggg | gttctcaagt | 1140 |
| ccatgaacag | atattgttgc | attttccaca | atgctgatta | aacataataa | acaatccaga | 1200 |
| aaagca | | | | | | 1206 |

<210> SEQ ID NO 12
<211> LENGTH: 1303
<212> TYPE: DNA
<213> ORGANISM: Homo sapiens

<400> SEQUENCE: 12

| | | | | | |
|---|---|---|---|---|---|
| cgagtgggag | cgcagggggc | gcgcgggggc | tcggtcttct | cccgcccggt | ccgctcctcc | 60 |
| gggcggaacc | ccctttgccg | ggcccccggg | ccgcagctgg | tttcgggaaa | ccgcgcagcc | 120 |
| tgggcgggc | cgcagccccc | accgtgcat | ctgccgtctc | cgccctcccg | tcgctcccct | 180 |
| gctcggggtc | agctagtgtc | cgctctgctc | ggccgcgggc | tcccgaggga | ctgcaggtga | 240 |
| ggccaggcag | gatgacgcaa | aacacggtga | ttgtgaatgg | agttgctatg | gcctctaggc | 300 |
| catcccagcc | cacccacgtc | aacgtccaca | tccaccagga | gtcagcttttg | acacaactgc | 360 |
| tgaaagctgg | aggttctctg | aagaagtttc | ttttttcaccc | tggggacact | gtgccttcca | 420 |
| cagccaggat | tggttatgag | cagctggctc | taggggtgac | tcagatattg | ctgggggttg | 480 |
| tgagttgtgt | tcttggagtg | tgtctcagct | tggggccctg | gactgtgctg | agtgcctcag | 540 |
| gctgtgcctt | ctgggcgggg | tctgtggtga | tcgcagcagg | agctggggcc | attgtccatg | 600 |
| agaagcaccc | gggcaaactt | gctggctata | tatccagcct | gctcaccctg | gcaggctttg | 660 |
| ctacagctat | ggctgctgtt | gtcctctgcg | tgaatagctt | catctggcaa | actgaaccct | 720 |
| ttttatacat | cgacactgtg | tgtgatcgct | cagaccctgt | cttccctacc | actgggtaca | 780 |

```
gatggatgcg gcgaagtcaa gagaaccaat ggcagaagga ggagtgtaga gcttacatgc    840
agatgctgag gaagttgttc acagcaatcc gtgccctgtt cctggctgtc tgtgtcttga    900
aggtcattgt gtccttggtt tccttgggag taggtcttcg aaacttgtgt ggccagagct    960
cccagcccct gaatgaggaa ggatcagaga agaggctact gggggagaat tcagtgcccc   1020
cttcgccctc tagggagcag acctccactg ccattgtcct gtgagctgcc aaagacccca   1080
cggggtgccc gcatgtccct gtctagggca gcccagggcc cccactcctg ctcctcaca    1140 cttgcctccc ctatggccgc tctccagacc ctcctccttt cttctcccca catccgcacc   1200
tgctgttccc actctggggt tctcaagtcc atgaacagat attgttgcat tttccacaat   1260
gctgattaaa cataataaac aatccagaaa agcagttttg ccc                     1303
```

<210> SEQ ID NO 13
<211> LENGTH: 1430
<212> TYPE: DNA
<213> ORGANISM: Homo sapiens

<400> SEQUENCE: 13

```
gctgaccatg ctggaactgc ggcgactaca gagcctgcgg gaacctcccc tttcgcccaa     60
gatctgctct gtccccctca tcctcctccc agggccctgg cgtctgggtc aagcagcgcc    120
ccacacctcg acccctcacc ccctcctccc gggctcttcc tgcggcctcc cctccacagt    180
ccgcaggctc tgggacagga ccgagtcctt ggctgcctgt ggagctcctg tgccagcagc    240
tgcgccccgg ctgcgctccg gatacccca tccccgccac cgccgacctc ccgctccacc     300
gactgctgct cacgcccgac gggttcacgc cgccctgcc ccgtgaagga ccgcgctgcg     360
gtgcggaggc aggatgacgc aaaacacggt gattgtgaat ggagttgcta tggcctctag    420
gccatcccag cccacccacg tcaacgtcca catccaccag gagtcagctt tgacacaact    480
gctgaaagct ggaggttctc tgaagaagtt tcttttttcac cctggggaca ctgtgccttc    540
cacagccagg attggttatg agcagctggc tctaggggtg actcagatat tgctgggggt    600
tgtgagttgt gttcttggag tgtgtctcag cttgggggcc tggactgtgc tgagtgcctc    660
aggctgtgcc ttctgggcgg ggtctgtggt gatcgcagca ggagctgggg ccattgtcca    720
tgagaagcac ccgggcaaac ttgctggcta tatatccagc ctgctcaccc tggcaggctt    780
tgctacagct atggctgctg ttgtcctctg cgtgaatagc ttcatctggc aaactgaacc    840 cttttttatac atcgacactg tgtgtgatcg ctcagaccct gtcttcccta ccactgggta   900
cagatggatg cggcgaagtc aagagaacca atggcagaag gaggagtgta gagcttacat    960
gcagatgctg aggaagttgt tcacagcaat ccgtgccctg ttcctggctg tctgtgtctt   1020
gaaggtcatt gtgtccttgg tttccttggg agtaggtctt cgaaacttgt gtggccagag   1080
ctcccagccc ctgaatgagg aaggatcaga gaagaggcta ctgggggaga attcagtgcc   1140
cccttcgccc tctagggagc agacctccac tgccattgtc ctgtgagctg ccaaagaccc   1200
cacggggtgc ccgcatgtcc ctgtctaggg cagcccaggg ccccactcc tggctcctca    1260 cacttgcctc cctatggcc gctctccaga ccctcctcct tcttctccc cacatccgca    1320 cctgctgttc ccactctggg gttctcaagt ccatgaacag atattgttgc attttccaca   1380
atgctgatta aacataataa acaatccaga aaagcagttt tgcccagaaa               1430
```

<210> SEQ ID NO 14
<211> LENGTH: 3458
<212> TYPE: DNA

<213> ORGANISM: Homo sapiens

<400> SEQUENCE: 14

| | | | | | |
|---|---|---|---|---|---|
| aaaagacttc | agtggcagac | aaaggaggag | taataagatc | gctaggggc | ccgtgcccag | 60 |
| cccacccacg | cacaatctca | gtcctcgcaa | tacccacaag | gtaggtgcta | ggatcacacc | 120 |
| ctttacggac | gcggcacctg | cgacagggat | gcgcgaggag | tcaggggcc | tcgccggatc | 180 |
| gaacctaagc | tggggaagag | tatttcttgt | atttttagga | gaaattctca | gcctcgggga | 240 |
| agagtatttc | ttgatgaggg | aagagcgcgg | ggaagacact | cacgcacgca | caaacatgtg | 300 |
| ggcggccatg | gtgtgcccag | cgccgtgctg | gcttctggga | accccagtg | acaagacgg | 360 |
| acaaggtacc | ggctctcagg | ggaagtggga | gccagtcaca | agcgtaccta | atttcggaga | 420 |
| gtgacaagta | ctctgaaaaa | gaagaaggt | agggctggtg | actggccaat | ttaagcgggc | 480 |
| aggagtctgc | tggggacgg | agaccagcct | caggtctggg | ttggggacag | aagctgtgcc | 540 |
| taagtgtggt | gcaggatgca | gttgcaaagg | agcgcttccg | atcgcacttg | atgctcgcca | 600 |
| cgtccctgca | aagtgctccc | gccccctttc | tgcaaatgag | gaaacgggac | gcgcggctcg | 660 |
| ccgggccagc | ccgcgtgcct | gcgcagtccc | ctccccgaga | accatcccct | tgccccgccc | 720 |
| agcgtcaggg | gtgcgcggcc | gccgagagac | cccggaggcg | tagccggctg | cggaggcgaa | 780 |
| gaggtggcag | cgcgagctgg | gaccagcgtc | tcggaggcgc | cgcagaattc | acagatggat | 840 |
| tcagtggaaa | agacaacaaa | tagaagtgaa | caaaaatcca | gaaagttttt | aaaaagcctc | 900 |
| atccggaaac | agccccagga | actgctcctg | gttatcggga | ctggcgtcag | cgcagcagtg | 960 |
| gcccccggaa | tccctgccct | tgctcgtgg | agaagccgca | tcgaggccgt | catcgaggct | 1020 |
| gcagagcagc | tggaggtgct | gcaccccgga | gacgtcgccg | agttccggag | gaaagtgaca | 1080 |
| aaggaccggg | acctgttggt | tgtcgcccat | gatctgatcc | ggaagatgtc | acctcgcaca | 1140 |
| ggcgatgcca | agcccagctt | cttccaggac | tgcctgatgg | aggtgtttga | cgacctggag | 1200 |
| cagcacatcc | ggagtcctgt | ggtgctgcag | tcgatcctca | gcctgatgga | caggggcgcc | 1260 |
| atggtcctga | ccaccaacta | tgacaacctg | ctggaggcct | ttggccggcg | gcagaacaag | 1320 |
| cccatggagt | ccctggactt | gaaggacaag | accaaggtcc | ttgaatgggc | aagagggcac | 1380 |
| atgaagtacg | gcgtcctcca | cattcacggc | ctctacacgg | accccctgcgg | ggtggtgctg | 1440 |
| gacccatcgg | ggtataaaga | cgtcactcaa | gacgcagaag | tcatggaagt | cctccagaac | 1500 |
| ttataccgca | ccaagtcctt | tctgtttgtg | ggctgtgggg | agacccttcg | tgatcagata | 1560 |
| ttccaggccc | tctttcttta | ctccgtgccg | aataaggtgg | atttggagca | ctacatgctt | 1620 |
| gtgctgaagg | agaatgaaga | ccatttcttt | aagcatcagg | cagatatgct | tctgcacgga | 1680 |
| atcaaagttg | tatcctacgg | ggactgtttt | gaccactttc | aggatatgt | gcaagacctt | 1740 |
| gccactcaga | tctgcaaaca | gcaaagccca | gatgctgatc | gcgtggacag | caccacatta | 1800 |
| ttgggtaatg | catgccagga | ctgtgcaaag | aggaagttag | aagagaatgg | aattgaagtt | 1860 |
| tcaaaaaaac | gcacacaatc | agatactgat | gatgctggag | ggtcttgaaa | tctttacagt | 1920 |
| aaaacctgca | acttgaaaac | tagccttctg | taaccacagt | gcccaaacga | agaggaatgt | 1980 |
| atggagaact | ccacgtggat | ctctgattgc | gaaaccgtca | catacaccaa | gagagccaca | 2040 |
| tgggcatgtg | gccctcaagg | ctgggtgaga | gggctcccct | gtgtgttgaa | ctatgcagga | 2100 |
| gggtgacgcg | gacacatttc | aggtggactt | tgcaaggact | gatggatagc | tacctcaggg | 2160 |
| accagaatcc | gtgggaaggg | atggacctgg | tgttcccgtt | cccatctgac | aggctctctt | 2220 |
| ttgtcaaggt | ggtattttc | gtaataaaag | gggaagagta | aagactgtcc | aagcaacagt | 2280 |

```
agctgccaaa gagaaaatac gaaatagaca cttttttttt ttgagtcaga gtctcactct    2340
gtcacccagg acagagtgca gtggtacgat ctcaagctca ctgcagccac caccgcctgg    2400
gctcaagtga ttctcctgcc tcagcctccc gagtagctgg gattacaggc gtccaccacc    2460
atgcccagct aattttttta ttttagtag agttggagtt tcaccatgtt ggccaggatg     2520
gtctcgaact cttgacctca ggtgatccac ccgccttggc ctcccaaagt gctaggatta    2580
caggcatgag ccactgcgcc agcaaaata aacacatttt ataatttgta tgtggaaaca     2640
tgttactata gaaagcattt taaaggtacg ttttaaaggt ccactgttaa atagtaaaga    2700
atgaatccgc tagcgaaaat gttttaggg agaacagctg atcaaaagg gcttctttgg      2760
aattaggttg ttttagtaac ttctgttcca agaaacaca ggtctgatat tgctaagaac     2820
tgaaatcgga ggagccagag gccctttca gtccaggcca acattgtgca cggccactgt    2880
gggactgaca accgggatag ctcaagttcg agagaccagg tttcaaacat tataagttcc    2940
aggctttgca agtctttatt ctctgggta atatccagtc tttctgttat tgtctcttaa     3000
aattctcttc catggcccac attaagggag tttgcagaga gtgagggagg caaaacttga    3060
aaagggcctg caacactttta aaccttctca ggttcaccca catgaaacgg ctgtgctgag   3120
tgtgctgccg gtgcccgggg agcttctctg actgtgaccc ggcagaggct tctgtggcgg    3180
tgcatgagcg gccctacagt ggagggttct ctttggaaac aaacagccct gcttggtttc    3240
agtttgaggc cacttatctt caatgtgaca tttcttgcca agccctgtga cactccccat    3300
tgatgactcc cataggtaca gataaagtta agaacaggaa acagaagggt aggatgcata    3360
gggagggaga gaagccctga aaacttttttt tttcttttg aagcatggaa aacaaatctt    3420
ttatgccact ccagccataa ataaaatttt aacttcaa                            3458

<210> SEQ ID NO 15
<211> LENGTH: 1776
<212> TYPE: DNA
<213> ORGANISM: Homo sapiens

<400> SEQUENCE: 15
cggggcgggg cctccgggga ccgcggggcc gttggtttcg ggacggaacg ttcacgcggc      60
tggggcgggc gcgcggggga agggtttgcg gcggcgccgc tgccggctaa cgcggagggg    120
cgcctggagg cggcgtggcg tccgctctgg ctccgactcc ggctctcgct ctcgcttcta    180
gcccgcgtgc ctgcgcagtc ccctccccga gaaccatccc cttgccccgc ccagcgtcag    240
gggtgcgcgg ccgccgagag accccggagg cgtagccggc tgcggaggcg aagaggtggc    300
agcgcgagct gggaccagcg tctcggaggc gccgcagaat tcacagatgg attcagtgga    360
aaagacaaca aatagaagtg aacaaaaatc cagaaagttt taaaaagcc tcatccggaa     420
acagccccag gaactgctcc tggttatcgg gactggcgtc agcgcagcag tggcccccgg    480
aatccctgcc ctttgctcgt ggagaagctg catcgaggcc gtcatcgagg ctgcagagca    540
gctggaggtg ctgcaccccg agacgtcgc cgagttccgg aggaaagtga caaaggaccg    600
ggacctgttg gttgtcgccc atgatctgat ccggaagatg tcacctcgca caggcgatgc   660
caagcccagc ttcttccagg actgcctgat ggaggtgttt gacgacctgg agcagcacat   720
ccggagtcct gtggtgctgc agtcgatcct cagcctgatg gacaggggcg ccatggtcct   780
gaccaccaac tatgacaacc tgctggaggc ctttggccgg cggcagaaca gcccatggaa    840
gtccctggac ttgaaggaca agaccaaggt ccttgaatgg gcaagagggc acatgaagta   900
```

```
cggcgtcctc cacattcacg gcctctacac ggacccctgc ggggtggtgc tggacccatc      960
ggggtataaa gacgtcactc aagacgcaga agtcatggaa gtcctccaga acttataccg     1020
caccaagtcc tttctgtttg tgggctgtgg ggagacccct cgtgatcaga tattccaggc     1080
cctctttctt tactccgtgc cgaataaggt ggatttggag cactacatgc ttgtgctgaa     1140
ggagaatgaa gaccatttct ttaagcatca ggcagatatg cttctgcacg gaatcaaagt     1200
tgtatcctac ggggactgtt ttgaccactt tccaggatat gtgcaagacc ttgccactca     1260
gatctgcaaa cagcaaagcc cagatgctga tcgcgtggac agcaccacat tattgggtaa     1320
tgcatgccag gactgtgcaa agaggaagtt agaagagaat ggaattgaag tttcaaaaaa     1380
acgcacacaa tcagatactg atgatgctgg agggtcttga aatctttaca gtaaaacctg     1440
caacttgaaa actagccttc tgtaaccaca gtgcccaaac gaagaggaat gtatggagaa     1500
ctccacgtgg atctctgatt gcgaaaccgt cacatacacc aagagagcca catgggcatg     1560
tggccctcaa ggctgggtga gagggctccc ctgtgtgttg aactatgcag gagggtgacg     1620
cggacacatt tcaggtggac tttgcaagga ctgatggata gctacctcag ggaccagaat     1680
ccgtgggaag ggatggacct ggtgttcccg ttcccatctg acaggctctc ttttgtcaag     1740
gtggtatttt tcgtaataaa aggggaagag taaaga                              1776

<210> SEQ ID NO 16
<211> LENGTH: 3511
<212> TYPE: DNA
<213> ORGANISM: Homo sapiens

<400> SEQUENCE: 16 gggggatttgg ggctgggtcg gccggggtcg gggaggggggg tggtgaaaag gtgacaggga      60
gctgcccccg ctcaagagcc ggtggttggg ggtctgagaa gaagtcacca atatgaagtt     120
attcggcttc gggagccgca ggggccagac ggcccagggc tccatagacc acgtctacac     180
gggttccgga taccgaatcc gggactccga actgcagaag atccacaggg cagctgtcaa     240
aggcgacgcc gcggaggtgg agcgctgcct ggcgcgcagg agcggagacc tggacgccct     300
ggacaagcag cacagaactg ctctacactt ggcctgtacc agtggccatg tgcaagtggt     360
cactctcctg gttaacagaa aatgccagat tgatgtctgt gacaaagaaa acagaacgcc     420
tttgatacag gctgtccatt gccaggaaga ggcttgtgcc gttattctgc tggaacatgg     480
cgccaatcca aaccttaagg atatctacgg caacactgct ctccattatg ccgtgtatag     540
tgagagcacc tcactggcag aaaaactgct ttcccatggt gcacatattg aagcactgga     600
caaggacaat aatacccccac ttttatttgc tataaatttgc aagaaagaga aatggtgga     660
attttttattg aaaaagaaag caagttcaca tgccgttgat aggctgagac ggtcagctct     720
catgcttgct gtatactatg actcaccagg tattgtcaat atccttctta agcaaaatat     780
tgatgtcttc gctcaagaca tgtgtggacg agatgcagaa gattatgcta tttctcatca     840
tttgacaaaa attcaacaac aaattttgga acataaaaag aagatactta aaaaggagaa     900
atcagatgtt ggaagttctg atgaatctgc agtcagcatt tccatgaac tgcgtgtgga     960
ttcattgcct gcatcggatg acaaagactt gaatgttgct actaagcagt gtgtccccga    1020
gaaagtgtca gagcctttac ctggatcttc gcatgaaaaa ggaaacagaa tagtcaatgg    1080
acaaggagaa gggcctcctg caaaaacatcc ttccttgaag cctagcactg aagtggaaga    1140
tcctgctgtg aaaggagcag tacaaagaaa gaatgtacag acattgagag cagaacaagc    1200
cttaccagtg gcttcagagg aagagcaaga aaggcatgaa agaagtgaaa agaagcaacc    1260
```

```
acaggtcaaa gaaggaaata atacaaacaa aagtgaaaaa atacaacttt cagaaaatat    1320
atgtgatagt acatcttctg ctgctgctgg cagattaacc caacaaagaa agattgggaa    1380
aacgtatcct cagcaatttc ccaagaagct gaaggaagag catgatagat gcaccttaaa    1440
acaagaaaat gaagaaaaaa caaatgttaa tatgctgtac aaaaaaaata gagaagaatt    1500
agaaaggaaa gagaaacaat ataagaaaga agttgaagca aaacaacttg aaccaactgt    1560
tcagtcacta gagatgaaat caaagactgc aagaaatact ccaaattggg attttcataa    1620
tcatgaagaa atgaaaggtc tgatggatga aaattgcatt ttgaaggcag atattgctat    1680
actcagacag gaaatatgta caatgaaaaa tgacaacttg gaaaaagaaa ataaatatct    1740
taaggacatt aaaattgtta agaaacaaa tgctgcccctt gaaaagtata taaaactcaa     1800
tgaggaaatg ataacagaaa cagcattccg gtatcaacaa gagcttaatg atctcaaggc    1860
tgagaataca aggctcaatg ccgaactgtt gaaggaaaaa gaaagcaaga aaagactgga    1920
agctgacatt gaatcttatc agtctagact ggctgctgct ataagcaaac acagtgaaag    1980
tgtgaaaaca gaaagaaacc taaaacttgc tttagagaga cacgagatg tttctgtaca     2040 agtagaaatg agttctgcta tttccaaagt aaaagctgag aatgagtttc ttactgaaca    2100
actttctgaa acacaaatta aattcaatgc cttaaaagat aagttccgta agacaagaga    2160
tagtctcaga aaaagtcat tggctttaga aactgtacaa aacgacctaa gccaaacaca      2220
gcagcaaaca caggaaatga agagatgta tcaaaatgca gaagctaaag tgaataattc     2280
cactggaaag tggaactgtg tagaagagag gatatgtcac ctccaacgtg aaaatgcgtg    2340
gcttgtacag caactagatg acgttcatca gaaagaggat cataaagaga tagtaactaa    2400
tatccaaaga ggctttattg agagtggaaa gaaagacctc gtgctagaag agaaaagtaa    2460
gaagctaatg aatgaatgtg atcatttaaa agaaagtctc tttcagtatg agagagagaa    2520
aacagaagga gtagtaagta tcaaggaaga taaatatttt caaacttcta gaaagacaat    2580
ttaaacattt ggttctggat acatgttgaa cttagttgaa tataaaaatc tagattaaaa    2640
gtgtgtttac catactgtat aattccattt acatgaagca tccagaaaag ataaatgtat    2700
agggacaaaa agtagattca tgtttgcaag gggctggggc tggaagctgg tagtgactgc    2760
taatgggcat gaggaatctt acagtgatgg aaatgctcta aagttggatt gtagagatgg    2820
ctgcacaact cagtaaatgt actaaaaatc ttttaactta aaacagatac attctatagt    2880
atgtaaatta tatttcaaca aagctgtttt aataaaaaaa ggaaaaatgt gtttactata    2940
tcggcttaga aacatgcctc atttctagga aataaaagat agaggtgaga gatgatttac    3000
tttgagaaaa gacattgtgt cacctatgaa atttttattag gcacagagtc atattttaag    3060
gtagatagtt ctgtattgct gaaatagtaa ttttaatgtc tttatgttgc cacatgttaa    3120
gaccataatg tagttataaa tggaaatgtt tacacctgaa gtgagtattt tcaaattaaa    3180
atttaattaa gtgattttct tcgacactta attctagatt ccccagatga attgaagtgt    3240
attgctgtgt cttgtaatac cttgctttaa ctagcttttt atgtatttta gttggtatag    3300
ctttgttatt attcatatta acaaatctga aaatatgtca aattacgtgt ttttatgacc    3360
atgtaatgtt ttaaaggcac ctacttgtta taaaatcata atttaggata aatgtggtaa    3420
aacttagcaa aactatattt ggtttagttt tcccactggt atttatagtt tactttgaat    3480
atttatatta ataattagct cataatttt a                                     3511
```

<210> SEQ ID NO 17

<211> LENGTH: 1338
<212> TYPE: DNA
<213> ORGANISM: Homo sapiens

<400> SEQUENCE: 17

```
gggcagtctg cgaagattgc aggcattgtt tgttcttgtc ttggatttat gcctttaaat      60
ttcacctttt attacacagc tatagcaggc ctttttatga gactaacctg gcctctccac     120
taaaggatgt gtgactttct ggggacagaa gagtacagtc cctgacatca cacactgcag     180
agatggataa ccaaggagta atctactcag acctgaatct gcccccaaac ccaaagaggc     240
agcaacgaaa acctaaaggc aataaaaact ccattttagc aactgaacag gaaataacct     300
atgcggaatt aaaccttcaa aaagcttctc aggattttca agggaatgac aaaacctatc     360
actgcaaaga tttaccatca gctccagaga agctcattgt tgggatcctg ggaattatct     420
gtcttatctt aatggcctct gtggtaacga tagttgttat tccctcacgt cattgtggcc     480
attgtcctga ggagtggatt acatattcca acagttgtta ctacattggt aaggaaagaa     540
gaacttggga agagagtttg ctggcctgta cttcgaagaa ctccagtctg ctttctatag     600
ataatgaaga agaaatgaaa tttctgtcca tcatttcacc atcctcatgg attggtgtgt     660
ttcgtaacag cagtcatcat ccatgggtga caatgaatgg tttggctttc aaacatgaga     720
taaaagactc agataatgct gaacttaact gtgcagtgct acaagtaaat cgacttaaat     780
cagcccagtg tggatcttca ataatatatc attgtaagca taagctttag aggtaaagcg     840
tttgcatttg cagtgcatca gataaattgt atatttctta aaatagaaat atattatgat     900
tgcataaaatc ttaaaatgaa ttatgttatt tgctctaata agaaaattct aaatcaatta     960
ttgaaacagg atacacacaa ttactaaagt acagacatcc tagcatttgt gtcgggctca    1020
ttttgctcaa catggtattt gtggttttca gccttctaa aagttgcatg ttatgtgagt    1080
cagcttatag gaagtaccaa gaacagtcaa acccatggag acagaaagta gaatagtggt    1140
tgccaatgtc tgagggaggt tgaaatagga gatgacctct aactgataga acgttactt    1200
gtgtcgtgat gaaaactttc taaatttcag tagtggtgat ggttgtaact ctgcgaatat    1260
actaaacatc attgatttt aatcatttta agtgcatgaa atgtatgctt tgtacacgac    1320
acttcaataa agctatcc                                                  1338
```

<210> SEQ ID NO 18
<211> LENGTH: 1392
<212> TYPE: DNA
<213> ORGANISM: Homo sapiens

<400> SEQUENCE: 18

```
gggcagtctg cgaagattgc aggcattgtt tgttcttgtc ttggatttat gcctttaaat      60
ttcacctttt attacacagc tatagcaggc ctttttatga gactaacctg gcctctccac     120
taaaggatgt gtgactttct ggggacagaa gagtacagtc cctgacatca cacactgcag     180
agatggataa ccaaggagta atctactcag acctgaatct gcccccaaac ccaaagaggc     240
agcaacgaaa acctaaaggc aataaaaact ccattttagc aactgaacag gaaataacct     300
atgcggaatt aaaccttcaa aaagcttctc aggattttca agggaatgac aaaacctatc     360
actgcaaaga tttaccatca gctccagaga agctcattgt tgggatcctg ggaattatct     420
gtcttatctt aatggcctct gtggtaacga tagttgttat tccctctaca ttaatacaga     480
ggcacaacaa ttcttccctg aatacaagaa ctcagaaagc acgtcattgt ggccattgtc     540
ctgaggagtg gattacatat tccaacagtt gttactacat tggtaaggaa agaagaactt     600
```

```
gggaagagag tttgctggcc tgtacttcga agaactccag tctgctttct atagataatg      660
aagaagaaat gaaatttctg tccatcattt caccatcctc atggattggt gtgtttcgta      720
acagcagtca tcatccatgg gtgacaatga atggtttggc tttcaaacat gagataaaag      780
actcagataa tgctgaactt aactgtgcag tgctacaagt aaatcgactt aaatcagccc      840
agtgtggatc ttcaataata tatcattgta agcataagct ttagaggtaa agcgtttgca      900
tttgcagtgc atcagataaa ttgtatattt cttaaaatag aaatatatta tgattgcata      960
aatcttaaaa tgaattatgt tatttgctct aataagaaaa ttctaaatca attattgaaa     1020
caggatacac acaattacta aagtacagac atcctagcat ttgtgtcggg ctcatttttgc    1080 tcaacatggt atttgtggtt ttcagccttt ctaaaagttg catgttatgt gagtcagctt     1140
ataggaagta ccaagaacag tcaaacccat ggagacagaa agtagaatag tggttgccaa     1200
tgtctgaggg aggttgaaat aggagatgac ctctaactga tagaacgtta ctttgtgtcg     1260
tgatgaaaac tttctaaatt tcagtagtgg tgatggttgt aactctgcga atatactaaa     1320
catcattgat ttttaatcat tttaagtgca tgaaatgtat gctttgtaca cgacacttca     1380
ataaagctat cc                                                          1392
```

<210> SEQ ID NO 19
<211> LENGTH: 1209
<212> TYPE: DNA
<213> ORGANISM: Homo sapiens

<400> SEQUENCE: 19

```
tgcagagatg aataaacaaa gaggaacctt ctcagaagtg agtctggccc aggacccaaa       60
gcggcagcaa aggaaaccta aaggcaataa aagctccatt tcaggaaccg aacaggaaat      120
attccaagta gaattaaatc ttcaaaatcc ttccctgaat catcaaggga ttgataaaat      180
atatgactgc caaggtttac tgccacctcc agagaagctc actgccgagg tcctaggaat      240
catttgcatt gtcctgatgg ccactgtgtt aaaaacaata gttcttattc ctttcctgga      300
gcagaacaat ttttcccccga atacaagaac gcagaaagca cgtcattgtg gccattgtcc      360
tgaggagtgg attacatatt ccaacagttg ttattacatt ggtaaggaaa gaagaacttg      420
ggaagagagt ttgctggcct gtacttcgaa gaactccagt ctgctttcta tagataatga      480
agaagaaatg aaatttctgg ccagcatttt accttcctca tggattggtg tgtttcgtaa      540
cagcagtcat catccatggg tgacaataaa tggtttggct ttcaaacata agataaaaga      600
ctcagataat gctgaactta actgtgcagt gctacaagta aatcgactta aatcagccca      660
gtgtggatct tcaatgatat atcattgtaa gcataagctt tagaagtaaa gcatttgcgt      720
ttgcagtgca tcagatacat tttatatttc ttaaaataga aatattatga ttgcataaat      780
ctgaaaatga attatgttat ttgctctgat acaaaaattc taaatcaatt attgaaatag      840
gatgcacaca attactaaag tacagacatc ctagcatttg tgtcgggctc attttgctca     900
acatggtatt tgtggttttc agcctttcta aaagttgcat gttatgtgag tcagcttata     960
ggaagtacca agaacagtca aacccatgga gacagaaagt agaatagtgg ttgccaatgt    1020
ctcagggagg ttgaaatagg agatgaccac taattgatag aacgtttctt tgtgtcgtga    1080
tgaaaacttt ctaaatttca gtagtggtga tggttgtaac tctgcgaata tactaaacat    1140
cattgatttt taatcatttt aagtgcatga aatgtatgct ttgtacatga cacttcaata    1200
aagctatcc                                                            1209
```

<210> SEQ ID NO 20
<211> LENGTH: 10490
<212> TYPE: DNA
<213> ORGANISM: Homo sapiens

<400> SEQUENCE: 20

| | | | | | |
|---|---|---|---|---|---|
| accccccatga | atccacaacc | ataaccatgg | ccacgcgggt | cgaggtgggc | tccataacgc | 60 |
| ccttgacggc | cgtgccaggc | ctgggtgaga | tgggcaagga | ggagaccctg | acgaggacct | 120 |
| acttcctcca | ggccggcgaa | gcctctgggg | ctcccccagc | ccggatcttg | gaagcgaaga | 180 |
| gcccctgcg | gagcccggcc | cggttactcc | ctctgccaag | gctcgccccc | aaacccttct | 240 |
| cgaaggagca | ggacgtgaaa | tctcctgtcc | cgtctctgcg | gcccagttcg | actggacctt | 300 |
| cccccctctgg | ggggctctct | gaggagccag | cagcaaagga | tctggacaac | aggatgcccg | 360 |
| gcttggtggg | gcaggaggtg | ggcagtgggg | agggcccgag | gacgagctcg | ccctcttca | 420 |
| acaaggctgt | gttcctgcgg | cccagctcca | gcaccatgat | tctcttcgaa | accaccaaaa | 480 |
| gcggccccgc | tctggggaag | gcggttagtg | aggggcgg | ggaggccaag | ctaggtgtgt | 540 |
| ccggctcccg | gcctgaggtg | gctgccaagc | ccgccctgcc | cacccagaag | cctgcgggga | 600 |
| cccttccccg | gtcagctccc | ctgtctcagg | acacaaaacc | acctgtaccc | caagaggagg | 660 |
| caggccaaga | ccatcctccc | tcaaaggcca | gcagtgtgga | ggacacggca | cgccccccttg | 720 |
| tggagcccag | gcctcgcctg | aagagaaggc | ccgtgtctgc | catttcacg | gagtccattc | 780 |
| agcctcagaa | gccaggcccc | ggcgcagcgg | ccacagtggg | caaagtgcca | cccaccccctc | 840 |
| ccgagaagac | gtgggtgagg | aagcccaggc | ccttgtccat | ggacctcacg | gcccggtttg | 900 |
| agaacaaaga | ggccttgctg | aggaaggtgg | ccgatgaagg | aagtggaccc | acagcagggg | 960 |
| atatggctgg | gctagagagg | cccagagcag | cgtccaagct | ggacagggac | tgtttggtca | 1020 |
| aggcggaggc | tcctcttcat | gatcctgatt | tggacttcct | ggaggtggcc | aagaaaatcc | 1080 |
| gtgaacggaa | ggagaagatg | ctttcgaagc | cggagatggg | cagccccaga | gccctggtgg | 1140 |
| ggggctcatc | tggggtcacc | cccagcaatg | accagagtcc | ctgggaagaa | aaggccaagc | 1200 |
| tggacccaga | gccagagaag | gctgctgagt | cccccctcacc | caggctggga | aggggcctag | 1260 |
| aacttgctga | ggttaagagc | agagtggcgg | atggggaggc | cgcggcaggg | ggagagtggg | 1320 |
| cctccaggag | gagtgtcagg | aagtgcatca | gcctgtttcg | ggaggacagc | accttggcct | 1380 |
| tggcagtggg | gtctgaatct | cccctggcca | ccctgcgtc | ccatcggcg | gcaccagagc | 1440 |
| cggagaaagg | ggttgtgagc | gttcaggaac | ggatcagagg | ctggactgcc | gagagctcag | 1500 |
| aggctaagcc | cgaggtcagg | aggaggacgt | tccaggctcg | gccgctgtcg | gcggatttga | 1560 |
| ccaaattgtt | ttcaagttca | gcttccagca | acgaagtcaa | atatgagaag | agtgctgagc | 1620 |
| tgagcggcga | gttctaag | gaaccgagag | aaaagcaaaa | ggaggggcac | agtttggatg | 1680 |
| gagcatgcat | cccgagaagc | ccctggaagc | ctgggacact | ccgggataag | tccaggcaga | 1740 |
| cggagcagaa | ggttagctct | aaccaagacc | ccgacagctg | tcgcggtgga | agctcagtgg | 1800 |
| aggccccgtg | cccttctgac | gtcactccag | aggatgaccg | gagcttccag | actgtgtggg | 1860 |
| ccacagtatt | tgagcaccac | gtggagagac | acacagtggc | tgaccagtcg | gacgttgtc | 1920 |
| tctccaccac | accccctggt | gacatggccc | atgccgtgt | ctcagaaccc | aggccgaggc | 1980 |
| ctgagatggg | ctcttggctg | gcagggacc | caccagacat | gacaaaactg | aagaaagaga | 2040 |
| actccagagg | gtttgacaat | cccgagacgg | agaaattggg | accaaccacc | cttttgaatg | 2100 |
| gtgaactgag | accgtatcac | acgcctctcc | gggacaaaata | ccctttgtct | gaaaaccaca | 2160 |

```
ataataacac cttcctcaaa cacttggaaa atcctcccac atcgcagaga attgagccca    2220
gatatgacat tgtgcatgca gtgggagagc gtgtgcacag cgaggccatc tcaccggcac    2280
cggaggagaa agcggtcacg ctccgcagcc tcaggtcttg gctctcactg aaggacaggc    2340
agctgtccca ggaggtcacc cctgctgacc tggagtgtgg tttggaaggt caggcggggt    2400
ccgtccaaag ggccagtttg atttgggaag ctcgaggcat gcctgaggct agtggaccga    2460
agtttggggg caattgcccg tttcccaaat ggacaggcgg ggcagtggtg agctcgcaca    2520
aagccaccgt ggcagtcagc gaagagcact gtgctcccgg ggccacctcc gtcagggcta    2580
tcaaggctgc catctgggaa agccagcatg aggggccaga gggggccaga agcaagccag    2640
gagtgggagc aaggggccca ccccagggat gcccctcga tcctctttcc agggctacga    2700
atgggccttc tgactcccaa gcacgaacac atccagatgc atttgctgtg cagaaagggc    2760
ccttcattgt agccgccagg gagggtgatc cagggccggc ccaggtgcca cagcctgcag    2820
tcagaatgcg gaaagccggc gccatggacc agagaatgga cagatggcgg cggcggactt    2880
taccccccaa cgtgaaattt gatacattca gttctcttgt cccagaggac tctccacatg    2940
tggggcacag acgaacagat tatgtgagcc ccacagccag tgccttaaga aaacctcaac    3000
tatcccacta cagggtggag acccaggagg tgaacccagg tgcttcacgg gaccagactt    3060
ccccagcagt gaagcaaggg tcacctgtgg aacccaaggc gacatttttt gcagtcacct    3120
atcagattcc caatactcaa aaggcaaagg gtgtggttct gtcaggagct gaaagcttgc    3180
tggaacattc tagaaaaatc actccaccct cgtctcctca ttctttaaca tccactttgg    3240
tttctcttgg tcatgaagag gcattggaga tggcaggcag taaaaactgg atgaagggac    3300
gagagcatga aaatgcaagc atttttaaaaa ctctgaagcc aacagaccgt ccatcatctc    3360
ttggggcctg gagtctggac cctttcaatg gaagaatcat tgatgtggat gccttatgga    3420
gtcatcgggg atcagaagat ggccctcgtc tcaaagcaa ttggaaggaa agtgcgaaca    3480
agatgtcccc cagcggcgga gctccccaaa ccaccccgac tctgaggagt cgtccaaaag    3540
atcttcctgt gagaaggaag actgatgtga tcagtgacac gttcccaggt aaaatcagag    3600
atggctacag atccagcgtt cttgacattg acgcccctgat ggcagagtac caggagctgt    3660
cgctgaaagt ccctggggag gctcaggaga ggaggagtcc caccgtggag cccagtacgt    3720
tgcctcggga gaggcctgtt cagctgggcg gggtggagca gagaaggagg agcctgaagg    3780
agatgcccga taccgggggt ctctggaaac cggccagttc tgccgaaata aatcacagtt    3840
tcactcctgg cttaggcaag cagctggcag agaccttgga gacagccatg gcaccaaat    3900 ctagccctcc cttctgggct ctgccaccct cggctccttc tgaaaggtat ccaggggggct    3960 ctcctatacc tgcggatccc aggaaaaaaa cggggtttgc tgaggatgac agaaaggcct    4020 tgccagtaa acatcatgtt gcaaagtgtc agaattacct ggctgagtca agccctctg    4080 gtcgggagga tccaggcagt ggggtcaggg tgtcacccaa atcgccccc actgaccaga    4140 agaaagggac cccaaggaaa tccaccgggc ggggagagga ggacagtgtg cccagtggg    4200 gtgaccaccc acgtgactgt ggacgggtgc cgctggatat caagagggcc tactcagaga    4260
aggggccccc tgccaacatc cgagagggcc tgtccatcat gcatgaagcc agagagagga    4320
ggcgagagca gcccaaaggg aggcccagcc ttactggaga gaatttggag gccaaaatgg    4380 gacccctgttg gtgggagtca gggactggag acagtcacaa ggtgctgcca cgggacctgg    4440
agaaggagga tgccccccag gagaaggagc gaccgctcca gcaggtgtcc cctgtggcct    4500
```

```
cggttccctg gagaagccac agcttctgca aagacaggag gagtgggccc tttgtggacc    4560
agctgaagca gtgtttctcc cggcagccca ctgaacccaa ggacactgac accctcgtgc    4620
acgaagccgg cagccagtat gggacgtgga cagagcagtg ccagagtggg gagagcttgg    4680
ccactgagtc cccagatagc agtgccacat cgacaaggaa acagcccccc agcagccgtt    4740
tgtcttctct gtcctcccaa acggagccca cctcggcagg ggaccagtat gactgctcca    4800
ggaccagcg gagcaccagc gtggaccact ccagcactga cctggaatcc accgatggga    4860
tggaggggcc gcctccaccg gacgcctgcc ctgaaaagag agtagatgac ttctccttca    4920
ttgatcaaac ctcagtcctc gactcaagtg ccctcaagac ccgggtgcag ctcagcaaga    4980
gaagccgccg ccgggccccc atctcccact ccctccggcg cagccgattt agtgagtccg    5040
agagcagatc acctttggag gatgagactg acaacacgtg gatgttcaaa gactcaacgg    5100
aggagaaatc acccaggaag gaggagtcgg atgaggagga gacggcatcc aaagctgaga    5160
ggaccccgt cagccatcct cagaggatgc ctgcgtttcc aggcatggat ccggcagtgc    5220
taaaggctca gctgcacaag aggccagagg tggacagtcc tggcgagacc cccagctggg    5280
caccccaacc caagagcccc aagtccccct ccagcctgg ggtgctgggc agtcgcgtgc    5340
tgccttccag catggacaag gatgagaggt cggatgaacc ctctccccag tggctaaagg    5400
aattgaaatc caagaagagg caaagtcttt atgagaacca gtttgaccag ggcagggaac    5460
actgccacat ctacgtaaca gaagccttaa ccatcagaac ccgcagacga ggccgagctg    5520
ctgccgtttc ttcctgcaca acgcttacgt gcctgggccc ttcccattgg attgagaacg    5580
ctatccagtg cccctgtcct cgccaggctc tccctggatc cagacgggaa gacccaacct    5640
ccaggagcac tcgctcatct ccccagacag cacttcaggc tgggaaagga gccaggctgc    5700
ccagaaacgt ccatgtgggt ggttttgctt tttatgtaaa aatttgcatt tctacctatt    5760
ttagacacct tcatcagctc caagaacatc agtgtgaggc tggaattgtc tccccaggtt    5820
ctgaaaaaca cctgcatttg tgaaagcacc tcctcacccg accccggggc aggtcttttt    5880
ttggaaggac atttccaagg aagatcaaac tgttcatttt ctgctgtagt ctcggtgcag    5940
ggtattaccg ctgggttgag gttttctatt cttttttttt ggtgagttcc ttcttcccct    6000
tgaggaatca gcagttccaa ttttttaaaca tactctccct gattatgtgt atttctcttt    6060
ctagtggggc tgtgtgcatc gttggcctat gttattgtat gtcattttg tttgctttag    6120
aaggcgataa agcaataatt cagctaattt tctttgaaac ttgataggta tatatgtgtt    6180
tacgttaaag gacaggagga aagatgtgcg aataatttgt tctgaagtat ccagtcacct    6240
caggttatct tatccctatc caagctgttt agaagttata attgtcactc ttgtatttat    6300
ttccatggct tcttttcatt tgagctctgg tttcggtagg gtgaccttg ccccttggcc    6360
ttaagggttc ataaactgca gcccaagtgg tggtgccttt gcttatgaat catcagacct    6420
gccctagtaa tcttttttctc cagagtcttc tttgaacatg acgtgggctg ctggcatgga    6480
ggagttgttc caaactggcc tcagaacaga tgcatgaatg aagggtactt tttgcttttg    6540
ctcacctcat tttccttcat ctttcttgat gaatccatta tttgcaaatg ctgtcaaaac    6600
atgctttcct tctccctggc tacctctcag gagttcattt gtctctctgt tcagcttcc    6660
tccctcatct tcctttaccc ctcttctctg tcttagtggg tggatgggca tggatagaaa    6720
tcctctgttt ctttaggtta ggataaaac ctgggccctg gtgaggcagt tgctgttcag    6780
caccagggac agcaactgca gggctgtgag gccgagcccc accttgtgtc ctgttcgatg    6840
agctttggtt actgatgagc aattgccaga tcatgtcacc cacccagcct tttacacctg    6900
```

```
ggagcctcat gcatctgggt ttgggagttt ggccctgctg atgatagttt gttttctctt      6960
cattccctga attagtcatc agttctccgt ggccatttgg ggattcatgc ctgcaactgc      7020
ttcagtcgaa ttcttttta aagatccagt ttatgtttta taataatttt gatcttatgg      7080 cttttcaacgt caataggatc ccctttaaaa atacccctgct agtgttttgt tttgttttgt    7140
ttttctgaga caaggtctta ctctgttgct caagctggag tggagtggca cgatcatagc     7200
tcactaacac ctgggctcaa gtgattctcc cacctcagcc tcccaagtag ctgggactac    7260
aggtgtatgc taccatgacc agctaatttt taaatatttt tgtagagaca agggtcttac     7320
catgttgccc aggctggtct cgaacttctg ggctcaagca attgtccctc ctcagcctcc      7380
caaagtgctc ggattacaga catgagccac tgcacctggc ctgaaacaca ttcctagtct     7440
tttgatcctg acttcttatc tgggctgctg tctctctttc cttcaggtgg aaaggacccc     7500
ttggtaccat ctcaagcagt aggaaaggac ctgctcttac atatattgat ggtcctcatg    7560
caaaactctc aattcttaat tagtcatgtc tcagctcaag gatatcagac aggaatgaaa   7620
cacacttgaa aatgagattg acctggagat ttttttttccc taatctctca taccttaatt      7680
ggaaaaataa tcaattaatt ctatgttaat taggatatac aaagttcacc ctccttgaaa     7740
gtgactaggg caagccctga agatcttcct cacctccttt tattttttcta taaccttgtc     7800 tcctccagca ccacagggaa gacaatcaca gtgggtcaag agcgaccctc tttcacgtgg    7860
gctctgccat gacctctgag acctgcttat gatcagtgca atgaagttag aagtaactga     7920
tgattgggag cctttgcaga tagctgggca aatgggtgat ttacttatcc ccattctaaa      7980
tggagtgagc tctctttgag gctaagcaag gaggcgttgt atgctagttt ctagactttg     8040
cctggagacc ccttttggaaa tctgtcttct ttttaaactc acttaatatg ccttaatcat      8100
ctgtgtgtaa tggagtcatc cgctcctcaa tctaaccctc ctccctggg gctttggctg      8160 tcctcaatga gagtttcatg cagaatggaa aatcctctat atgtacaatc tctctccccc    8220
tcatttctct tcctcctcac ctccaccacc cctttgcaca tcagcatttt aacagctgat      8280
cttttgagaa gcctgtatct ttttcctctct cagtagatac ccttcttcat ggtcctttgc     8340
ctaatcaaac agaggctttt ggccttttgaa atccatgac aaggcctcag aaatcagtgt     8400
tgtggaggat tactccatgc caccggagaa actctggtga agagaaacc tcgtggtctt      8460 taggatgttg ggattttgag tgaacctgac ctgatagcct caggattcag ggaaaggaca     8520
atcagatggc ggtgttttcc aggggacgc gccaaatcat gtggtttcag acaattgtgt     8580
ttgcctttgt gcctccctgg aagggaggcc aactaagggt atcaccaaga agccaaaaga    8640
gaaataggca tgagcctgtg gttttaaact ttacaggctg gcaaaggat ttagaaagac      8700 ccttagcatg atttttccta aagagacctt agctgctcca acctggtgct gatagctgct     8760
ttgttgatct atgctttaaa attttctttt ataatgcccc cagatggctc ctggaactag    8820
tcgtaattgc aaactgtaaa aatccctcct ccccagtgta gatatttaaa ccagagtaag   8880
tgatggggag acattctgtg gtctctgaat gtgccttccc cctcaccgtg tgttaaaaca    8940
caaaagccga agttccatgg catcatgatt ccgagggggct ggagggatag gacccactcc    9000
acatctaaag gggatctgct ttgggctcgg tcccattagc gagtggggga ctcttgctgt     9060
gtgctaagag gctgctagga ctcacccagt tggaattctg ggtgggctca ggaagtttag    9120
agccacgtaa aaagctggta ggcatgagtg tgccaggtc ttgccagcct gcgtctcctt      9180
ttgcaccccc caatccagag tttgctttct tttgactaaa ttggctcctg caggggaag    9240
```

```
ggcagaaagc taggccctct gctctggaaa gtcggcctga ggtttccggc aagttaaccc    9300
ttaaaatgga caccCctcag cccgccctcc cctttggcct tcccagaatc tccttcagtg    9360
gttgctctca cacctgtgcc ataacatcat cttccatgac ttggacgggc acttccttga    9420
caattcctat tggcatcaca cgggctacaa attatgctgt tttctaaaga atttgaactt    9480 ttttttttt cttttcttga gacacggtct tgctctgttg gccaggctgg aatgcagtgg    9540
cacaatcata gctcactcca gcctccaact cctgggctca gcaatcctc tcatctccac     9600 ctccagagta gcctagatga caggcgcaca tcaccacgcc cagctgatct tttaaatctg    9660
ttttgtagaa acaggatctc actatattgc ccaagctggt cttaaacttg gtctcaagtg    9720
attctactgc ctcagcctcc caaagtgctg ggattacagg cctgagccac catgcccagc    9780
tgaatttgag cttttaata atctcattcc acatagcctt atagatcctg taaataggg     9840 gggtcacaaa agtaatatat tgtgttatgg aagataattt tgtactgtgc tgtttcctaa    9900
atcataccaa tatcctaaag tcatgcactt cccagatgat cgtgatcctc caaatgcttt    9960
gtaagatggg gcagggcgtg gaaatatata tatatacaca cacacacaga gacacacaca    10020
cacacaagta tagtatatat tttcctaacc tttcttctgg gtccttcctc agatctttga    10080
gtcacgatag aaaaggagct cgagttcttt gtgtaggaaa gttaagcttc ctgcctgcgg    10140
tgttcttgca attgccttag gaattcacaa gctctaggag ttctgaacgg aaggcagacg    10200
agaggcactt tatccagtcc cagaaagaat ctctaaccgt gtgactgaga agtcatctag    10260
aaaaacttat atttttaatg taaaaacaaa tggggcttac cagacctcac agagtattgg    10320
acgtctacaa gtgcttttat attttgtaac tgtaaagaag tttcatatgc acagaagagc    10380
agttggaaat ctggtcgact gcaataaaac aagatgacct ttgcatgtac aaagatgttg    10440
cattcagact atgaaaatag caaataaagc tttggtgcaa gttgcattgg                10490
```

<210> SEQ ID NO 21
<211> LENGTH: 9335
<212> TYPE: DNA
<213> ORGANISM: Homo sapiens

<400> SEQUENCE: 21

```
aaccgtcccc aacggtcgcc agcgcgcggc tcccgggccc cctcgctcct ccccctctggc    60 ccctccgagc gctgggggtg cttccctccc cgcctcctcg cactcccact cgcgggcacg    120
ccggtggctg tgccgccatg ccccaccaca ggctgctcac gggcctaggc gcggcggccc    180
gagatagggg cccctgagcc tcccggggga ggagagaggc agcgagccgc gctccgcccc    240 ctcccccgg gccgccgccg ccgccgcctc gccgcccag cctggcggga aaggaggag      300 gagcagcagg cctccgggcc cggcgccgcc gcccgcagga catttctgat ttatttgcat    360
ccttgaagag catctgtaga agaggaagta aaagatgggt gtgaaaacat ttactcatag    420
ctcctcttcc cacagccagg aaatgcttgg aaagctaaat atgctgcgaa atgatggaca    480 ttttttgtgat atcactattc gtgtccagga caaaatcttc cgggcacata aggtggtact    540
agcagcttgc agtgatttct ttcgcaccaa acttgtaggc caagccgagg atgagaacaa    600
gaatgtgttg gatctgcatc atgttacagt gactggcttt atacctcttt tagaatatgc    660
ttacacagcc actctatcaa ttaacacaga aaatattatt gatgttctag cagcagccag    720
ctatatgcaa atgttcagtg ttgccagcac ctgctcagag ttcatgaaat caagcatttt    780
atggaataca cccaacagcc aacctgaaaa gggtctagat gctggacaag aaaataattc    840
taactgcaat tttacttctc gagatgggag catttctccc gtgtcctcag agtgcagtgt    900
```

```
ggtagaaaga accattcctg tctgccgaga atcccggaga aagcgcaaaa gctacattgt    960
tatgtctcct gaaagtcctg taaagtgtgg cacacaaaca agctcacccc aggtattgaa   1020
ttcttcagct tcctactcag aaaatagaaa ccaaccagtt gactcttcct tagcttttcc   1080
ttggactttt ccttttggaa ttgatcgaag gattcagcct gagaaagtta agcaagcaga   1140
aaatacccgg actttagaat tacctggccc atctgagacc ggtagaagaa tggctgatta   1200
tgtgacttgt gagagcacaa aaactacctt gcctttaggt accgaagaag atgtccgggt   1260
caaagtagaa agattaagtg atgaggaggt ccatgaggaa gtgtcccagc ctgtcagtgc   1320
atctcagagt tcgctgagtg atcagcagac agttccagga agtgaacaag tccaagagga   1380
ccttctgatt agtccacagt cttcctctat aggctcagta gatgaaggcg tttctgaggg   1440
cttgcctaca cttcaaagca cgtctagcac taatgctcct ccggatgatg atgatcgatt   1500
ggaaaatgtt cagtatccct accaactcta cattgctcct tccaccagca gtacagagcg   1560
accaagtcca aatggtcccg acagaccttt tcagtgtcca acctgcgggg tgcgattcac   1620
ccgtattcag aacctaaagc agcacatgct catccactca ggaattaaac catttcagtg   1680
tgaccgctgt gggaaaaagt tcaccagggc ttactcgcta agatgcatc gcctaaagca    1740
tgaagtgatt tcctagtacc ggactactta aaccaggaac aagaagagac ccttgttcaa   1800
tatgatcttg gagaacacgg ttttgaaagc aactcctctg ttcaaatgcc tgtcatttca   1860
caggtctcct caacccagaa ttgtgaaagc acttttccct tggggtctct tggtgggctg   1920
gcagaaaaag aggaagaagt gccagagcag ccaaagagca gtgcttgtgc tgaggcaacc   1980
agagatgacc ccccaaaatc agagctgtct tctataacta ttgagtagtt ttgtgatttg   2040
gcttcagttt tgtttttggg aaagtgcctg tgcttggtct tgtacattta aatttaattt   2100
aatttttaa acaaaaaaag ccgggtggga gggaggggga gattgggaaa gaatttccct   2160
ttttactttc tgagccctga aactgatttt attttttccta actgagagat tgcttctgta   2220
agtacacaat aacatgatgt tgaaacagaa actatgagac ttaaggagaa ctggttgact   2280
taaaacatat accagttcct tcttccattg ttaaaagtag gctaacaaca gatcattagc   2340
tagagaggaa atcagatgat tattgacctt cttgagacaa gagggtacat gagaaactaa   2400
ttactaaaca gcttgacaaa tggcctgagt agatacttac tgctgtacac aggatgttgt   2460
ataatatttt gtaaagcctg ttgttttttgg aagtatttat ggtaagcttt cttaaaaatt   2520
attatggtaa atacttctga atccggcgt acttttcttt aagctttgtc atttctgtta   2580
tgattttca tggtgaaatt ttggtactga gatgggcatt ctctgtacct ttatagtacc   2640
actccaaagg caaggaacca tgattgacaa cagtcaagct gtggatgaaa tgaccaggaa   2700
cggagaatga agtatgtaaa tcccagcttc ataggaactc ttctcatact gcttttcaga   2760
ttaaaattgc tgtttacctg gtctccgaat gtaatgcctg actgtgtcat tgcccggatc   2820
agttttcccc ctgccccatc aatatgttct cttgcatata ttggcgtgct gccatataaa   2880
gtaaaaatac tggagatatt ctatatttta tatataggtt tatgtgttgt tggggatgtt   2940
ttcattgtgc tcttttggac ataataaata attctctatt gaggctacat tctttttttt   3000
tttctttttt tttaaaagaa tggcatctca ctctgttgcc caggctggag tatagtggct   3060
aagtcatagc tcactgcagc ttcgaactcc tgggctcagg ccattctcct gcctcagcct   3120
cttgagtatc taggattata ggcatgctcc accacctg gttaacttca ttttattt      3180
ttgtagagat gaggtctcac tatggtgccc aggctggtct tgaactccta gaccaagtga   3240
```

```
tcctcctcct ttggcctccc agactgctgg gatcactgca ccggccaagg ctgcattctt     3300
aacccaacta gattgtttac tgaatcccat atgacagcga tacattgtcc ttacatattt     3360 attttttagac attgcaaagt tattaaaaac agttaactat agtttttaca caacgtaggc    3420
aacaatgaag agtatagact gtaagatttt catctatgac tcataaatct gggagaaaaa     3480
aattattaag actaatgaga aactgaaaac cttaaactaa tgaatattat ttctgctgct     3540
aaaaatatga aactttctgg tctgtagttg aaatttgtat gatcctctag acttgggtat     3600
acttttcatc tggtgccatt aaagcatctc taatattgat cctaaatatt tgtaagtcca     3660
tgagcagtga actttggaat aagtttctgt gtagataccc aaagtttaat aattatgaga     3720
gcacctgatt tgatagacag aaaatacagt tctttagtca aaacacaaga tctgaatttt     3780
gttcaggtgc tagaccatac taaatgtata tattttaat tatagtgatt tgtttcattt       3840
ttttagattg gctaattctg taattttttc cccaaaaaca tgtgaagaaa ggaaaagtaa     3900
attaaattcc ttagaactgt tttaggttaa gattctctgt gtctgcccat attctgcagt     3960
ccttaacttg ttttcaactc tttacctcac tcatgaactt gttttaccc atttgctgcc       4020 aaacataggt gtgttccctt caggagaatc agcatataca ggttatgata ggctcccacc     4080
atttatgctt cttcactgat agggttgcat tactttctgc agcagactat aatacttcat     4140
atagtactgc tgtgtctcaa ctggaaaggt caggaatttt aatgttacgt tgtggtcttt     4200
gaaaactgtt aggcctagca atagataaat ctcaaaatta attttaaaat ctgtattgac     4260
aagaataggt aaaattatga ccaggaatca ttgttaccct tagttccaag aggtggtttt     4320
tgaaagagca agaggaaaga aaaagaaaa gaaggaaaga agaataaaga agagaaacgt      4380
gtaagaatgg tttgcagatt gattggttaa aagtgttttt agcacatccc caaccctgaa     4440
aacttcgcat taagagccaa gcacaatgtt ggtagctcca agatattctg actgtgttct     4500
cagaatgagg gattacccat cactgggtat tccttcccaa gtagaaactt tagattttca    4560
ctggtaatac acattgccaa gttttatggg aaatctgaat atactgtgaa aatgcatatc    4620
tggttagttg tctgctgccc agatcttatc aataccagta actaaccagt atttaacata    4680
aaatgataca aataaaggcc ttttctctatt tcagtgaggg tacatttttc ttgatatata   4740
tgtactttaa ggatattgga tctgtttatg gatctgtttt aggaaacaga tttgcaaggg    4800
ataattgtat atatagtagt atttaggttt atttcaaatt catcttaggg atgcctagat     4860
gcataatttt taccaggaca tattgaaaat attgcaaaga gatagccagt tatattatcc    4920
cattcattag aaaattaccag tgtaactaaa cataaatatt ccagtttaga gtgcttaaac   4980
gtagctatct ttcttaaggc caggagggta actttgtggt atctaaaggg cttaaatttc   5040
agaatgcaga ataaattgcc ttttaaaaac caagcatttt gtacaagctt ttattttcag    5100 tttttttaact accaaatagg tgtgatgtac tttagaagta aacaaagatg ttcacccatg   5160
ataatggatg ttaaagctcc tgcagttgtt cttttcgtgt ttaaagggta tattctaata   5220
gtggaagcat caaacatgtc agtgatttca tctcattcag aaataaagag attaatattg   5280 gtctttatt tttggcattt taagttttat ataaatggat gcagatggag attatcaccc    5340
acaaatatat ttaaatggat ttttcttaat ttgaatttca agtaatcttt ttatttcaag   5400
taattagtta cgcatttagt tacattgcca gtttttttt tttatcaatt tcagtaagac     5460
aaaatatact aaaatgttta aatagcctca ttcaatctta cattttgaca tttcagcaat   5520
cattctggct tacagtaatt agatcccctg ttacgacaca tgccctttgt tcttaataac   5580
tagcaaaaaa aaaaaaaaaa aaaactttc atcttgttaa aatactttgc caaatgaaat     5640
```

```
agactagtca atacatctga tgtccataat tattggtaac tcagttacct tctaactaat   5700
aggctggttc aggagactct cccagtttat aaatggttct cttgggagcc tttggaagct   5760
gtattaaatc tttcagtctt ttatttctaa ttttttctct taatctaaat agaggccagt   5820
tatctatttt atcagctttt attcttgaag attctcagat tatgttttag tcccttttag   5880
ctttaatagt ccttgaaaaa tacattactg tataatgtgg caattctgta acagagactt   5940
attacttgaa tgaataatcc taaaatttta atattttagc tgaagtttga gatttgtgga   6000
atgaacaaaa gaattagaaa ctttcatatg ttactttgtt tcagtcatct gcaaagtatg   6060
aagctgtaat tctgaaatac acatccaagt gaatgagaat taaaaatttt ctaaatatta   6120
atactaactg ggaaaaaaaa actagtgtga agtttacagt tagaagaaac agacccaaag   6180
ttgccagaag gtaataaata aatgtagttt tcactgtaag taagttattg acgtaagatg   6240
ctttatttgt aatatattta gattttgaaa gttattgaga gatgaatgta taaaagctaa   6300
atttttcttt ctgaagcagt gaaacaaaat tggggtaaca aggaagctct gttgtggcaa   6360
acatgtctat gaggaatatt aaaactaagc atactcccac aggctttaaa ctcaaactat   6420
gaacatttaa attaagttgt tccttatttt gcctataccc attttatct ttcattgtcg   6480 tttttgcttg acagtatggt gacagagtat ttttatttgg aaagtcctca gcaagatgaa   6540
ttagccaaaa gcaataatgg ttcagattaa acaataaagt ggaattgatt caatcccagg   6600
ctcaactaag aacagtcgct ctctggatgt ttcattttag acgatagata agttgagatg   6660
ttgtaatatt tatgggggt taagcctgtg tcagttatgg gatgaagact tgtagtacca   6720
gtaccatcag tggtcatact ttttttttaac ttttttactaa actaatacag ttagacattt   6780
ccactctatc gtgattatat ttttatgatg ggaaaataaa aacacttcca tgttttttata   6840 aatagtctct gcaaagattt cagatgttat tggtatctcg gtttggcagt atctgaaaaa   6900
ttgagattgt ctttgaaatg tttgtgctac ttttacttaa gtaaacccc actgtgcaag   6960 acccaggccg gcttcagcta ataccaaggt ttctgtgtgc ataatagttt acagagaact   7020
taagagtaag gactgcggat taaaaacaaa actttttta actttaaaat ttttagtttt   7080
tgttcaaagt acctggttta taaagtcaaa ttcttttatt agttcctttc tcgtttaaat   7140
tgactgatgt tgctgatgaa gcttaaagtc ccaggcacgg ttgtggcgat atactgataa   7200
aattggtgcc tagtggtggg aggagctcca gtgtcaggac ttttattaaa aggcccttgt   7260
tttcccaaat gccaatctag ccacatttag atttcattat tcaataaaac agatgaaaaa   7320
tcatcccata aatgaatgtt gaggttacca aagtacatca cctgctgagg aaggataaat   7380
cttcctgctt taagggagcc ctgtcatctc tcctcttaat gcacgtttcc cttggtatta   7440
gtggaagctg tgttcaagat gggaagcctt tcctgcagtt cttagaaaca cctgctttct   7500
aaggagagcc ttttctagga ttagcttatg tgtgttttct ctaggcgatt ttttatttca   7560
gttaccaatt taattttcaa gttgacagat gctgtgtaaa gtctctcata atgagagtag   7620
tccattaaat tgttgaaagt tgcactgctt ttcatctttc aggtacctga aatgagtgac   7680
atcaggtatt tggaaggagt aagatcataa actgtattca ttttcttcct tgtacaaagt   7740
gatgacttct aatgcttata tctcaaggta ttttttaaaa aagcaacggt ccctaataga   7800
gtaaaatttg gttttggtcc aagttcccaa taatgtattt aatgtttctg ttgtttactg   7860
gtgcctcccg ttgcatcagg tagagattgc ctgcctcttt gtagggcagc cttgtggcac   7920
cttatgtcca acttggagga tagtatatgg cttcttgtg cctctactat cttttcaaaa   7980
```

```
gccattttat aaaaatccta ggtagcctat tttaatatttt aaatatatat atttgtgaaa    8040
gaacttttag aacagacctt ttcttttttac tttaaaattc ctgtatttcc attttttaaga   8100
gtaaatttaa tctccaggat ttagaagtgt cttttccagag aagcataatg agaaagtcag    8160
actgaggtaa taagaccaga attaagtgat agaagaaact gttgtttggt taaaggacac    8220
agatttgaag gaaaaaaatt ttgatgtaac aatttttaa ataaaatttt gttttctgt      8280
aatgtcatat ttgctgctac agtagctcaa tattttacag gctaacata aagctggctc    8340
cattttaaaaa ctggagtact tcctagtgca gccagcctag gcggaaactg tacaccatgg  8400
tcttccagat gggtgactga tggctttggg tagctgatgc atgctttaat atttgcctat    8460
agcccggcag caaggaagtc ggggcggggg gacttttta ccctgccagt tatagcattg     8520
tgattctttc tgggcactgg cattttgtga aactctcaag ggaaggtgat gcaggggaga    8580
aaatgtgaat taaattacat agatgggtgt ttttatgtct tctaccccctt tcctagaatt   8640
agtacaactc ttaactgtgc cagtccccag ttcaccagct ttgtatccag tcgtcatctc    8700
attcaagtat ggctttactt ggtgacactg gccatagcta agttaacttg gcatgtttga    8760
cttttgacaa taacaaaaat ggttttggat tttgtttttat ttccaaaaaa tgtatacaat   8820
atcagaactt cacatttttat atactagtat ctggctatta gtattttaca ggaaccatag   8880
ttcttggtga ctacatatat atatatatttt ttgtgacctt ttttgtaaac taagtgccgt   8940
ttcaacgtta caatcatttt tagggttatt gtaatcaatg tgaatatcat gttttttcaa    9000
atctgttctg agcctatagt gtttgctttg tgaacatgtg tattgtatat attctgtata    9060
gttatattgt actgaaatta gcttgtttga tataaggaaa atatgtattg agtacctttt    9120
tgctagcctg attgtttaat ctttttaaaa aaggttttaaa cttttttttaa aaaaaaaatc  9180
tttaaactgg cctttattac atggtcacac ataaagttgc agttaggaaa gggatgggca    9240
gggaaaaact agttttgagt gtctttagat agaaacatga gactaaggtt tgattttgtt    9300
ttcgttttct cattaaaata tcttatgctt tatgg                               9335
```

<210> SEQ ID NO 22
<211> LENGTH: 942
<212> TYPE: DNA
<213> ORGANISM: Homo sapiens

<400> SEQUENCE: 22

```
gagaacttcg ggaggcgggg gaggaaagcg gccggcgagc gctggctgac attttcctgc     60
ccggaaggat gcatggcccg gggtctcctg cacctgaggg tgggcgggag gcggccccgc   120
gggttgtgtt gctggaaaaa ggggtctcga tccagacccc aagagagggt tcttgggtct   180
acttcaggga agaattggag gcgagtcaca gagcgcagtg aaggaagcaa gtttattgga   240
atctactccg ttagagagtg caagtcctca gactgcagga ggaggaactc ccgtccttcg   300
gtagtgtcac tacttagagg cagctgtgag gagctgtgat taatcgtgga atgtgctgat   360
gtgcccacta aagatgcctg gtaagcagtg gctcctctaa caagtgggca gcttggaact   420
gggaacgaga gagccaccga aacagaatga gggagacaaa gaagtgggca tcacccttaa   480
ctccacaagg gcttcccaag ggcgctgtac cgtacgcagg cccaggacga actttatttc   540
tcgccccagc atcgctgtcc ttgtcggtga ccctggct ttagggcaga caggaccacg    600
tttcataagt tcatgctgtc ccagcagagg aataacgcca gaaagtgttc cagtacaacc   660
agagaaagag agtccatgag aaatctgccc ttgtgaagtt ggaatcccct caacctcacc   720
ccgctgactt gaatgaagcg actgagacgg gctatgatgg agcagatccg gttgctcgac   780
```

```
cttctcccct gcaccaacac atgtagttaa tagttactgg acatgcatat tcagtgggtt      840
ccaggtacca aacttgtatt gaatggtatg tgccagacac cgtcttgaga tctggagaat      900
aaaaaaataa aaaaataaaa acgagacatc cagagcacag ta                         942

<210> SEQ ID NO 23
<211> LENGTH: 688
<212> TYPE: DNA
<213> ORGANISM: Homo sapiens

<400> SEQUENCE: 23
gagaacttcg ggaggcgggg gaggaaagcg gccggcgagc gctggctgac atttcctgc       60 ccggaaggat gcatggcccg gggtctcctg cacctgaggg tgggcgggag gcggccccgc     120
gggttgtgtt gctggaaaaa ggggtctcga tccagacccc aagagagggt tcttgggtct     180
acttcaggga agaattggag gcgagtcaca gagcgcagtg aaggaagcaa gtttattgga     240
atctactccg ttagagagtg caagtcctca gactgcagga ggaggaactc ccgtccttcg     300
gtagtgtcac tacttagagg cagctgtgag gagctgtgat taatcgtgga atgtgctgat     360
gtgcccacta agaggaata acgccagaaa gtgttccagt acaaccagag aaagagagtc      420
catgagaaat ctgcccttgt gaagttggaa tcccctcaac ctcaccccgc tgacttgaat     480
gaagcgactg agacgggcta tgatggagca gatccggttg ctcgaccttc tcccttgcac     540
caacacatgt agttaatagt tactggacat gcatattcag tgggttccag gtaccaaact     600
tgtattgaat ggtatgtgcc agacaccgtc ttgagatctg gagaataaaa aaataaaaaa     660
ataaaaacga gacatccaga gcacagta                                         688

<210> SEQ ID NO 24
<211> LENGTH: 1444
<212> TYPE: DNA
<213> ORGANISM: Homo sapiens

<400> SEQUENCE: 24
ggagaagggg tggggcaggg tatcgctgac tcagcagctt ccaggttgct ctgatgatat      60
attaaggctc ctgaatccta agagaatgtt ggtgaagatc ttaacaccac gccttgagca     120
agtcgcaaga gcgggaggac acagaccagg aaccgagaag ggacaagcac atggaagcca     180
gcccagcatc cgggcccaga cacttgatgg atccacacat attcacttcc aactttaaca     240
atggcattgg aaggcataag acctacctgt gctacgaagt ggagcgcctg acaatggca      300 cctcggtcaa gatggaccag cacagggggt tctacacaa ccaggctaag aatcttctct     360
gtggctttta cggccgccat gcggagctgc gcttcttgga cctggttcct tctttgcagt     420
tggacccggc ccagatctac agggtcactt ggttcatctc ctggagcccc tgcttctcct     480
ggggctgtgc cggggaagtg cgtgcgttcc ttcaggagaa cacacacgtg agactgcgta     540
tcttcgctgc ccgcatctat gattacgacc cctatataa ggaggcactg caaatgctgc      600
gggatgctgg ggcccaagtc tccatcatga cctacgatga atttaagcac tgctgggaca     660
cctttgtgga ccaccaggga tgtcccttcc agccctggga tggactagat gagcacagcc     720
aagccctgag tgggaggctg cgggccattc tccagaatca gggaaactga aggatgggcc     780
tcagtctcta aggaaggcag agacctgggt tgagcagcag aataaaagat cttcttccaa     840
gaaatgcaaa cagaccgttc accaccatct ccagctgctc acagacgcca gcaaagcagt     900
atgctcccga tcaagtagat ttttaaaaaa tcagagtggg ccgggcgcgg tggctcacgc     960
```

```
ctgtaatccc agcactttgg aggccaaggc gggtggatca cgaggtcagg agatcgagac    1020
catcctggct aacacggtga aaccctgtct ctactaaaaa tacaaaaaat tagccaggcg    1080
tggtggcggg cgcctgtagt cccagctact ctggaggctg aggcaggaga gtagcgtgaa    1140
cccgggaggc agagcttgcg gtgagccgag attgcgctac tgcactccag cctgggcgac    1200
agtaccagac tccatctcaa aaaaaaaaaa accagactga attaatttta actgaaaatt    1260
tctcttatgt tccaagtaca caatagtaag attatgctca atattctcag aataattttc    1320
aatgtattaa tgaaatgaaa tgataaattttg gcttcatatc tagactaaca caaaattaag    1380
aatcttccat aattgctttt gctcagtaac tgtgtcatga attgcaagag tttccacaaa    1440
cact                                                                 1444
```

<210> SEQ ID NO 25
<211> LENGTH: 1478
<212> TYPE: DNA
<213> ORGANISM: Homo sapiens

<400> SEQUENCE: 25

```
ggcctccctg ccacggggat gctgcctttt ctgctccggg tgtttccacg aggcaggcat      60
ggaatcttcc ctggacaagc gacataccgt ggagagacag gctcctgaat cctaagagaa     120
tgttggtgaa gatcttaaca ccacgccttg agcaagtcgc aagagcggga ggacacagac     180
caggaaccga aagggacaa gcacatgaaa gccagcccag catccgggcc cagacacttg      240
atggatccac acatattcac ttccaacttt aacaatggca ttggaaggca taagacctac     300
ctgtgctacg aagtggagcg cctggacaat ggcacctcgg tcaagatgga ccagcacagg     360
ggctttctac acaaccaggc taagaatctt ctctgtggct tttacggccg ccatgcggag     420
ctgcgcttct tggacctggt tccttctttg cagttggacc cggcccagat ctacagggtc     480
acttggttca tctcctggag cccctgcttc tcctggggct gtgccgggga agtgcgtgcg     540
ttccttcagg agaacacaca cgtgagactg cgtatcttcg ctgcccgcat ctatgattac     600 gacccctat ataaggaggc actgcaaatg ctgcgggatg ctggggccca agtctccatc      660
atgacctacg atgaatttaa gcactgctgg gacaccttttg tggaccacca gggatgtccc    720
ttccagccct gggatggact agatgagcac agccaagccc tgagtgggag gctgcgggcc    780
attctccaga atcagggaaa ctgaaggatg ggcctcagtc tctaaggaag gcagagacct    840
gggttgagca gcagaataaa agatcttctt ccaagaaatg caaacagacc gttcaccacc    900
atctccagct gctcacagac gccagcaaag cagtatgctc ccgatcaagt agatttttaa    960
aaaatcagag tgggccgggc gcggtggctc acgcctgtaa tcccagcact ttggaggcca   1020
aggcgggtgg atcacgaggt caggagatcg agaccatcct ggctaacacg gtgaaaccct   1080
gtctctacta aaaatacaaa aaattagcca ggcgtggtgg cgggcgcctg tagtcccagc   1140
tactctggag gctgaggcag gagagtagcg tgaaccgggg aggcagagct tgcggtgagc   1200
cgagattgcg ctactgcact ccagcctggg cgacagtacc agactccatc tcaaaaaaaa   1260
aaaaaccaga ctgaattaat tttaactgaa atttctctt atgttccaag tacacaatag    1320
taagattatg ctcaatattc tcagaataat tttcaatgta ttaatgaaat gaatgataa     1380 tttggcttca tatctagact aacacaaaat taagaatctt ccataattgc ttttgctcag   1440
taactgtgtc atgaattgca agagtttcca caaacact                           1478
```

<210> SEQ ID NO 26
<211> LENGTH: 3680

<212> TYPE: DNA
<213> ORGANISM: Homo sapiens

<400> SEQUENCE: 26

```
attcagcttt tgggtgaaga cggaggcggg ttctggacag acgtacgctg tcagggagtg      60
tttacttcgc ctccacttct gttcctcccc gccctggtgc tgctccgggt cacatactcg     120
tcctgagccg gcttcagcct ctctgcgcag aagtgtcccg gagccatggc cgagtaatct     180
tatgcgaagt ctaccaagct tgtgctcaag ggaaccaaga cgaagaggtg ggtcctgcac     240
ctccggcggg agcctcctca gttcttttcg gacgcactcc accccctcg aatccggtgg      300
aagccgtggc gcggagagcc ggctttgtgg cctcccaggc tttgccctgg ccctgtccg      360
ggctggactg aggccggacc gcggttcctg gcgcctgtgc agagaggggc agcctcccgc     420
actgacgacc ctggaaacag gatagacggg cgggtgaccc gtggccccgt acccacgagt     480
ttcggtcctc tgaggcatct ctgcaggcct ctgcctgtaa gaagaaaaag agcaaagaga     540
agaagagaaa aagagaagaa gatgaagaaa cccagtttga tatgttggaa tctggtgaac     600
agtaacaaac tttgatgaaa tttcaggaac catagccatt gaaatggatg agggaaccta     660
tatacatgca ctcgacgatg gtcttttac cctgggagct ccacacaaag aaggggaaaa      720
tggctttgtt ggcctcaaat ggctgcttta ttagatgcaa tgaagcaggg gacatagaag     780
caaaaagtaa aacagcagga gaagaagaaa tgatcaagat tagatcctgt gctgaaagag     840
aaaccaagaa aaaagatgac attccagaag aagacaaagg aaatgtcaaa caatgtgaaa     900
tcaattatgt aaagaaattt cagagcttcc aagagcacaa acttaaaata agtaaagaag     960
acagtaaaat tcttaaaaag gctcagaaag atggattttt gcatgagacg cttctggaca    1020
gagtcgcagt catagcctgc cttcatctct gaagggacca ggtaacacac ggagtgcctt    1080
ggcagcctca tcattgcatg caatcttcac agacaatatc tcactgcagc cacctttctg    1140
caggagtaca ggtgtgacat tatactgatg acatcattct cagagaaaat tcattttaca    1200
cactgaagat acacagacac aaagagcctt atacaaaggg aatggacctt tccccaacac    1260
agtagtgcaa ggccctgcca ctttgcttca attcctgaaa attccttggt aaacttgggg    1320
ctgctctatt cctgacactt tcaagaaata gttattcatc ctctcagcat ccacaacgtt    1380
aatacaagcc caacattctc taatttgtgt tttgttttt ggagacacag tcttgctctg     1440
tcacacaggc tggtatgaag tggcatgatc tcagctcact gcagccttga cctcccgacc    1500
tcaagcaatt ctcccatttc agctttccaa gtagctagga ctacaggtgt gtgccacgac    1560
actcagttaa ttttgtttat tttttgtag agaaaagctc tcgctatgtt acccgggctg     1620
gtctcgaact cctgggctca agagatcctc tggcctccgc ctcccaaagt tctgggatta    1680
caggtgtgag tccatgtgcc cagcccttta attcttact tggggttcag gtgactacat      1740
atttcttact tacaaatttt acttaatctc gctgatgctg tcacttgaaa gctgacccac    1800
cttgaatgaa gcctcctcca acaagtctgg aatccatccg aatttaaatt aacaggcgct    1860
cctatgaatt ccatcagaga acacacagta gatgctttag caacctcttc ccatgcctcc    1920
gaagtatctg gtttgcattg tggtggccat tagtcatcca tgggcttctg atgtaaaaaa    1980
caaacctgcc tcttttgacc ctgtgctgta cagcatcagg gcagtgattg ctggccacat    2040
actggaccct tgaaacagag ggctctgcat ccatgtccat gagccttcat gcccatctgg    2100
ccatcaggcc ttgggaagca gcaccccaca gctttggcac agctgcagtg acctccttgc    2160
ctccgaatgg agtcaaatgt gtacacgctg caattctcat ctgcaggaag cactggcctc    2220
```

```
cttcatcctt aggctatagt gctgacactg gcctccttca tcctcagact gtggtgccgg   2280
atgtcacccc tctgcgaggc ccttgggatc gactgagtga ccagcagtga agttcgtcag   2340
ccttctgaat ggatgccatg atcagatgtg atggagctca gtgggatgct gctgctttcc   2400
ctcccttagc taggatgtcc ctgataaagg atgacaccca agcctcagca caactggcca   2460
aacttgaggt ggtcatcata gcactgatgc tgggccaaca attagcccca tttgtacctt   2520
tttacaaact ttttgacaat tgccaagaat cgtccacctt ccctcccat tgaattaaat   2580 acacttcttg tctcatggat actcagaata ccaatcaagg taacagatgc ctttatttta   2640
actaaggaca cagtcacagat ctcacaggga cactccttat cccttgcaga gttccagaca   2700
ctactgatgg tcaccaaagc aacatttcat cagaaaacac agtgctgggc ttgtgaagaa   2760
ggtgtccagc agagcttcca ctgcccctgt aggctgcagg cagctgcttc agttgagaga   2820
tacactgagc tcctcaaaga attcctattt aaggtacaaa gcagcgactg gatgccctgc   2880
tggattccac tattgccaca ggctttgata actctaagtt catgctcctt aggaaagtgc   2940 acttttaca ccaatgttag acagttccct cagttgcctt tactggacat caaggagttc   3000 acattttga caatctttca gtcctgaact gtccaagggg tggaggtagc tccatacagg   3060
aagctgcctg ctgcgtgtgg atcagtaata tcagacttgc ccaacagctc actggagaca   3120
tcaaaaccaa tgcatggggg atgcatgacg tcacccaaat atttaccaca cgcttttgct   3180
gccagagacc ccagatcact tttcctgcct cctgctaaac aaatgggagc agtagcttct   3240
catcagcctc cacatttcat tactcataat tgtggccttc ctaatgtctc atgcccctaa   3300
gcacttatta caatgtctca acagccttct ctcagcctct caaatatta gtcatcatta   3360 aaataaatgt ctgatgttaa agcatcaggg tcaattgtac tgtgacacct aaaatttcat   3420
gctgcatccc accaggtcct cagcctaatg ctttcatgc ccccaacaga ctgctaaact   3480
ctttgaatta gtcaagcata tccctcaagg acaaggggt taccccaccc tctgatttct   3540
accaagcctg cctcccgcac cctgtgctcc agagtgaacc cccgggtaga cctgcacaga   3600
tgcagtgtca tccctgttg ggctgagtat gcgagatgaa taaattacgg tgaatttcgt   3660 ctaaaaaaa aaaaaaaaa                                                  3680

<210> SEQ ID NO 27
<211> LENGTH: 4010
<212> TYPE: DNA
<213> ORGANISM: Homo sapiens

<400> SEQUENCE: 27
gttcttcttt ctacctttct aagattccac catgttgctt gtttagttca accagtgctg     60
atagggacac gtttgcactt gtctctcagt gaacattcgc aagagatttt ctaggcctcc    120
aggcagaagc cgctgctgac ggggagagtc tgctggagga agtcacatgg cagatgccag    180
aggaccagcc tggagaggc tttctagcaa ccaggacacc tgccgcagtg ccacgctttc     240
tccaggaaac aaggacagct gcacgggtgc ccacacgaga gtcggcgacc agcctcggcg    300
gtggggttcc tgcaacgcgt gttcctgctg gggttctcct ttctgctgtt ccgagctaca    360
gtgcggatca tgctccccat acgtggagtc cagggacagc acagcccggg gactgccag    420 ccagccagga agtctggctt tcagagaact gggaagacca tcttccactt tatcccatct    480
gggagactgt aaacatggat tccactgtct cggacagtga gacgattccc agtcttttcc    540
tgttcctcct ctaggtatgt agctgctatc agcttccaga aacgctggaa ggaagggcgt    600
tgctttggca ggacacgtgg ggagatgggc tgggagggga gatcccggag gtaaggaggg    660
```

```
gaggctttcc tctccccaca ctgggaactc agtttctagc cccaggttcc tggttgtgtc    720
cggcatccca ggagcatgag tgggaagctg ctgcatccac ctgccgtgtg cagtcgggga    780
ccagctgcag agcgcactat gcatccttta gactctgcag gctcaagtga aacccagct    840 ctgccactgc tctctggatg accttgccac ctccctctcc tcctttgaaa agtgtgggaa    900
atgctgcttt tcatcaagtc caagtcacca tgtattgtgg cttaaacggc agtgttattt    960
tctttctcag tgacacataa catactgctg cgttttttaa cagatgctgt cttggacgca   1020
gtgaagtctg ccgatggctg tttcagagcc gttaggatgg tgaagtgaga caatgtgaat   1080
ggagtgtttt gtgaggctca gtgctgcata aatgctagcc attatctaat agcaagaatt   1140
ccttgaaatg tttctttctc tcaaatttat gaaaagatta gaaatagtt ctaaaaatta   1200 aaaatgcttc tggtcggagc ggcttacatg atggcagtga agtgtgcag cttcatgggt   1260 cccactgcgt gcacttggca tggagagaac gaaatgtgga ggccagcgat accaagaaca   1320
cccctgtgag ccgcgctggg tgcagccccc acggccggcg ggcagtgaca ccgcagtttc   1380
ctctcctgcc ggcatccacg cttcctgtgc ccaggtgctg gaagctcagt cttcatgtcc   1440
ccttctcagt tatgtgtctg tagggctggg acagggaagg aagtcagtga agctggttgg   1500
atcttccaag ggatgctctg tgtgcaaggc tcggggacaa ggatggctgg gggagtcaga   1560
ctgtcagtga agctgagggg cggatggagc ctcaccacgc tgagtccct gttttccagc   1620 tgcagatgct gaccctccag agctttgttt accagcccct gtgactgcga tctggagtca   1680
gccaggcgtt cctccttgtc cggtagattt tattaagtgc tcaatgtgtg ccaagccaaa   1740
tgtccgtttg acttactgca tgtccgagaa gcgatgccgt tgaaggaatt tcctcccaa   1800 gcctgaagga attgaacacc aggaatgact ggaaccctgg agagagagaa ctggatttct   1860
ggaggaaaat cactcgtttt aaggaagcag catcctggac ccttgaggcc ctggaggaag   1920
cgggcagcac agctcggagg cgggtgtggc tggaggacgg ccgtcgcacc tgcgaaattc   1980
tgtctgtggt acgtggttcc ttcctggctc tgggaaccac ctggatactt gcattcttcc   2040
cttttccttt ctattctctt tcaagtcacc ctccttgaga cagccctcca gtccaggcca   2100
aatctcagcc tgcccttggt ccgctgtggt tgggcctgca cccaagccat gagcacacgc   2160
agcaattgtg gcagcagaag cttcctctgg gctcagactc aggctgatgc tgcgtcagga   2220
cctgccgcgg tctcggctgg gcttcctggg actcggtggt gtgggctga ttgtaaagca   2280 cggaatgact cttagaaact gggcgtcatt cttttgtggtt ttccaagctt ggtctctgat   2340
gatactccag gtcttaggag acatgctgaa tatttattat gcttacattc aagcaacatt   2400
aacccttaag gttgatgtag ctccccgtct tttttccca gaaggaggag cactgaagga   2460 acactttttcc agtatggatt cttttccagct ccgagaagct ggaggcacac ggatccctcg   2520
gccagctctc atctatggac gtgctgtagt cacaaggact gtgactaagg ctcagtccct   2580
gaagagtgcc ttggcatggg ctgctttagg ctgtaaacac ccagtttat ccactttatg   2640 tgaagaaagc caacaagggg catggagtga gttccgcagg ttttagtggc tgcggaggct   2700
ggtgctcagt ggggatgatg gagggaaggc gcctccctct gcgggccccg aggtctgtgc   2760
gggaatcagc tctgcagttg tgtccagggg cagccgtaga ccacacacgg caggctcaca   2820
gctctgttcc atgagaactt tatacacaaa agcagacggg ctggcttggc ctctggatca   2880
taatctgctg accccctgggg caacgttggc tgcagcggag atggctgctc cccgtgggg   2940 tgtgtgctca gcccgcagcc cccgccctcc ggactccgtt cgcctctgct ctcagctttg   3000
```

-continued

```
cacctcgtca ttgtcttcta attgtgcatc cctggactgc gtgacctaca aggctctcag    3060
cacaacaaga ctctatgatt ctgtctattg aacaaaaag ccagtgaggc aagtgtatca     3120
tcctgttgat gaattcacag aattaactct gggagttggg acagtttgt attcttcttc     3180 cagacactct ctgtttctgc tggatggaaa ggttctgcta cttgtcctgt ggtcaggccc    3240
agctgatgga atggaatgga agtgactcag ccccttactg gcagaaactt taaaagccgc    3300
acaacattcc tgcaccctcc cctctgccat gagcctggca gtgctcagga tgggaaaatt    3360
atttcacctg ggcctgagga tacaggagct actcccagcg tgcagtggaa gagaagcatg    3420
ggcaagtaat taaactttgt gttttcaagc cacagaggtt ttttgaggtt gtttgctacc    3480
atgctttgtc cctacaaaca cagtcatgga aaggccagt ggcagagcct gagccgttcg     3540
tgcatctgtt caccagcatc cagaataaca atagattttt gaaacattcc tgagaaaatt    3600
ctgggagttg cataccggcc agtcttattc cctaaagttg ttccttctaa agggtgggat    3660
gaccaaaaat ttcagaaaag caaaccaccg ctgaaaggca acgttatttc tgttggcaga    3720
aggcggcctg agcaatctag attttccacg gttcaccaac tagttttaa ggaaatatgg      3780 ctgtgagagg aataaaacat aattcctacc tttaaggaac tcagagaagt gaattaaagg    3840
aagtcacaga tcaggcaacc aaccacacaa agtttctaag agcaaactgt tcaggtcggc    3900
aagtcactct tatccactgt tttgccttct gaggtttcag ttactctcag tcagtcatgg    3960
tccaaaaaca ttaaatgaaa aattccagaa ataaacaatt cacacgtttt               4010
```

<210> SEQ ID NO 28
<211> LENGTH: 1042
<212> TYPE: DNA
<213> ORGANISM: Homo sapiens

<400> SEQUENCE: 28

```
gaaacccgga agtggaactc tgagccattc agcgtttggg tgaagacgga ggcgggttct      60
acagagacgt aggctgtcag ggagtgttta tttcgcgtcc gcttctgttt ctccgcgccc     120
ctgtgctgcc ccgactcaca tactcgtcca gaaccggcct cagcctctcc gcgcagaagt     180
ttcccggagc catggccgag tactcctacg tgaagtctac caagctcgtg ctcaagggaa     240
ccaagacgaa gagtaagaag aaaaagagca agataagaa agaaaaaga gaagaagatg       300 aagaaaccca gcttgatatt gttggaatct ggtggacagt aacaaacttt ggtgaaattt     360
caggaaccat agccattgaa atggataagg gaacctatat acatgcactc gacaatggtc     420 ttttttaccct gggagctcca cacaaagaag ttgatgaggg ccctagtcct ccagagcagt    480
ttacggctgt caaattatct gattccagaa tcgccctgaa gtctggctat ggaaaatatc     540
ttggtataaa ttcagatgga cttgttgttg ggcgttcaga tgcaattgga ccaagagaac     600
aatgggaacc agtctttcaa aatgggaaaa tggctttgtt ggcctcaaat agctgcttta    660
ttagatgcaa tgaagcaggg gacatagaag caaaaagtaa aacagcagga gaagaagaaa    720
tgatcaagat tagatcctgt gctgaaagag aaaccaagaa aaaagatgac attccagaag    780
aagacaaagg aaatgtaaaa caatgtgaaa tcaattatgt aaagaaattt cagagcttcc    840
aagaccacaa acttaaaata agtaaagaag acagtaaaat tcttaaaaag gctcggaaag    900
atggattttt gcatgagacg cttctggaca ggagagccaa attgaaagcc gacagatact    960
gcaagtgact gggattttg tttctgcctt atctttctgt gttttttct gaataaaata      1020 ttcagaggaa atgcttttac ag                                            1042
```

<210> SEQ ID NO 29
<211> LENGTH: 5460
<212> TYPE: DNA
<213> ORGANISM: Homo sapiens

<400> SEQUENCE: 29

```
agagtcaact ctgccccgag gcctagcttg gccagaaggt agcagacaga cagacggatc      60
taacctctct tggatcctcc agccatgagg ctgctctggg ggctgatctg ggcatccagc     120
ttcttcacct tatctctgca gaagcccagg ttgctcttgt tctctccttc tgtggttcat     180 ctggggggtcc ccctatcggt gggggtgcag ctccaggatg tgccccgagg acaggtagtg    240
aaaggatcag tgttcctgag aaacccatct cgtaataatg tcccctgctc cccaaaggtg    300
gacttcaccc ttagctcaga aagagacttc gcactcctca gtctccaggt gcccttgaaa    360
gatgcgaaga gctgtggcct ccatcaactc ctcagaggcc ctgaggtcca gctggtggcc    420
cattcgccat ggctaaagga ctctctgtcc agaacgacaa acatccaggg tatcaacctg    480
ctcttctcct ctcgccgggg gcacctcttt ttgcagacgg accagcccat ttacaaccct    540
ggccagcggg ttcggtaccg ggtctttgct ctggatcaga agatgcgccc gagcactgac    600
accatcacag tcatggtgga gaactctcac ggcctccgcg tgcggaagaa ggaggtgtac    660
atgccctcgt ccatcttcca ggatgacttt gtgatcccag acatctcaga gccagggacc    720
tggaagatct cagcccgatt ctcagatggc tggaatcca acagcagcac ccagtttgag    780
gtgaagaaat atgtccttcc caactttgag gtgaagatca cccctggaaa gccctacatc    840
ctgacggtgc caggccatct tgatgaaatg cagttagaca tccaggccag gtacatctat    900
gggaagccag tgcaggggggt ggcatatgtg cgctttgggc tcctagatga ggatggtaag    960
aagactttct ttcgggggct ggagagtcag accaagctgg tgaatggaca gagccacatt   1020
tccctctcaa aggcagagtt ccaggacgcc ctggagaagc tgaatatggg cattactgac   1080
ctccaggggc tgcgcctcta cgttgctgca gccatcattg agtctccagg tggggagatg   1140
gaggaggcag agctcacatc ctggtatttt gtgtcatctc ccttctcctt ggatcttagc   1200
aagaccaagc gacaccttgt gcctgggggcc cccttcctgc tgcaggcctt ggtccgtgag   1260
atgtcaggct ccccagcttc tggcattcct gtcaaagttt ctgccacggt gtcttctcct   1320
gggtctgttc ctgaagtcca ggacattcag caaaacacag acgggagcgg ccaagtcagc   1380
attccaataa ttatccctca gaccatctca gagctgcagc tctcagtatc tgcaggctcc   1440
ccacatccag cgatagccag gctcactgtg gcagccccac cttcaggagg ccccgggttt   1500
ctgtctattg agcggccgga ttctcgacct cctcgtgttg gggacactct gaacctgaac   1560
ttgcgagccg tgggcagtgg ggccacccttt tctcattact actacatgat cctatcccga   1620
gggcagatcg tgttcatgaa tcgagagccc aagaggaccc tgacctcggt ctcggtgttt   1680
gtggaccatc acctggcacc ctccttctac tttgtggcct tctactacca tggagaccac   1740
ccagtggcca actccctgcg agtggatgtc caggctgggg cctgcgaggg caagctggag   1800
ctcagcgtgg acggtgccaa gcagtaccgg aacgggggagt ccgtgaagct ccacttagaa   1860
accgactccc tagccctggt ggcgctggga gccttggaca cagctctgta tgctgcaggc   1920
agcaagtccc acaagcccct caacatgggc aaggtctttg aagctatgaa cagctatgac   1980
ctcggctgtg gtcctggggg tgggacagt gcccttcagg tgttccaggc agcgggcctg   2040
gccttttctg atgagaccca gtggaccctta tccagaaaga gactaagctg tcccaaggag   2100
aagacaaccc ggaaaaagag aaacgtgaac ttccaaaagg cgattaatga gaaattgggt   2160
```

```
cagtatgctt ccccgacagc caagcgctgc tgccaggatg gggtgacacg tctgcccatg    2220
atgcgttcct gcgagcagcg ggcagcccgc gtgcagcagc cggactgccg ggagcccttc    2280
ctgtcctgct gccaatttgc tgagagtctg cgcaagaaga gcagggacaa gggccaggcg    2340
ggcctccaac gagccctgga gatcctgcag gaggaggacc tgattgatga ggatgacatt    2400
cccgtgcgca gcttcttccc agagaactgg ctctggagag tggaaacagt ggaccgcttt    2460
caaatattga cactgtggct ccccgactct ctgaccacgt gggagatcca tggcctgagc    2520
ctgtccaaaa ccaaaggcct atgtgtggcc accccagtcc agctccgggt gttccgcgag    2580
ttccacctgc acctccgcct gcccatgtct gtccgccgct ttgagcagct ggagctgcgg    2640
cctgtcctct ataactacct ggataaaaac ctgactgtga gcgtccacgt gtccccagtg    2700
gaggggctgt gcctggctgg gggcggaggg ctggcccagc aggtgctggt gcctgcgggc    2760
tctgcccggc ctgttgcctt ctctgtggtg cccacggcag ccgccgctgt gtctctgaag    2820
gtggtggctc gagggtcctt cgaattccct gtgggagatg cggtgtccaa ggttctgcag    2880
attgagaagg aaggggccat ccatagagag gagctggtct atgaactcaa ccccttggac    2940
caccgaggcc ggaccttgga aatacctggc aactctgatc ccaatatgat ccctgatggg    3000
gactttaaca gctacgtcag ggttacagcc tcagatccat ggacactttt aggctctgag    3060
ggggccttgt caccaggagg cgtggcctcc ctcttgaggc ttcctcgagg ctgtggggag    3120
caaaccatga tctacttggc tccgacactg gctgcttccc gctacctgga caagacagag    3180
cagtggagca cactgcctcc cgagaccaag gaccacgccg tggatctgat ccagaaaggc    3240
tacatgcgga tccagcagtt tcggaaggcg atggttcct atgcggcttg gttgtcacgg    3300
gacagcagca cctggctcac agcctttgtg ttgaaggtcc tgagtttggc ccaggagcag    3360
gtaggaggct cgcctgagaa actgcaggag acatctaact ggcttctgtc ccagcagcag    3420
gctgacggct cgttccagga cccctgtcca gtgttagaca ggagcatgca gggggggttg    3480
gtgggcaatg atgagactgt ggcactcaca gcctttgtga ccatcgccct tcatcatggg    3540
ctggccgtct tccaggatga gggtgcagag ccattgaagc agagagtgga agcctccatc    3600
tcaaaggcaa actcattttt gggggagaaa gcaagtgctg ggctcctggg tgcccacgca    3660
gctgccatca cggcctatgc cctgacactg accaaggcgc ctgtggacct gctcggtgtt    3720
gcccacaaca acctcatggc aatggcccag gagactggag ataacctgta ctggggctca    3780
gtcactggtt ctcagagcaa tgccgtgtcg cccacccgg ctcctcgcaa cccatccgac    3840
cccatgcccc aggccccagc cctgtggatt gaaaccacag cctacgccct gctgcacctc    3900
ctgcttcacg agggcaaagc agagatggca gaccaggctt cggcctggct cacccgtcag    3960
ggcagcttcc aagggggatt ccgcagtacc caagacacgg tgattgccct ggatgccctg    4020
tctgcctact ggattgcctc ccacaccact gaggagaggg gtctcaatgt gactctcagc    4080
tccacaggcc ggaatgggtt caagtcccac gcgctgcagc tgaacaaccg ccagattcgc    4140
ggcctggagg aggagctgca gttttccttg ggcagcaaga tcaatgtgaa ggtgggagga    4200
aacagcaaag gaaccctgaa ggtccttcgt acctacaatg tcctggacat gaagaacacg    4260
acctgccagg acctacagat agaagtgaca gtcaaaggcc acgtcgagta cacgatggaa    4320
gcaaacgagg actatgagga ctatgagtac gatgagcttc agccaaggga tgacccagat    4380
gcccctctgc agcccgtgac acccctgcag ctgtttgagg tcggaggaa ccgccgcagg    4440 agggaggcgc ccaaggtggt ggaggagcag gagtccaggt gcactacac cgtgtgcatc    4500 tggcggaacg gcaaggtggg gctgtctggc atggccatcg cggacgtcac cctcctgagt    4560
```

```
ggattccacg ccctgcgtgc tgacctggag aagctgacct ccctctctga ccgttacgtg    4620
agtcactttg agaccgaggg gccccacgtc ctgctgtatt ttgactcggt ccccacctcc    4680
cgggagtgcg tgggctttga ggctgtgcag gaagtgccgg tggggctggt gcagccggcc    4740
agcgcaaccc tgtacgacta ctacaacccc gagcgcagat gttctgtgtt ttacggggca    4800
ccaagtaaga gcagactctt ggccaccttg tgttctgctg aagtctgcca gtgtgctgag    4860
gggaagtgcc ctcgccagcg tcgcgccctg gagcggggtc tgcaggacga ggatggctac    4920
aggatgaagt ttgcctgcta ctaccccgt gtggagtacg gcttccaggt taaggttctc     4980
cgagaagaca gcagagctgc tttccgcctc tttgagacca agatcaccca agtcctgcac    5040
ttcaccaagg atgtcaaggc cgctgctaat cagatgcgca acttcctggt tcgagcctcc    5100
tgccgccttc gcttggaacc tgggaaagaa tatttgatca tgggtctgga tggggccacc    5160
tatgacctcg agggacaccc ccagtacctg ctggactcga atagctggat cgaggagatg    5220
ccctctgaac gcctgtgccg gagcaccgc cagcgggcag cctgtgccca gctcaacgac     5280
ttcctccagg agtatggcac tcaggggtgc caggtgtgag gctgccctc ccacctccgc     5340 tgggaggaac ctgaacctgg gaaccatgaa gctggaagca ctgctgtgtc cgctttcatg    5400
aacacagcct gggaccaggg catattaaag gcttttggca gcaaagtgtc agtgttggca    5460
```

<210> SEQ ID NO 30
<211> LENGTH: 1963
<212> TYPE: DNA
<213> ORGANISM: Homo sapiens

<400> SEQUENCE: 30

```
gttttccttg ttcctggtca acaaagaaat gtggagtgtc ttggctgaat cctcatacag      60
acaagatcat tatggtgctg ttaggtagga cttgtatcca gatgtaaggt tgaaaaagtg     120
atataataaa ggaaccaagg agaaaattca gaaggaaaga aaaaattgcc tctgcaggtg     180
tgcgagcagg attgcttctg caacaaaagc ctccacccag ccacatcttg ggaaaagaat     240
ggccacttct tggggcacag tcttttttcat gctggtggta tcctgtgttt gcagcgctgt     300
ctcccacagg aaccagcaga cttggtttga gggtatcttc ctgtcttcca tgtgccccat     360
caatgtcagc gccagcacct tgtatggaat tatgtttgat gcagggagca ctggaactcg     420
aattcatgtt tacacctttg tgcagaaaat gccaggacga cttccaattc tagaagggga    480
agtttttgat tctgtgaagc caggactttc tgcttttgta gatcaaccta gcagggtgc     540 tgagaccgtt caagggctct tagaggtggc caaagactca atcccccgaa gtcactggaa    600
aaagacccca gtggtcctaa aggcaacagc aggactacgc ttactgccag aacacaaagc    660
caaggctctg ctctttgagg taaaggagat cttcaggaag tcaccttttcc tggtaccaaa    720 gggcagtgtt agcatcatgg atggatccga cgaaggcata ttagcttggg ttactgtgaa    780
ttttctgaca ggtcagctgc atggccacag acaggagact gtgggacct tggacctagg     840 gggagcctcc acccaaatca cgttcctgcc ccagtttgag aaaactctgg aacaaactcc    900 tagggggctac ctcacttcct ttgagatgtt taacagcact tataagctct atacacatag    960
ttacctggga tttggattga agctgcaag actagcaacc ctgggagccc tggagacaga    1020
agggactgat gggcacactt tccggagtgc ctgtttaccg agatggttgg aagcagagtg    1080
gatctttggg ggtgtgaaat accagtatgg tggcaaccaa gaaggggagg tgggctttga    1140
gccctgctat gccgaagtgc tgagggtggt acgaggaaaa cttcaccagc cagaggaggt    1200
```

-continued

| | |
|---|---|
| ccagagaggt tccttctatg ctttctctta ctattatgac cgagctgttg acacagacat | 1260 |
| gattgattat gaaaaggggg gtattttaaa agttgaagat tttgaaagaa aagccaggga | 1320 |
| agtgtgtgat aacttggaaa acttcacctc aggcagtcct ttcctgtgca tggatctcag | 1380 |
| ctacatcaca gccctgttaa aggatggctt tggctttgca gacagcacag tcttacagct | 1440 |
| cacaaagaaa gtgaacaaca tagagacggg ctgggccttg ggggccacct ttcacctgtt | 1500 |
| gcagtctctg ggcatctccc attgaggcca cgtacttcct tggagacctg catttgccaa | 1560 |
| caccttttta aggggaggag agagcactta gtttctgaac tagtctgggg acatcctgga | 1620 |
| cttgagccta gagatttagg tttaattaat tttacacatc taatgtgaac tgctgcctaa | 1680 |
| ccactcaaga gtacacagct ggcaccagag catcacagag agccctgtga gccaaaaagt | 1740 |
| atagtttttgg aacttaacct tggagtgaga gcccagggac aggtccctgg aaaccaaaga | 1800 |
| aaaatcgcat ttcaacccctt tgagtgcctc attccactga atatttaaat tttcctctta | 1860 |
| aatggtaaac tgacttattg caatcccaag acccatcaat atcagtattt ttttcctccc | 1920 |
| tatacagtgc cctgcccacc cttatctgca cccacctccc ctg | 1963 |

<210> SEQ ID NO 31
<211> LENGTH: 9604
<212> TYPE: DNA
<213> ORGANISM: Homo sapiens

<400> SEQUENCE: 31

| | |
|---|---|
| tgcagggctg tgaccgtcta tgacaagccg gcatctttct ttcaagacac acctctggac | 60 |
| ctgcagcgcc agctcttcat gaagctcagc ggcacacact ctccgttcag ggcccggtag | 120 |
| gcctcccatc ctcagctgcc ttctctcctg ctcgccactg ccctggcctg tccccttctc | 180 |
| actgcagacc tgggaaccca ctcacccagg ggttggcaaa gtaaggctac aggccagtct | 240 |
| cctgcttttg taaatcaagt gtcattggga cacagcacac tcattaactt ctgagttgtc | 300 |
| tacagccgcc tttgagctgc aatagcagaa tcgtgttttg caacagagaa cctgtggccc | 360 |
| gcaaagcctg aagtatttac tctctggccc tttaagaaat gtttgtggac ccctgcgctg | 420 |
| tcttactctc ctgccaatgg gttcccagcc tgtggcagg acctgtggac ctgtgtgtcc | 480 |
| cctgggtgt ctcatggggc taaggagggg accttttgtgc aggtccacgc accctgaggt | 540 |
| gtgcccctgt gtaagctggg gtggtgtggg agggcgtccc tgcaccctca tcttgagtcc | 600 |
| aggggatgat aagacagtaa gtcccgtgga gaaaggaat gagtcagtct tgtttgctgt | 660 |
| tgtaaactta tcacccagca acaatattag agaaagcaag cccaggcctc ggatggcagg | 720 |
| ggtgacctgg tgctgctgat gtggccgggc accccaacct ttgggagcct gcaggccttg | 780 |
| ccacggcagg agatgcccgt cctgggtcct gggcctgctc tgtggcctct cacaagcttt | 840 |
| tttcctgctc tttcagctca gaacctgagg acccagccac ggagcggtcg gccttcatga | 900 |
| agagggatgc tgggagcggg ctggtgatgc gtctccacga gcggccagcc ctgctggtca | 960 |
| gcagcacagg ctgacaggt ctgcacgacc cctgcaacac ttgggggttgg tgtgacaggc | 1020 |
| acctggccaa cctgtgttgt cctcacacct gccagtcctt catgcccccca ccctgccacg | 1080 |
| gtctcaatga aagggggagg tcgtgagagc tgtaagaggg gtgtctagaa acaggaccct | 1140 |
| gacattcaat tctcttctca tagaggacga agacttctcc atcctgctgg cagctttaga | 1200 |
| aagtaggtgt gtggctgcgg tgaggagctc tgggcttgtc gggggccact gagctgtgag | 1260 |
| ctgcttgcct ggcctgcagc atgttcctgt ccctggccac tgggtggggc agcctgggga | 1320 |
| cagtggggat ggtggaggtg ggccgccttg aatcccccagt tgggtcattg agtgaccagg | 1380 |

```
ccctcaggct gaaatgcccc ctccaggaga gtatttcaca gaggctggtg gcctccccac    1440
cagagcagtg ctctttctcc acctgaacag gtgactctgg ctattgttta tttaaaagtt    1500
tttttctgaa tgggcatggt ggctcacacc tgtaatccta gaactctggg aggccgaggc    1560
aggcaggtca cctgagggca ggagttcgag gccaacatgg cgaaacctgt ctctactaaa    1620
aatacaaaaa ttagctgggt atggtggtgg gggcctgtaa tcccagctac ttgggaggct    1680
gatgcacgag aattacttga acccggggagg cagaggttgc agtgaactga catcacgcca    1740
ttgcattcca gcctgggtga cagagccaga gtctgtcgga aaaaaaaaa aaaaaaattc    1800 taccagaaat tccgtgtaga attgtttctt tttttaaaca cagagtttga acaactgact    1860
cttgacggac acaaccttcc ttctctcgtc tgtgtgataa caggtaccgc ctgggcccct    1920
gggtgtctgt gtggttgggg gatggtggat ggggagggggc acgcagcctt taccctgtgc    1980
ttcccacgat cttgtctcct taatcctcac tgcagctctc tgccataggg acttatactg    2040
cttgacatgg gggaaactga ggctcagagg gtttcacagc agggcaggga cccagattt    2100 gaatctgtag ataccaagct ttctactttt tcagtagttt ccaagcatct tttttgttgt    2160
tgttgttaca tcactggtgt cttttttttt ttttttgagac acagtctcta tcgcccaggc    2220
tggggtgcag tggtgtgatc ttggctcact gcaacctcca cctctcacat tcaagcaatt    2280
ctcgtgcctt agcctcccga gtagctggga ctacaggggc ccaccacacc cagctaattt    2340 ttgtatttt agtagagatg gagtttcacc ctgttggcca ggctggtctt gaactcctga    2400
cctcaggtga gccacccaac ttggcctccc aatatgctcg aattacaggc atgaatcact    2460
gtgtctggcc atgtcattgg tgccttaacc aagcgtcttt taatttttta aacggaagag    2520
cccctgtccc acagttactg ctgctgagcc ctttcaaggt gactcagtga ggagggagaa    2580
aagcggaagc ggtgtgggaa gaggcggggt ctgggccagc tgctgctcct gctctcctcc    2640
ctcctctggc ctctaggctc ccaggagtgg tttggaacct gcgccatgtg ctctggaggc    2700
tgtggcaggg caggggcgtc ttggaacctg cgccatgtgc tctgggggct gtgccaggga    2760
agggggagtc ctcgtgtccc ctgcgcacaa cacagacaga aggctggatc cacccagtgg    2820
gcggtcgggt gccaggccag tgcttactcc gccatgtttg cagcccgagg ccagctggct    2880
gcaggtgcag gactatgcct caggggtcag ggtgcacaca cccctgcatg tctcggggct    2940
cctgggtagc ttctggaagg gcccagatgg ggcctgactg gagctgccga ggggtggagc    3000
ttctgggaaa aggatccctc ctaggggggga gtgtcttgag cctggggcca tgtggcaggg    3060
acagagacgg gtccatggca gtgtctcctc ttctctgtga aggcaaaggg cctctgaggg    3120
agtattacag ccgcctcatc caccagtagc atttccagca catccaggtc tgcaccccct    3180
ggctggaggg ccgaggacta cccccgcttc taggtgagag gccagcggga ggctcaggga    3240
ggaggcaggg ccttaagcag ggggaacagg ggtgggcagg atgtactttt tctgaaaagg    3300
tggctctgga ggccacttgg gcacgggacc tgggctctgg ctgaactccc gggaggaggc    3360
tactttctgg tgtgccagcc cctcccagcc aggtggcccc agaggccctt taccaagggg    3420
tttgaggagg tcacatcctt tcagcctgcc acgccctcca ttcagtcctc ttccttcctg    3480
caggagggct gggcctgggg ttgggggccac tgttgcccag gtgtaggaag gcagtggctt    3540
tgggaggtac agggacgatg tgtcaaacag cgtcgcctct cccagtgaga tggttctgct    3600
ttgcctccgt ctctttcccc gttgtttttct ccaagtgggg agttgtgtct tggtcctgat    3660
gcgtctctag agccgcatct tccagcttct agtgagcaga gcagttggag gctgaggcct    3720
```

```
tttcctggca ggactctcca gctagtcttt gttttagaca gtctcgctct gttgcctagg    3780
ctggagtgca cgatctcagc tcatgcaacc tccgcctcct gggttcaagc gattctccca    3840
cctcagcctc ccgagtagat tatgggatta caggagccct ccacaacacc tggcttattt    3900
ttgtattttt agtagaaaca gggattcacc atgttggcca gactggtctt gaactcctga    3960
cctcaagtga tcctcctgtc ttggcctccc aagtgctgg gattccaggc gtgacccatc    4020
acgcctggtc ccagctagtc tttagaaatg ttaagccgtt tcgctttatt ttcacactga    4080
cagctggttt gtagtgggtg tgctgtggtt tattattatt attattatta ttattattat    4140
tattattatt ttgagaagga gtttcgctct tgtagcccag gctgcagtgt aatggcacga    4200
tcttggctca ctgcaacctc tgccttccca ggttcaagca attctcctgc ctcagcctcc    4260
tgagtagctg ggattacagg cacctgccac gacacttcgc taattttgtg tttcttttag    4320
tagagatggg gtttcaccac gttggccagg ctggtcttga actcctgacc tcaggtgatc    4380
cgcccacctt ggcctcccaa aatgctggga ttacatgcgg gaggtgaacc tgggaggtgg    4440
aggttgcagt gagctgagat tgtgccactg cactccagcc tgggtgacag agtgagactc    4500
tgtctcaaaa caaaacaaca acaacaaaaa aaccaaattg tgattacgta gaaaaagtgt    4560
caacttacat tttcagatgt cccagccaga ccatgtggct gcttggccag cttaagccac    4620
ttgtgcttgg ggctgcgggg ggccttatct gattttcact cccctcgggg gatgctgcct    4680
cactgtgctg ggaggatttg tgttcccagg gcagagacca gctctctgac cgcacccctc    4740
ttgcctagca gggtcggtgg acctgggtgt ctgtctagac acgtcctcca gtggcctgga    4800
cctgcccatg aaggtggtgg acatgttcag gagctgtttg cctgtgtgtg cgttgtgaac    4860
ttcaagtggt aggagcagaa cccgaatctt tctggggata gcttcacaga tccaccgctg    4920
agggggaaac agtgcagagc cagctgccca cagtgaggcc ctgccccttg gtcagtccag    4980
cacacactgg aggccatgag gaggagccct gtggttactg tggctgggct gagcctcact    5040
gaagtagttg cttccattta gaactcatgt tatatttagg ttggtacaaa agtaatcacg    5100
gttttttgcca ttaaaaatgg caataacttt tgcaccaacc taatatgaaa aagaaagca    5160
ccttaaaatac tagaactcca ctcggggctt ttgctcctag agtagaattg gcgggaattg    5220
cctgcaggct tacatggttt tctttgtttt tctctcccac catgtccctt ttggccaagc    5280
tcacatggtg ggtttgaatg agttaaatga gtgtcatgct gtggcctcac tgcacccagc    5340
atagatgggt gtttggaagg gtggcgttag aggagattct agaagcagta gccccagcac    5400
aagttgagcc cttggcccct gctcaggagc cggctcctgg atgggattca gggattcaag    5460
cccctcgtgt gagctgagct cagggaacgt cttgatcaaa tctggtgccc tagaaaagtc    5520
atcttttatg tgctgaacca gtctccaggg ggttgcctta cttgttccac agccatggaa    5580
ttaagaaaaa catacaaaaa taattcttca gtccttgaag agcatccagc acagaaggta    5640
caaaccctcc ttaaggctcc ctcctcaaat cggtttggcc attttgatgt gcactccccc    5700
aggcctttat acccttcaga tgccaaatct aagaaccagc tcccagaaac cacaccccct    5760
gttccaatcc ccagcctggc ttgagcgtgg ggtgcgaggg gagcccaggt gggcacccca    5820
ggggtctggt gtcttctcca ggcagctctc aggctccctt ggttctctct gcagtttaca    5880
tgagctggtg aaacatcaag aaaacggctt ggtctttgag gactcagagg aactggcagc    5940
tcagctgcag gtagccacat ctgccactaa gccagggtgg gcagggttct ggagactggc    6000
accgagccac gctccctgat ccctgcttcc cacagtcggg gtgggaccat gtgggtctg    6060
gcggaaaagc tagggaggga gcagaggtca cagaggctgg cctactctgc tgtcccgttt    6120
```

```
cggtacagta ggctcgggaa agttaggaca caaccccacc tgcccgcctg cccgctggat    6180
ttatggaaca gacactccac aaatgacgct ggagccgggt gggccgggct gcagtttagg    6240
aagtgagcag gatcaggtag gtgagtgggc aaagggagct tctgggacca gccttgaaag    6300
atgggtggaa ttctgcaaat gttacttgtt tcttattgca aaaagtaata catcgttctt    6360
gccaacagaa tgactggcag gattttcagt aaaggtccaa gtcggaagtc atttagactg    6420
ggtcccctag tctctgtcag aaccatggta ctctgttggg gtgtgaaagt agccacagat    6480
catctgtaga ttaaggggtg tggctttgtt ccaataaatc tttatttaca aacacaggct    6540
gtgggctgga tttggcctgc aggctgtagt ttgtgatcct tgattcagac agtttagcaa    6600
ggctgaaaag aacaccgaca ccccttgtt acccacagat gggtgggact tggccagagg    6660
ccaagaggag ggtgctcgca ggggagcata cagcatgaag aggccgggag gtgccccagg    6720
acaccaagtg tgggaaagtg ggacatgcgg ggaagttccc agaaagcgtg atgtcaagtt    6780
ggaggcggag cgctgctggg gcgtgaagag tctcgagtcc aagtgaggga gttaagaact    6840
tggtaggggt tgttgttggg tcgggcacct ggggtcagcc aggtggtgac ctgggatgcg    6900
gtggggacag gcaatgaggt aagctctgct ctttagtatt atgcagatgc ttttctcaaa    6960 cttttcctgat cctgcaggca agctaaacct gttccggaag aacctgcggg agtcgcagca    7020
gctccgatgg gatgagagct gggtgcagac tgtgctccct ttggttatgg acacataact    7080
cctgggccag aggctaaaac cccagggccc ctgctgtcct tcccgcagct tcttcttgga    7140
gtctcagggc aaacccttc aagcagcgcc tcccagtggc cagaagctga atgacggca    7200 gtggtgccgc ctggtgagtg aattgcttct gtgacccggg aagctgtggt tggctctgat    7260 ttctttttttg gaggcttgga aacacttcct ctcttcttct gttcttcacg ccccatgccc    7320
ctgctagcgt actactgttc tgtgacttcc ctgtgacctc tgcagtactc ctcatcctgc    7380
gtttggtctc caggtgtcgc cttctgccg tgttcctaat attttgatc ctgtcttgaa    7440 aaaagcacct gctgcacagt aagcccaggg atgtggcagc tgcagcgggc ttggctttgt    7500
gaggaaccgg gtgtgtccac gttgggggaa catcatactt gatacacacg ttttatttg    7560 cacaaagaaa atgctatttt tagagccaga attttcatgt ctgatttatg gtgattttct    7620
taagaaccag aactgctggc agaaagggg cacccacacg cttagatagc cgatgtctta    7680
ttagagggca gtttgtggtt cctgatttgg aaattaatat tctccaaaca ttccagtcca    7740
atgaaagttt tatccgcttt cccatgtaaa aattcttccc atgagagtga cttgatcctc    7800
acaatcccgt tgaagtcgcg tgtgagtcct acagtattag gttcagcatt gccatctcca    7860
agtgctcttt gtagggaaac agtttctggt catgacaagc ttccacttcc catctgatcc    7920
tggcctggcc tggaaacaga gcacatgtgt ttgaggatgg cggtgtttgg ggacaggaca    7980
tgagcgtatt gtgtggggct gctaggacag gcgtggtgtg gtggggagt gtccaagtca    8040 gtctacttgt ttcacagttt cccagtccca cccaggtacc tagaattggc ctccaggatg    8100
ggaccagaaa tctggttttg catagaaatg gttagcagca ggcaccgtgc cgctgtccac    8160
tctctgctgg cgtctgcccc agcacttggc acagcgggac agaagcagag ctctgaaccc    8220
acatctacct ggctgcccag tcaacccact cttcacaaag cttagaaagc ggccgggcac    8280
agtggctcac gcctgtaatc ccaacacttt gggaggccaa ggtgggggga tcacttgagg    8340
tcaggagttc gagagcagcc tggccaacat ggtgaaaccc catctctaca aaaatacaaa    8400
aattagccag gcatgatggc gggtgcctgt aatcccagct acctgggagg ctgaggcagg    8460
```

| | |
|---|---:|
| agaattgctt gaacccagga ggcagaggtt gcagtgagct gagattgtgc cactgcactc | 8520 |
| cagcctgagt gacagagtga gactccattt caaaaaaaaa acaccaaaaa aaacaaaaca | 8580 |
| aaacaaacaa acaaaaacac acacacacag cttagaaggg gctggtgttc tcataagcac | 8640 |
| agatgtctga agagccgtta gccagaatga ttctttttttt ttttttttttt ttgagatacg | 8700 |
| atcttgttct ttcacccagg ctggagtgca gtggcacagt cattgctcac cacagccttg | 8760 |
| actcctgggc tctagcaatc ctcccatttc ctgactagct gggatgacag gtgcgtgcca | 8820 |
| ccatgccagt aattttttta ttttgtagag atggggtcct gaacccatgg cctcaaatga | 8880 |
| tgctcctgcc tcagcctctt ttattatttt tttttggac ggagtttaac tctgttcccc | 8940 |
| tagctggagt gcagtggcgc aatctcagct cactgcgatg cctcccaggt tcaagtgatc | 9000 |
| ctcctgcatc agcatcccga gtagctggga ttataggcgt gcagcaccac gcctggctaa | 9060 |
| tttttgtgtt tttagtagag atggggtttc accgtgttgg ccaggctggt cttgatctct | 9120 |
| tgacctcaag tgatccgctc acctcagcct cccaaatcct cagcctctta cagtgttggg | 9180 |
| attacaggtg tgagacactg tgacccggga tgattttcaa tcacagttttt ttgttacaag | 9240 |
| tggaaaatgc atatctataa aaatgaagta gtgcagacat gaatgtgtag aagtctctat | 9300 |
| aatcctgcca tccaaggatg gcacctgtta acgagtgtat tagggatgtc caatcttttg | 9360 |
| gcctccctgt gccacattgg aagaagaatc accttgggcc acacataaaa tacactaacg | 9420 |
| ctagcaatag ctgatgagct aaaagaaaaa aattcacaaa aaaacctcgt actgttttaa | 9480 |
| gaaagtttac agatttgtgt tgggccgcag gttggacaag cctgctatat atatattcta | 9540 |
| ggttttctcc tataggtata cttatgtgaa aatgatgatt gtgataattt ttttttttgag | 9600 |
| atga | 9604 |

<210> SEQ ID NO 32
<211> LENGTH: 1164
<212> TYPE: DNA
<213> ORGANISM: Homo sapiens

<400> SEQUENCE: 32

| | |
|---|---:|
| ggtcagctgc acctagaagg ggcccccctcc tggctcaaaa atggctgcaa ccacatgagc | 60 |
| catgtgactc aggatggagg gtggcactgt ccacaaatcg gcttctctgc agagcccact | 120 |
| ctgcaaggct gcggtgaggg gctgaggctg gctgcctggt gggatggcct gagatcctgc | 180 |
| tcctgctagg gccagaggcc aactgcctct agggttgctt ggtgcctcag taacaggtgg | 240 |
| tttgagtgga tgtctcctgc aggaaccatg actagaaatg tggttagaca agaatttgag | 300 |
| gctccaggga agccacagga ttctagccag caggatgcct gcttaatcct cgtaaaagga | 360 |
| aactggacaa caaacgagat ggaggtaaaa tgaaatccca aggaacgcc tcaaggatc | 420 |
| ccgtcttcta cctgtcagga gatgttctat ttttctaact tccccacctt cagcataaca | 480 |
| ggatttagta actgtttaga ccttttgaag aacaaagaca aaaataggaa gttgtgtcag | 540 |
| aggagtgcag tcatctctta ttcatggtag tgttttggtt cgattttgga gcatccacca | 600 |
| ggttcgcgta caggagaaga aacacggatg atctctgtct ttattttggg ggaggacaat | 660 |
| ccggccttct tgggactgtt ccagcccacc tcccagatgc ttcggtcagt ctgatccacg | 720 |
| agatatctca ggctgggaag aacacatctt gggccaactt ccacagcagc catgcgtcca | 780 |
| aggatacaga atcaggcagg ccgataaaag gattttgact tgggtttcac aggaaggagg | 840 |
| tatgccatca aaccccactg tagtcaagga tcagaaggtg cttttagcag gaactgaagc | 900 |
| ttttttagtat aaggcccact tagggtgcca gcaccctgac agtgtcccctt taatccactt | 960 |

```
cagatctggt tgactcatca tcaggtgttt ccattcactt tcaaaattac acagtcacag    1020
gataacagtg agatccactg ctaaagggta aagggtcaga ggctgaagag tactgtgtaa    1080
tgtctgcatg agatttgttt taaaaaagtc tgaattggca tggtattttg aatgctgctg    1140
gaactgtaat aaaggttcac cttt                                          1164

<210> SEQ ID NO 33
<211> LENGTH: 2947
<212> TYPE: DNA
<213> ORGANISM: Homo sapiens

<400> SEQUENCE: 33
acattcttcc cgggcactcc tgagtttgag ccgggcctgg aggacctggg ccaagacttt      60
cgagcggcgg ccgcccgagg tgcgaggagc cagcccggct ttcctcactg ggtcccgcgc     120
aggcgtcccc gggaccgcag agcaaacttt ctggactatc tgaggacact tgtccagcga     180
gccccactgc tcggggagga ggagccacgg ccggggacag tgatacactg gggtgttga      240 aggacatttt tgaaatcatg agaactcaat gtttgactat gaatgtttcg ttataactgc     300
ctggaaggtt agcgtcaaag aagttgagat ttttaaagtc ttcttctagg ggtttccagc     360
agagccaaat gttagaaaaa tctttccgct cctctgaaga gtgaagtgag caaatacaac     420
ccagcagtag ttattgaag acagcagccc caggttttgg aaggtgacaa tgaaatgtga      480
agaagttaca tttctcaaac ttgaaagtta gtgacggctt accaaatttt aatgaaaatt     540
aaatatgact tagaagcatt gatttatgaa ggcttatgat gtcatcggtt tcgacagaaa     600
gcaaactcca gcaggctgtg agcctacagg gagttgaccc agaaacatgc atgattgtat     660
ttaaaaacca ctgggcacag gttgtgaaaa tcttggagaa gcacgacccc ttgaagaaca     720
cccaggcaaa atatgggtct atccctccag atgaggccag tgccgtgcag aattacgtag     780
aacacatgct cttcttgttg attgaagagc aagccaaaga tgctgcaatg gggccgattc     840
tggaatttgt ggtctctgag aacatcatgg agaaactttt cctttggagc ttgagaaggg     900
agtttactga tgagactaaa attgagcagc taaagatgta tgagatgttg gtcacccagt     960
cgcaccagcc tctgctgcac cacaaaccca ttctgaagcc tctgatgatg ttgctgagct    1020
cttgttcagg aacaaccacc cccactgtgg aggagaagct ggttgtccta ctcaatcagc    1080
tctgttccat tcttgccaaa gatccatcca ttttagaact cttcttccac actagtgaag    1140
accaaggcgc tgccaacttc ctcatcttct cccttctgat tccccttcat taccgagagg    1200
ggtcagtagg ccagcaagct cgggatgcat tgctcttcat catgtctctt tctgctgaga    1260
acaccatggt ggcccatcac atcgtggaga cacctacttt tgtccagta cttgcaactg      1320 ggctcagtgg tctctactct tccctgccta caaagctaga agatgaggag gatgactttg    1380
actcttttat agcggagatg cctgctgtag agactgtgcc ttccccattt gtggggagag    1440
atgaggctgc ctttgccagt cgccatcccg tgaggactca aagcacccca ttcacaggcc    1500
cattcatcag cgtagtcctg tcaaagctgg agaacatgct ggagaactct ttacatgtta    1560
atttgctgct tatcgggatc attactcagc tagccagcta cccccagcca ctcctgcgct    1620
cctttctgct caacaccaac atggtcttcc agccaagcgt ccgctctctc tatcaggtcc    1680
ttgcatctgt gaaaaacaag attgaacagt tgcttctgt ggagagagac ttcccagggc     1740
tcctcattca agctcagcag tacctgctct ccgtgtggga catgtctgat atgacccctg    1800
cagcactaac caaagatccc attcaggagg cttccaggac aggaagtggc aagaaccttt    1860
```

| | |
|---|---|
| tggatggacc tccaagagtg cttcagccct tcctgaccca cagaaccaag gtggctgagg | 1920 |
| cacccccaa cctgccctg ccggtgagga acccatgct ggctgctgcc ctcttcccag | 1980 |
| agttcctgaa ggagctggcg gccttggccc aggaacactc cattctgtgc tacaagatct | 2040 |
| tgggtgactt tgaggactcc tgctgttagc ttttttttt tttttaata gaggttcttg | 2100 |
| ttttgtaagg ttttagtgtc ttgactgaat gttaaatgca aagctgctta caaagatttc | 2160 |
| tactttaatg tttcctgaca atacttgatt tgtggggagg ggaattttct gtatctttcc | 2220 |
| tctctctctc tagccgggcc tttccacctt atgttatata tagaatgtaa gtctcataag | 2280 |
| ctggttgctc ccttggcagt tttctttgct ctgttttcc tccttatatt tttttggttg | 2340 |
| tcattctcct atccctttga gttactcttc ttgcagctca gatcacgtca agcagatatt | 2400 |
| ggggttcagt gatgtctggt gatgtctgga agtgccccat gtcagaattc cagctgttca | 2460 |
| gcagcacagg aagattgtac acctgcaact gtgcgaatgg tcctgttgcc tcctgcattt | 2520 |
| tggcctctgt tctataaagg aagagtaaag atggagctcc tcctgcctcc atcacgaaag | 2580 |
| cacatatcat ctgtcccttt ggattttact tccaggacgt gtgtcgtccc cagcgtgtgt | 2640 |
| tgccttatgg tgccggcaga gcctcagcta tctgcctggg aagtcggatg tccttggaga | 2700 |
| gaatttggaa tgcagataat ttttcttatt tcttgagagc ttactttaat cagcatgaca | 2760 |
| ctacctaaac actgaagatg gccttatatt agtaagattt gcacaaaatt aagtatacct | 2820 |
| atgcaaacta ttactttggt ttttaggagt ttgatcagat gaagaagtaa tggtatcaca | 2880 |
| tatatatgta agaagacaac catcattatt tttgtaagtg ttttataaaa acaaactgat | 2940 |
| taacttg | 2947 |

<210> SEQ ID NO 34
<211> LENGTH: 4576
<212> TYPE: DNA
<213> ORGANISM: Homo sapiens

<400> SEQUENCE: 34

| | |
|---|---|
| acattcttcc cgggcactcc tgagtttgag ccgggcctgg aggacctggg ccaagacttt | 60 |
| cgagcggcgg ccgcccgagg tgcgaggagc cagcccggct ttcctcactg ggtcccgcgc | 120 |
| aggcgtcccc gggaccgcag agcaaacttt ctggactatc tgaggacact tgtccagcga | 180 |
| gccccactgc tcggggagga ggagccacgg ccggggacag gtgatacact tgggtgttga | 240 |
| aggacatttt tgaaatcatg agaactcaat gtttgactat gaatgtttcg ttataactgc | 300 |
| ctggaaggtt agcgtcaaag aagttgagat ttttaaagtc ttcttctagg ggtttccagc | 360 |
| agagccaaat gttagaaaaa tctttccgct cctctgaaga gtgaagtgag caaatacaac | 420 |
| ccagcagtag gttattgaag acagcagccc caggttttgg aaggtgacaa tgaaatgtga | 480 |
| agaagttaca tttctcaaac ttgaaagtta gtgacggctt accaaatttt aatgaaaatt | 540 |
| aaatatgact tagaagcatt gatttatgaa ggcttatgat gtcatcggtt tcgacagaaa | 600 |
| gcaaactcca gcaggctgtg agcctacagg gagttgaccc agaaacatgc atgattgtat | 660 |
| ttaaaaacca ctgggcacag gttgtgaaaa tcttggagaa gcacgacccc ttgaagaaca | 720 |
| cccaggcaaa atatgggtct atccctccag atgaggccag tgccgtgcag aattacgtag | 780 |
| aacacatgct cttcttgttg attgaagagc aagccaaaga tgctgcaatg gggccgattc | 840 |
| tggaatttgt ggtctctgag aacatcatgg agaaacttt cctttggagc ttgagaaggg | 900 |
| agtttactga tgagactaaa attgagcagc taaagatgta tgagatgttg gtcacccagt | 960 |
| cgcaccagcc tctgctgcac cacaaaccca ttctgaagcc tctgatgatg ttgctgagct | 1020 |

```
cttgttcagg aacaaccacc cccactgtgg aggagaagct ggttgtccta ctcaatcagc   1080
tctgttccat tcttgccaaa gatccatcca ttttagaact cttcttccac actagtgaag   1140
accaaggcgc tgccaacttc ctcatcttct cccttctgat tcccttcatt caccgagagg   1200
ggtcagtagg ccagcaagct cgggatgcat tgctcttcat catgtctctt tctgctgaga   1260
acaccatggt ggcccatcac atcgtggaga cacctactt tgtccagta cttgcaactg    1320 ggctcagtgg tctctactct tccctgccta caaagctaga agagaaaggc gaggaatggc   1380
actgccttct gaaagatgac tggcttctac ttccttctct tgtccagttc atgaactccc   1440
tggagttttg caatgcagtc atacaggtgg ctcaccccctt gattcgaaat cagcttgtca  1500
attacattta caatggattt ttggtaccag tcttggctcc tgctctccat aaggtgactg   1560
tggaagaggt catgaccaca actgcatatc tggacctttt cctgcgtagc atctccgagc   1620
cagcactact tgagatcttc ctccgtttta tcctattgca ccagcacgag aatgtccaca   1680
tcctagacac tctcacgagt cgaatcaaca cccgtttcg gctttgtgtg tgtctctgg    1740 cattattcag aactctcatt ggtttacatt gtgaagatgt gatgttacag ctagttctaa   1800
ggtatctgat cccctgcaat cacatgatgc tgagtcagag gtgggctgtg aaggagagag   1860
actgttactc tgtttctgcg gccaagcttc tcgccttgac tcctgtctgc tgctccagcg   1920
ggatcactct gacgctgggg aaccaagaga gggattatat tctctggtca agtgtatgc    1980 atgacacttc agggcctgtg gagcggccat tccccgaagc gttctccgag tcagcctgca   2040
ttgtggagta tgggaaagcc ctggacatca gctacctgca gtacctgtgg gaggcccaca   2100
ccaacatcct ccgctgcatg agggactgcc gtgtctggtc cgccctgtat gatggcgact   2160 ccccccgaccc tgagatgttt ctccagagtc tgacggagga gggcagtgtg agctcggcct  2220
gccctgtgtt cgggctcccg caacaactcc ccaggaagac aggacctcag ctggctccca   2280
gaaaggacaa gagccagaca gagctggaat gggatgacag ctatgacact ggaatctcct   2340 cagggggctga cgtgggctcc ccagggcctt atgatgatct ggaggtttca ggcccccccag 2400 cacccattga tccccccaaa cacatccagg agatgaagaa gaatgccctc ctgctcttca   2460
aagggtccta catagaagag tcggactttc aggatgatgt gatggtgtac aggctgtgtg   2520
ctgagaagga ctccgaggac atgaaggatt ctcaggagga agctgctagg ccaccagctg   2580
aagcccaggc tgaagttcag agtgtcccca tcaacaacgg ccccctcctc agcacccagc   2640
cagagacaga ttcagaggag gagtggaata gggacaattc agacccgtttt cacagtgagc   2700 ccaaggagcc aaagcaagag agggaacctg aagcagcccc agaatccaac tcagagttag   2760
catcccctgc ccctgaggca gagcacagct ctaacctgac agccgcccac ccggagagcg   2820
aggagctcat tgcccagtat gaccaaatca ttaaagagct ggattccggc gccgagggct   2880
tgatggaaca gaattacccc acacctgatc ccttgcttct cactaaggag gaagaaggga   2940
aggaagagag taaggagaa aaggagaagg aggggaagaa ggagctagaa gatgaggagg   3000
atgactttga ctcttttata gcggagatgc ctgctgtaga gactgtgcct tccccatttg   3060
tggggagaga tgaggctgcc tttgccagtc gccatcccgt gaggactcaa agcacccat   3120 tcacaggccc attcatcagc gtagtcctgt caaagctgga acatgctg agaactctt    3180 tacatgttaa tttgctgctt atcgggatca ttactcagct agccagctac ccccagccac   3240
tcctgcgctc ctttctgctc aacaccaaca tggtcttcca gccaagcgtc cgctctctct   3300
atcaggtcct tgcatctgtg aaaaacaaga ttgaacagtt tgcttctgtg gagagagact   3360
```

| | |
|---|---|
| tcccagggct cctcattcaa gctcagcagt acctgctctt ccgtgtggac atgtctgata | 3420 |
| tgacccctgc agcactaacc aaagatccca ttcaggaggc ttccaggaca ggaagtggca | 3480 |
| agaacctttt ggatggacct ccaagagtgc ttcagccctt cctgacccac agaaccaagg | 3540 |
| tggctgaggc acccccaac ctgccctgc cggtgaggaa cccatgctg gctgctgccc | 3600 |
| tcttcccaga gttcctgaag gagctggcgg ccttggccca ggaacactcc attctgtgct | 3660 |
| acaagatctt gggtgacttt gaggactcct gctgttagct ttttttttt tttttaatag | 3720 |
| aggttcttgt tttgtaaggt tttagtgtct tgactgaatg ttaaatgcaa agctgcttac | 3780 |
| aaagatttct actttaatgt ttcctgacaa tacttgattt gtggggaggg gaattttctg | 3840 |
| tatctttcct ctctctctct agccgggcct ttccacctta tgttatatat agaatgtaag | 3900 |
| tctcataagc tggttgctcc cttggcagtt ttctttgctc tgttttttcct ccttatattt | 3960 |
| ttttggttgt cattctccta tccctttgag ttactcttct tgcagctcag atcacgtcaa | 4020 |
| gcagatattg gggttcagtg atgtctggtg atgtctggaa gtgccccatg tcagaattcc | 4080 |
| agctgttcag cagcacagga agattgtaca cctgcaactg tgcgaatggt cctgttgcct | 4140 |
| cctgcatttt ggcctctgtt ctataaagga agagtaaaga tggagctcct cctgcctcca | 4200 |
| tcacgaaagc acatatcatc tgtcccttg gattttactt ccaggacgtg tgtcgtcccc | 4260 |
| agcgtgtgtt gccttatggt gccggcagag cctcagctat ctgcctggga agtcggatgt | 4320 |
| ccttggagag aatttggaat gcagataatt tttcttattt cttgagagct tactttaatc | 4380 |
| agcatgacac tacctaaaca ctgaagatgg ccttatatta gtaagatttg cacaaaatta | 4440 |
| agtataccta tgcaaactat tactttggtt tttaggagtt tgatcagatg aagaagtaat | 4500 |
| ggtatcacat atatatgtaa gaagacaacc atcattattt ttgtaagtgt tttataaaaa | 4560 |
| caaactgatt aacttg | 4576 |

<210> SEQ ID NO 35
<211> LENGTH: 6218
<212> TYPE: DNA
<213> ORGANISM: Homo sapiens

<400> SEQUENCE: 35

| | |
|---|---|
| agctccgctc gcgctctcgc cgctcctgcc ggctcgcccg gccccgcgct ccgccgtctc | 60 |
| ctcgccgccc gcccctccgc cagccccggg gaccgcgcgg ccgcagcctg agccagggcc | 120 |
| ccctccctcg tcaggaccgg ggcagcaagc aggccggggg caggtccggg cacccaccat | 180 |
| gcgaggcgag ctctggctcc tggtgctggt gctcagggag gctgcccggg cgctgagccc | 240 |
| ccagcccgga gcaggtcacg atgagggccc aggctctgga tgggctgcca aagggaccgt | 300 |
| gcggggctgg aaccggagag cccgagagag ccctgggcat gtgtcagagc cggacaggac | 360 |
| ccagctgagc caggacctgg gtggggcac cctggccatg gacacgctgc cagataacag | 420 |
| gaccagggtg gtggaggaca accacagcta ttatgtgtcc cgtctctatg gcccccagcga | 480 |
| gccccacagc cgggaactgt gggtagatgt ggccgaggcc aaccggagcc aagtgaagat | 540 |
| ccacacaata ctctccaaca cccaccggca ggcttcgaga gtggtcttgt cctttgattt | 600 |
| cccctttcta cgggcatcctc tgcggcagat caccatagca actggaggct tcatcttcat | 660 |
| ggggggacgtg atccatcgga tgctcacagc tactcagtat gtggcgcccc tgatggccaa | 720 |
| cttcaaccct ggctactccg acaactccac agttgtttac tttgacaatg ggacagtctt | 780 |
| tgtggttcag tgggaccacg tttatctcca aggctgggaa gacaagggca gtttcacctt | 840 |
| ccaggcagct ctgcaccatg acggccgcat tgtctttgcc tataaagaga tccctatgtc | 900 |

-continued

```
tgtcccggaa atcagctcct cccagcatcc tgtcaaaacc ggcctatcgg atgccttcat        960
gattctcaat ccatcccegg atgtgccaga atctcggcga aggagcatct ttgaatatca       1020
ccgcatagag ctggacccca gcaaggtcac cagcatgtcg gccgtggagt tcaccccatt       1080
gccgacctgc ctgcagcata ggagctgtga cgcctgcatg tcctcagacc tgaccttcaa       1140
ctgcagctgg tgccatgtcc tccagagatg ctccagtggc tttgaccgct atcgccagga       1200
gtggatggac tatggctgtg cacaggaggc agagggcagg atgtgcgagg acttccagga       1260
tgaggaccac gactcagcct cccctgacac ttccttcagc ccctatgatg agacctcac        1320 cactacctcc tcctccctct tcatcgacag cctcaccaca gaagatgaca ccaagttgaa       1380
tccctatgca ggaggagacg gccttcagaa caacctgtcc cccaagacaa agggcactcc       1440
tgtgcacctg gcaccatcg tgggcatcgt gctggcagtc ctcctcgtgg cggccatcat        1500
cctggctgga atttacatca atggccaccc cacatccaat gctgcgctct tcttcatcga       1560
gcgtagacct caccactggc cagccatgaa gtttcgcagc caccctgacc attccaccta       1620
tgcggaggtg gagccctcgg gccatgagaa ggagggcttc atggaggctg agcagtgctg       1680
agaacaccaa gtctcccctt tgaagacttt gaggccacag aaaagacagt taaagcaaag       1740
aagagaagtg acttttcctg gcctctccca gcatgccctg ggctgagatg agatggtggt       1800
ttatggctcc agagctgctg ctcgcttcgt cagcacaccc cgaatattga agaggggcc        1860 aaaaaacaac cacatggatt ttttatagga acaacaacct aatctcatcc tgttttgatg       1920
caagggttct cttctgtgtc ttgtaaccat gaaacagcag aagaactaac ataactaact       1980 ccattttgt ttaaggggcc tttacctatt cctgcaccta ggctaggata actttagagc        2040
actgacataa aacgcaaaaa caggaatcat gccgtttgca aaactaactc tgggattaaa       2100
ggggaagcat gtaaacagct aactgttttt gttaaagatt tataggaatg aggaggtttg       2160
gctattgtca catgacagac tgttagccaa ggacaaagaa gttctgcaaa cctcccctgg       2220
acccttgctg gtgtccagat gtctgcggtt gtcagcccct tcctttcccc cgacctaaac       2280 ataaagaca aggcaaagcc cgcataattt taagacggtt cttaggaca ttagtccacc         2340 atcttcttgg tttgctggct ctccgaaata aagtcccttt ccttgctcca actccttgtc       2400
tctcaacgta ttggctatga cgcagcaagc agaatgaatt tggactcagt tacaggctgt      2460
caatggtctg ctctgtagca gtctcagagc ctccccgacc cactacctgg agatagccag       2520
atagccagat gccctgctcc tggccacctt taaagcccct gcatatgaca caggttaact       2580
aaagtcaaga ttggggctgc tgcattccag gttccctaga ctcacaagct ggtccttggc       2640
caggtgcagt ggctcacgcc tgtaatccca gcactttggg aggctgaggc aggcggatca       2700
cctgaagtca gaagtttgag accagcctgg ccaacataat taaaatgtct ctactaaaaa       2760
tacaaaaaat tagctgggtg tggtgacgct tgcctgtatc ccagctactc aggaagctga       2820
gacacgagaa tcacttgaac ctgggaggca gaggttgcag tgagctcaga tagtgccact       2880
gcactccagc ctgggtgaca gagcgagact ccgtctcaaa aaaaaaaaa gaaagcagat        2940 cctcatggct atagagttgg cattttagcc ccagcttctg tagctctgaa agcctaaaga       3000
aggtattctc tccatctgtt aaacacagta tagtggctct cagcccttgg ggcatgttat       3060
catgggaggg aagtcaaata agaggagaga aaagaactca aggggaaac tgcatttta         3120 ggctttgctc tcttaccttg ccctttctac tcagaaccaa taacttctgc atcaaaacat       3180
gttacagcct gcatcaaggg ctttacccca acctgcagcc cagccttccc tgggtgagct       3240
```

```
tgctatgcgc agccacattt accatgtggg gctccctatt ctgatggcct gttcggtgcc    3300
gggtttactc actgccctgt tctgatgtca gtgcctgtac atacctccaa aggcaggact    3360
tgcctgataa atattttcc tcctctgaac tggattttat aggcattaaa gacaagtcgg     3420
gtggctagag ggctccttga gacatacctta gcagggaact gcaggtggat tctgttgaga   3480
ggcaaagcac ctgagtggtt gggacacagg cagctggcat gggagggact tttttttgaga  3540 cagggtctca ctgtgtcgcc cagggcaagg atgcccaaag acaccaggtt ggagaggcac    3600
ctgccaacta cttgctttcc ctggagcctg catgtgcctg tggggtgggg aggcgtaggg    3660
gtctacggct gcctgagatg ggtgtgcaca gtgtgtgaag tacctacctc cttgccttgc    3720
tggactgtca gccagtcgca gggccggcca caagacccat gtctccatct ggtcatactc    3780
catagctacc aagttaacct gctctaaact ttggagaact ggatctgtcc aataaacgct    3840
tatttggcca agcctgatgg ctcgtgcctg tactcccagc actttgggag gctgaggtgg    3900
gagggttgct tgagcccagg ggtttgagac cagcttgggc aacaacaaca aaaatgccag    3960
gtgtggtggg gtgcacctgt agtcccagct actaggaggg ctgagccagg aggatcactt    4020
gagcccggga ggttgaggct gcagtggggg gtcataatca tgccactgta ctccagcctg    4080
ggtgacagag tgagaccctg tctccgaaaa aaaaaaaaaa aaaagaacg gaaaagaaa     4140 tgcttacatt gtcagggatc ctgtagacaa tcattaactc tatgagatgc ttggttctat    4200
ttttttggga gactttgtcc aagtgttttg gcttaagaaa tccataggcc tctcttggtg    4260
acacatctct agtactttt gtcataaaca aacaggccat ctgccgccaa atacatccac     4320
tccccatgcc actgacatcc tatgggtcag ccaggcttgc tttgactgag gccgaggcat    4380
ctggaacttt ctctgcctgc aggggctagc agcagaggct tcaccgcatc accacccctt    4440
cctccactcc tgacattctt tcccttcagg gatccaaaat ggttggccga gctcccagtg    4500
ggaaaacgtg tgctagagtt ggggagtgag atgagtggtg ctgtccatgg aatcaggcca    4560
cagcaggaac tgccccactg gccatttgag acacacacag gtggtaaatg ctctgctggt    4620
gggctgtgct tccctcattc agagagctct gttacagccc actgtgtcct ttagaagctt    4680
gaaaggaacc caactctttg ctgcactgtc cttttcttc ctcaaattca gaccctcctt     4740
ccaccggcac cccctactc caccctcagc tcttccttgc ctggtttatc aagcagagct    4800
gaggccccac gtttccaact ctgattgtca cttgcatctt cacaaaggat aaaccacgga    4860
gcaactggaa aaccatcagc caagcgttcg gatgagtctg gttattggtc cacccccgac    4920
cagattccct tacacttaac tcacttcttt ctttggcaat gaccctcatg acatgtataa    4980
atgggtatga ctaagaagag gctgtgatct aacatttatt tgctgccatt ttttactctg    5040
gggagaagca gccccaactc atcactggga aagaactccc cctgcaaacc agctaaattt    5100
gataatttaa accccctgcc cctaaaactt ctcacagagc tggggagttg gtggcaactt    5160
tccaagtcaa ggtcttgctt agaaagtcct tcactacatg gccaggtgca gtggctcacg    5220
cctgtagtcc caggtacttg ggagcctgag gcaggaggat tgcttgagct caggagttca    5280
aggctgcaga gagctatgat catcccactg catttgttta aaataaatt tttaaattt      5340 gtgtgtttta tcaggggtct cctgtacagt gtatctgtgt atgtttgtgt gtgtgtttgt    5400
atacagcctt gtttaatgtt ttgagcaata agatatgcac acacaggtat tttgttgcta    5460
aagagattgg acaaggttgt agctgtgctc aggcttcagc ttggtttgtt aaattgagag    5520
ataaacaatg acaagagctg ccagccaacc acactattca aaaagcaaag tgttcaccac    5580
taaagctaac cattcatctg gttgcaggca aggctaaggc tctctctcct ctagttcctg    5640
```

-continued

```
gaacagactc acagattggc atgaagcact gatcagggc tgcactcaga ctccctggcc      5700
aagcaaacct acaccagaag agtcagtgtc acagatatga tgcggccaat ctctgtctcc      5760
aaaaacctac ctgaacttaa tggtagaatt caaagatctg gggactgagg gcacccagcc      5820
ttctaaaaca caatgtattc atgtgtttag tgtaaactct ctgcatggat tctcagtgtt      5880
aataataaaa ggaagcattc ttttacaact cctgctgtgt gcaaaagaaa gtgcaaagga      5940
tttggagtgg cattccgaag atcaccacac ataccttggt tctgatggct gctgaactcc      6000
gacttcttcg ctgagacatg actgtgggaa cagcctccag ctatctgctc atcagaggtg      6060
ctttcctcaa cctcctgcac cacctccaag agaaacagcc taaaaagaaa ccccagctgt      6120
ttacttatat tggtctgtaa atccctggaa gtaaacccca tgcatttta tctactgtct       6180 gaggacatac aataaatctg agaaagtcta tgctgtca                              6218
```

<210> SEQ ID NO 36
<211> LENGTH: 1295
<212> TYPE: DNA
<213> ORGANISM: Homo sapiens

<400> SEQUENCE: 36

```
ttggtcccag gcagcagtta gcccgccgcc cgcctgtgtg tccccagagc catggagaga       60
gccagtctga tccagaaggc caagctggca gagcaggccg aacgctatga ggacatggca      120
gccttcatga aaggcgccgt ggagaagggc gaggagctct cctgcgaaga gcgaaacctg      180
ctctcagtag cctataagaa cgtggtgggc ggccagaggg ctgcctggag ggtgctgtcc      240
agtattgagc agaaaagcaa cgaggagggc tcggaggaga aggggcccga ggtgcgtgag      300
taccgggaga aggtggagac tgagctccag ggcgtgtgcg acaccgtgct gggcctgctg      360
gacagccacc tcatcaagga ggccggggac gccgagagcc gggtcttcta cctgaagatg      420
aagggtgact actaccgcta cctggccgag gtggccaccg tgacgacaa gaagcgcatc      480 attgactcag cccggtcagc ctaccaggag gccatggaca tcagcaagaa ggagatgccg      540
cccaccaacc ccatccgcct gggcctggcc ctgaactttt ccgtcttcca ctacgagatc      600
gccaacagcc ccgaggaggc catctctctg gccaagacca ctttcgacga ggccatggct      660
gatctgcaca ccctcagcga ggactcctac aaagacagca ccctcatcat gcagctgctg      720
cgagacaacc tgacactgtg gacggccgac aacgccgggg aagagggggg cgaggctccc      780
caggagcccc agagctgagt gttgcccgcc accgccccgc cctgccccct ccagtccccc      840
accctgccga gaggactagt atggggtggg aggccccacc cttctcccct aggcgctgtt      900
cttgctccaa agggctccgt ggagagggac tggcagagct gaggccacct ggggctgggg      960
atcccactct tcttgcagct gttgagcgca cctaaccact ggtcatgccc ccaccctgc     1020 tctccgcacc cgcttcctcc cgaccccagg accaggctac ttctcccctc ctcttgcctc      1080
cctcctgccc ctgctgcctc tgatcgtagg aattgaggag tgtcccgcct gtggctgag      1140 aactggacag tggcaggggc tggagatggg tgtgtgtgtg tgtgtgtgtg tgtgtgtgtg      1200
tgtgcgcgcg cgccagtgca agaccgagat tgagggaaag catgtctgct gggtgtgacc      1260
atgtttcctc tcaataaagt tccctgtga cactc                                  1295
```

<210> SEQ ID NO 37
<211> LENGTH: 2903
<212> TYPE: DNA
<213> ORGANISM: Homo sapiens

```
<400> SEQUENCE: 37
gctgcaccgg ccccaccctc ccggcttcca gaaagctccc cttgctttcc gcggcattct      60
ttgggcgtga gtcatgcagg tttgcagcca gccccaaagg gggtgtgtgc gcgagcagag     120
cgctataaat acggcgcctc ccagtgccca caacgcggcg tcgccaggag gagcgcgcgg     180
gcacagggtg ccgctgaccg aggcgtgcaa agactccaga attggaggca tgatgaagac     240
tctgctgctg tttgtggggc tgctgctgac ctgggagagt gggcaggtcc tgggggacca     300
gacggtctca gacaatgagc tccaggaaat gtccaatcag ggaagtaagt acgtcaataa     360
ggaaattcaa aatgctgtca cgggggtgaa acagataaag actctcatag aaaaaacaaa     420
cgaagagcgc aagacactgc tcagcaacct agaagaagcc aagaagaaga agaggatgc      480
cctaaatgag accagggaat cagagacaaa gctgaaggag ctcccaggag tgtgcaatga     540
gaccatgatg gccctctggg aagagtgtaa gccctgcctg aaacagacct gcatgaagtt     600
ctacgcacgc gtctgcagaa gtggctcagg cctggttggc cgccagcttg aggagttcct     660
gaaccagagc tcgcccttct acttctggat gaatggtgac cgcatcgact ccctgctgga     720
gaacgaccgg cagcagacgc acatgctgga tgtcatgcag gaccacttca gccgcgcgtc     780
cagcatcata gacgagctct tccaggacag gttcttcacc cgggagcccc aggataccta     840
ccactacctg cccttcagcc tgccccaccg gaggcctcac ttcttctttc ccaagtcccg     900
catcgtccgc agcttgatgc cctctctcc gtacgagccc ctgaacttcc acgccatgtt     960
ccagcccttc cttgagatga tacacgaggc tcagcaggcc atggacatcc acttccatag    1020
cccggccttc cagcacccgc aacagaatt catacgagaa ggcgacgatg accggactgt    1080
gtgccgggag atccgccaca actccacggg ctgcctgcgg atgaaggacc agtgtgacaa    1140
gtgccgggag atcttgtctg tggactgttc caccaacaac ccctcccagg ctaagctgcg    1200
gcgggagctc gacgaatccc tccaggtcgc tgagaggttg accaggaaat acaacgagct    1260
gctaaagtcc taccagtgga agatgctcaa cacctcctcc ttgctggagc agctgaacga    1320
gcagtttaac tgggtgtccc ggctggcaaa cctcacgcaa ggcgaagacc agtactatct    1380
gcgggtcacc acgtggcctt cccacacttc tgactcggac gttccttccg gtgtcactga    1440
ggtggtcgtg aagctctttg actctgatcc catcactgtg acggtccctg tagaagtctc    1500
caggaagaac cctaaattta tggagaccgt ggcggagaaa gcgctgcagg aataccgcaa    1560
aaagcaccgg gaggagtgag atgtggatgt tgcttttgca cctacggggg catctgagtc    1620
cagctccccc caagatgagc tgcagccccc cagagagagc tctgcacgtc accaagtaac    1680
caggcccag cctccaggcc cccaactccg cccagcctct ccccgctctg atcctgcac    1740
tctaacactc gactctgctg ctcatgggaa gaacagaatt gctcctgcat gcaactaatt    1800
caataaaact gtcttgtgag ctgatcgctt ggagggtcct cttttttatgt tgagttgctg    1860
cttcccggca tgccttcatt ttgctatggg gggcaggcag gggggatgga aaataagtag    1920
aaacaaaaaa gcagtggcta agatggtata gggactgtca taccagtgaa gaataaaagg    1980
gtgaagaata aaagggatat gatgacaagg ttgatccact tcaagaattg cttgctttca    2040
ggaagagaga tgtgtttcaa caagccaact aaaatatatt gctgcaaatg gaagcttttc    2100
tgttctatta taaaactgtc gatgtattct gaccaaggtg cgacaatctc ctaaaggaat    2160
acactgaaag ttaaggagaa gaatcagtaa gtgtaaggtg tacttggtat tataatgcat    2220
aattgatgtt ttcgttatga aaacatttgg tgccagaag tccaaattat cagtttatt      2280
tgtaagagct attgcttttg cagcggtttt atttgtaaaa gctgttgatt tcgagttgta    2340
```

| | |
|---|---|
| agagctcagc atcccagggg catcttcttg actgtggcat ttcctgtcca ccgccggttt | 2400 |
| atatgatctt cataccttc cctggaccac aggcgtttct cggcttttag tctgaaccat | 2460 |
| agctgggctg cagtaccta cgctgccagc aggtggccat gactaccgt ggtaccaatc | 2520 |
| tcagtcttaa agctcaggct tttcgttcat taacattctc tgatagaatt ctggtcatca | 2580 |
| gatgtactgc aatggaacaa aactcatctg gctgcatccc aggtgtgtag caaagtccac | 2640 |
| atgtaaattt atagcttaga atattcttaa gtcactgtcc cttgtctctc tttgaagtta | 2700 |
| taaacaacaa acttaaagct tagcttatgt ccaaggtaag tattttagca tggctgtcaa | 2760 |
| ggaaattcag agtaaagtca gtgtgattca cttaatgata tacattaatt agaattatgg | 2820 |
| ggtcagaggt atttgcttaa gtgatcataa ttgtaaagta tatgtcacat tgtcacatta | 2880 |
| atgtcacact gtttcaaaag tta | 2903 |

<210> SEQ ID NO 38
<211> LENGTH: 1666
<212> TYPE: DNA
<213> ORGANISM: Homo sapiens

<400> SEQUENCE: 38

| | |
|---|---|
| cggcgtcgcc aggaggagcg cgcgggcaca gggtgccgct gaccgaggcg tgcaaagact | 60 |
| ccagaattgg aggcatgatg aagactctgc tgctgtttgt ggggctgctg ctgacctggg | 120 |
| agagtgggca ggtcctgggg gaccagacgg tctcagacaa tgagctccag gaaatgtcca | 180 |
| atcagggaag taagtacgtc aataaggaaa ttcaaaatgc tgtcaacggg gtgaaacaga | 240 |
| taaagactct catagaaaaa acaaacgaag agcgcaagac actgctcagc aacctagaag | 300 |
| aagccaagaa gaagaaagag gatgccctaa atgagaccag ggaatcagag acaaagctga | 360 |
| aggagctccc aggagtgtgc aatgagacca tgatggccct ctgggaagag tgtaagccct | 420 |
| gcctgaaaca gacctgcatg aagttctacg cacgcgtctg cagaagtggc tcaggcctgg | 480 |
| ttggccgcca gcttgaggag ttcctgaacc agagctcgcc cttctacttc tggatgaatg | 540 |
| gtgaccgcat cgactccctg ctggagaacg accggcagca gacgcacatg ctggatgtca | 600 |
| tgcaggacca cttcagccgc gcgtccagca tcatagacga gctcttccag gacaggttct | 660 |
| tcacccggga gccccaggat acctaccact acctgccctt cagcctgccc caccggaggc | 720 |
| ctcacttctt ctttcccaag tcccgcatcg tccgcagctt gatgcccttc tctccgtacg | 780 |
| agcccctgaa cttccacgcc atgttccagc ccttccttga tgatacac gaggctcagc | 840 |
| aggccatgga catccacttc catagcccgg ccttccagca cccgccaaca gaattcatac | 900 |
| gagaaggcga cgatgaccgg actgtgtgcc gggagatccg ccacaactcc acgggctgcc | 960 |
| tgcggatgaa ggaccagtgt gacaagtgcc gggagatctt gtctgtggac tgttccacca | 1020 |
| acaacccctc ccaggctaag ctgcggcggg agctcgacga atccctccag gtcgctgaga | 1080 |
| ggttgaccag gaaatacaac gagctgctaa agtcctacca gtggaagatg ctcaacacct | 1140 |
| cctccttgct ggagcagctg aacgagcagt ttaactgggt gtcccggctg gcaaacctca | 1200 |
| cgcaaggcga agaccagtac tatctgcggg tcaccacggt ggcttccac acttctgact | 1260 |
| cggacgttcc ttccggtgtc actgaggtgg tcgtgaagct ctttgactct gatcccatca | 1320 |
| ctgtgacggt ccctgtagaa gtctccagga gaaccctaa atttatggag accgtggcgg | 1380 |
| agaaagcgct gcaggaatac cgcaaaaagc accgggagga gtgagatgtg atgttgcttt | 1440 |
| ttgcacctac gggggcatct gagtccagct ccccccaaga tgagctgcag ccccccagag | 1500 |

-continued

```
agagctctgc acgtcaccaa gtaaccaggc cccagcctcc aggcccccaa ctccgcccag    1560
cctctccccg ctctggatcc tgcactctaa cactcgactc tgctgctcat gggaagaaca    1620
gaattgctcc tgcatgcaac taattcaata aaactgtctt gtgagc                  1666
```

<210> SEQ ID NO 39
<211> LENGTH: 2961
<212> TYPE: DNA
<213> ORGANISM: Homo sapiens

<400> SEQUENCE: 39

```
gggcagcctg ctgtcggctt agaggggatg ggcagtgtgg agggcctggc agagcaagag      60
gactcatcct tccaaaggga ctttctctgg gaagcctgct cctcgggcca ctgcgaaccc     120
tctctactct ccgaagggaa ttgtccttcc tggcttccac tacttccacc cctgaatgca     180
caggcagccc ggcccaagtc tcccactagg gatgcagatg gattcggtgt gaagggctgg     240
ctgctgttgc ctccggctct tgaaagtcaa gttcagaggc gtgcaaagac tccagaattg     300
gaggcatgat gaagactctg ctgctgtttg tggggctgct gctgacctgg gagagtgggc     360
aggtcctggg ggaccagacg gtctcagaca atgagctcca ggaaatgtcc aatcagggaa     420
gtaagtacgt caataaggaa attcaaaatg ctgtcaacgg ggtgaaacag ataaagactc     480
tcatagaaaa acaaacgaa gagcgcaaga cactgctcag caacctagaa gaagccaaga     540
agaagaaaga ggatgcccta atgagaccag ggaatcaga dacaaagctg aaggagctcc     600
caggagtgtg caatgagacc atgatggccc tctgggaaga gtgtaagccc tgcctgaaac     660
agacctgcat gaagttctac gcacgcgtct gcagaagtgg ctcaggcctg gttggccgcc     720
agcttgagga gttcctgaac cagagctcgc ccttctactt ctggatgaat ggtgaccgca     780
tcgactccct gctggagaac gaccggcagc agacgcacat gctggatgtc atgcaggacc     840
acttcagccg cgcgtccagc atcatagacg agctcttcca ggacaggttc ttcacccggg     900 agcccccagga tacctaccac tacctgccct tcagcctgcc ccaccggagg cctcacttct     960
tcttctccaa gtcccgcatc gtccgcagct tgatgccctt ctctccgtac gagcccctga    1020
acttccacgc catgttccag cccttccttg agatgataca cgaggctcag caggccatgg    1080
acatccactt ccatagcccg gccttccagc acccgccaac agaattcata cgagaaggcg    1140
acgatgaccg gactgtgtgc cgggagatcc gccacaactc cacgggctgc ctgcggatga    1200
aggaccagtg tgacaagtgc cgggagatct tgtctgtgga ctgttccacc aacaacccct    1260
cccaggctaa gctgcggcgg gagctcgacg aatccctcca ggtcgctgag aggttgacca    1320
ggaaatacaa cgagctgcta aagtcctacc agtggaagat gctcaacacc tcctccttgc    1380
tggagcagct gaacgagcag tttaactggg tgtcccggct ggcaaacctc acgcaaggcg    1440
aagaccagta ctatctgcgg gtcaccacgg tggcttccca cacttctgac tcggacgttc    1500
cttccggtgt cactgaggtg gtcgtgaagc tctttgactc tgatcccatc actgtgacgg    1560
tccctgtaga agtctccagg aagaacccta aatttatgga ccgtggcg gagaaagcgc     1620 tgcaggaata ccgcaaaaag caccgggagg agtgagatgt ggatgttgct tttgcaccta    1680
cgggggcatc tgagtccagc tcccccaag atgagctgca gccccccaga gagagctctg     1740
cacgtcacca gtaaccagg cccagcctc caggccccca actccgccca gcctctcccc     1800
gctctggatc ctgcactcta acactcgact ctgctgctca tgggaagaac agaattgctc    1860
ctgcatgcaa ctaattcaat aaaactgtct tgtgagctga tcgcttggag ggtcctcttt    1920
ttatgttgag ttgctgcttc ccggcatgcc ttcattttgc tatgggggc aggcaggggg    1980
```

-continued

```
gatggaaaat aagtagaaac aaaaaagcag tggctaagat ggtataggga ctgtcatacc    2040
agtgaagaat aaaagggtga agaataaaag ggatatgatg acaaggttga tccacttcaa    2100
gaattgcttg ctttcaggaa gagagatgtg tttcaacaag ccaactaaaa tatattgctg    2160
caaatggaag cttttctgtt ctattataaa actgtcgatg tattctgacc aaggtgcgac    2220
aatctcctaa aggaatacac tgaaagttaa ggagaagaat cagtaagtgt aaggtgtact    2280
tggtattata atgcataatt gatgttttcg ttatgaaaac atttggtgcc cagaagtcca    2340
aattatcagt tttatttgta agagctattg cttttgcagc ggtttttattt gtaaaagctg    2400 ttgatttcga gttgtaagag ctcagcatcc caggggcatc ttcttgactg tggcatttcc    2460
tgtccaccgc cggtttatat gatcttcata cctttccctg gaccacaggc gtttctcggc    2520
ttttagtctg aaccatagct gggctgcagt accctacgct gccagcaggt ggccatgact    2580
acccgtggta ccaatctcag tcttaaagct caggcttttc gttcattaac attctctgat    2640
agaattctgg tcatcagatg tactgcaatg gaacaaaact catctggctg catcccaggt    2700
gtgtagcaaa gtccacatgt aaatttatag cttagaatat tcttaagtca ctgtcccttg    2760
tctctctttg aagttataaa caacaaactt aaagcttagc ttatgtccaa ggtaagtatt    2820
ttagcatggc tgtcaaggaa attcagagta aagtcagtgt gattcactta atgatataca    2880
ttaattagaa ttatggggtc agaggtattt gcttaagtga tcataattgt aaagtatatg    2940
tcacattgtc acattaatgt c                                              2961
```

<210> SEQ ID NO 40
<211> LENGTH: 2131
<212> TYPE: DNA
<213> ORGANISM: Homo sapiens

<400> SEQUENCE: 40

```
gttcccggca ttccgtgctc cttggttccg gcgttggagc tctttggggc ccagctttgc      60
ggacccggga gctcgggacg caggcggggc ttgtgctccg cggggggcagg gcgtagggtg    120 ggcctcctac ctcccctgat ctcgcggttt gttccgtttc attggagctt cccggaccgt    180
gtgctcgacg gtgccctagg tgccgtgggg ccacacgcga gtctgataag cacccctcccc   240 cggaatcatg cggtgctgtg aggcctagcg aagatgaaga tagaatgcaa ggtagaaagt    300
gctggatacc tttagaaagc tgcaggactg gtgcgatggg agttgagacg taagaacctg    360
cccgtccgta gggctctgga tgctgctgag gcccgaggcc cctatggcag atttgaaaat    420
tcacccttgt agagtcattc ctgcctttga gcggactccc ttttaagcag atctcaagag    480
agcgttcggt ggaggccctg ggtctgcaca gctcacctcc ctgggaactg ctcgcccgag    540
cgtcggagcc ggcgctggcc ccctgcagcc ggaaggttgc agccgcagga gccccggagg    600
cccaggacac agggctcttg ctcttgcaga atccacaggt cttcttgag gaaatctgta    660 gacagaactt tgtgctgcgt ttttatctag ggaaggaaca gaaagtgtc gtctcctaga    720 aatctagcac tggagaaacg aggaaaattc ttccagcgat ggtctcccac tcagagctga    780
ggaagctttt ctactcagca gatgctgtgt gttttgatgt tgacagcacg gtcatcagag    840
aagaaggaat cgatgagcta gccaaaatct gtggcgttga ggacgcggtg tcagaaatga    900
cacggcgagc catgggcggg gcagtgcctt tcaaagctgc tctcacagag cgcttagccc    960
tcatccagcc ctccagggag caggtgcaga gactcatagc agagcaaccc ccacacctga    1020
cccccggcat aagggagctg gtaagtcgcc tacaggagcg aaatgttcag gttttcctaa    1080
```

```
tatctggtgg ctttaggagt attgtagagc atgttgcttc aaagctcaat atcccagcaa   1140
ccaatgtatt tgccaatagg ctgaaattct actttaacgg tgaatatgca ggttttgatg   1200
agacgcagcc aacagctgaa tctggtggaa aaggaaaagt gattaaactt ttaaaggaaa   1260
aatttcattt taagaaaata atcatgattg gagatggtgc cacagatatg gaagcctgtc   1320
ctcctgctga tgctttcatt ggatttggag gaaatgtgat caggcaacaa gtcaaggata   1380
acgccaaatg gtatatcact gattttgtag agctgctggg agaactggaa gaataacatc   1440
cattgtcgta cagctccaaa caacttcaga tgaatttta caagttatac agattgatac    1500
tgtttgctta cagttgccta ttacaacttg ctatagaaag ttggtacaaa tgatctgtac   1560
tttaaactac agttaggaat cctagaagat tgcttttttt ttttttttaa ctgtagttcc    1620
agtattatat gatgactatt gatttcctgg agaggttttt tttttttttg agacagaatc   1680
ttgctctgtt gcccaggctg gagtgcagtg gcgcggtctc ggctcactgc aagctctgcc   1740
tcccaggttc acgccattct cctgcctcag cctcccgagt agctgggact acaggcaccc   1800
gccaccacat ccggctaatt ttttgtattt ttagtagaga cggggtttga ccgtgttagc    1860
caggatggtc ttgatctcct gaccttgtga tccgcctgcc tcagcctccc aaagtgctgg   1920
gattacaggc ttgggccacc gcgcccagcc aatgtcctag agagttttgt gatctgaatt    1980
ctttatgtat atttgtagct atatttcata caaagtgctt taagtgtgga gagtcaatta   2040 aacacctttta ctcttagaaa tacgattcg gcagccttca gtgaatattg gtttctcttt   2100
ggtatgtcaa taaaagttta tccgtatgtc a                                   2131

<210> SEQ ID NO 41
<211> LENGTH: 2178
<212> TYPE: DNA
<213> ORGANISM: Homo sapiens

<400> SEQUENCE: 41
gttcccggca ttccgtgctc cttggttccg gcgttggagc tctttggggc ccagctttgc     60
ggacccggga gctcgggacg caggcggggc ttgtgctccg cggggcagg gcgtagggtg    120 ggcctcctac ctcccctgat ctcgcggttt gttccgtttc attggagctt cccggaccgt   180
gtgctcgacg gtgccctagg tgccgtgggg ccacacgcga gtctgataag caccctcccc   240
cggaatcatg cggtgctgtg aggcctagcg aagatgaaga tagaatgcaa ggtagaaagt   300
gctggatacc tttagaaagc tgcaggactg gtgcgatggg agttgagacg taagaacctg   360
cccgtccgta gggctctgga tgctgctgag gcccgaggcc cctatggcag atttgaaaat   420
tcacccttgt agagtcattc ctgcctttga gcggactccc ttttaagttt acagaagcac   480
ttgcagaact catcagaagc caccccgctt atcagcagat ctcaagagag cgttcggtgg   540
aggccctggg tctgcacagc tcacctccct gggaactgct cgcccgagcg tcggagccgg   600
cgctggcccc ctgcagccgg aaggttgcag ccgcaggagc cccggaggcc caggacacag   660
ggctcttgct cttgcagaat ccacaggtct ttcttgagga aatctgtaga cagaactttg   720
tgctgcgttt ttatctaggg aaggaacaga agagtgtcgt ctcctagaaa tctagcactg   780
gagaaacgag gaaaattctt ccagcgatgg tctcccactc agagctgagg aagcttttct   840
actcagcaga tgctgtgtgt tttgatgttg acagcacggt catcagagaa gaaggaatcg   900
atgagctagc caaaatctgt ggcgttgagg acgcggtgtc agaaatgaca cggcgagcca   960
tgggcggggc agtgccttc aaagctgctc tcacagagcg cttagccctc atccagccct   1020
ccagggagca ggtgcagaga ctcatagcag agcaaccccc acacctgacc cccggcataa   1080
```

```
gggagctggt aagtcgccta caggagcgaa atgttcaggt tttcctaata tctggtggct   1140
ttaggagtat tgtagagcat gttgcttcaa agctcaatat cccagcaacc aatgtatttg   1200
ccaataggct gaaattctac tttaacggtg aatatgcagg ttttgatgag acgcagccaa   1260
cagctgaatc tggtggaaaa ggaaaagtga ttaaactttt aaaggaaaaa tttcatttta   1320
agaaaataat catgattgga gatggtgcca cagatatgga agcctgtcct cctgctgatg   1380
cttTcattgg atttggagga aatgtgatca ggcaacaagt caaggataac gccaaatggt   1440
atatcactga ttttgtagag ctgctgggag aactggaaga ataacatcca ttgtcgtaca   1500
gctccaaaca acttcagatg aattTttaca agttatacag attgatactg tttgcttaca   1560
gttgcctatt acaacttgct atagaaagtt ggtacaaatg atctgtactt taaactacag   1620
ttaggaatcc tagaagattg cttttttttt tttTttaact gtagttccag tattatatga   1680
tgactattga tttcctggag aggtTtTttt tttttttgag acagaatctt gctctgttgc   1740
ccaggctgga gtgcagtggc gcggtctcgg ctcactgcaa gctctgcctc ccaggttcac   1800
gccattctcc tgcctcagcc tcccgagtag ctgggactac aggcacccgc caccacatcc   1860
ggctaatttt tgtatttttt agtagagacg gggtttgacc gtgttagcca ggatggtctt   1920
gatctcctga ccttgtgatc cgcctgcctc agcctcccaa agtgctggga ttacaggctt   1980
gggccaccgc gcccagccaa tgtcctagag agttttgtga tctgaattct ttatgtatat   2040
ttgtagctat atttcataca aagtgcttta agtgtggaga gtcaattaaa cacctttact   2100
cttagaaata cggattcggc agccttcagt gaatattggt ttctctttgg tatgtcaata   2160
aaagtttatc cgtatgtc                                                  2178
```

<210> SEQ ID NO 42
<211> LENGTH: 1442
<212> TYPE: DNA
<213> ORGANISM: Homo sapiens

<400> SEQUENCE: 42

```
ctcctacctc ccctgatctc gcggtttgtt ccgtttcatt ggagcttccc ggaccgtgtg    60
ctcgacggtg ccctaggtgc cgtggggcca cacgcgagtc tgataagcac cctcccccgg   120
aatcatgcgg tgctgtgagg cctagcgaag atgaagatag aatgcaaggt agaaagtgct   180
ggataccttt agaaagctgc aggactggtg cgatgggagt tgagacgtaa gaacctgccc   240
gtccgtaggg ctctggatgc tgctgaggcc cgaggcccct atggcagatt tgaaaattca   300
cccttgtaga gtcattcctg cctttgagcg gactcccttt taaggaggaa aattcttcca   360
gcgatggtct cccactcaga gctgaggaag cttttctact cagcagatgc tgtgtgtttt   420
gatgttgaca gcacggtcat cagagaagaa ggaatcgatg agctagccaa aatctgtggc   480
gttgaggacg cggtgtcaga aatgacacgg cgagccatgg gcgggcagt gcctttcaaa    540 gctgctctca cagagcgctt agccctcatc cagccctcca gggagcaggt gcagagactc   600
atagcagagc aaccccccaca cctgaccccc ggcataaggg agctggtaag tcgcctacag   660
gagcgaaatg ttcaggtttt cctaatatct ggtggcttta ggagtattgt agagcatgtt   720
gcttcaaagc tcaatatccc agcaaccaat gtatttgcca ataggctgaa attctacttt   780
aacggtgaat atgcaggttt tgatgagacg cagccaacag ctgaatctgg tggaaaagga   840
aaagtgatta aacttttaaa ggaaaaattt cattttaaga aaataatcat gattggagat   900
ggtgccacag atatggaagc ctgtcctcct gctgatgctt tcattggatt tggaggaaat   960
```

```
gtgatcaggc aacaagtcaa ggataacgcc aaatggtata tcactgattt tgtagagctg   1020
ctgggagaac tggaagaata acatccattg tcgtacagct ccaaacaact tcagatgaat   1080
ttttacaagt tatacagatt gatactgttt gcttacagtt gcctattaca acttgctata   1140
gaaagttggt acaaatgatc tgtactttaa actacagtta ggaatcctag aagattgctt   1200
tttttttttt tttaactgta gttccagtat tatatgatga ctattgattt cctggagagt   1260
tttgtgatct gaattcttta tgtatatttg tagctatatt tcatacaaag tgctttaagt   1320
gtggagagtc aattaaacac ctttactctt agaaatacgg attcggcagc cttcagtgaa   1380
tattggtttc tctttggtat gtcaataaaa gtttatccgt atgtcagaac ggatttgtgg   1440
aa                                                                 1442

<210> SEQ ID NO 43
<211> LENGTH: 1734
<212> TYPE: DNA
<213> ORGANISM: Homo sapiens

<400> SEQUENCE: 43
aggatggatt agagacctct attttgaggc gcactgatgt aggggctgag gaaggacatt     60
gagggcacct tcaggtctct ctgcctattc ttccttgccc caactccatt ccaggtgtac    120
atcagatcca tcaggtccga gctgtgttga ctaccactgc tttccccttc gtctcagtta    180
tgtcttggaa gaaggctttg cggatccccg gagaccttcg ggtagcaact gtcaccttga    240
tgctggcgat gctgagctcc ctactggctg agggcagaga ctctcccgag gatttcgtgt    300
tccagtttaa gggcatgtgc tacttcacca acgggacgga gcgcgtgcgt cttgtgacca    360
gatacatcta taaccgagag gagtacgcgc gcttcgacag cgacgtgggg gtgtaccgcg    420
cggtgacgcc gcaggggcgg cctgatgccg agtactggaa cagccagaag gaagtcctgg    480
aggggacccg gcggagttg gacacggtgt gcagacacaa ctacgaggtg gcgttccgcg    540 gatcttgca gaggagagtg gagcccacag tgaccatctc cccatccagg acagaggccc    600
tcaaccacca caacctgctg gtctgctcgg tgacagattt ctatccaggc cagatcaaag    660
tccggtggtt tcggaatgat caggaggaga cagccggcgt tgtgtccacc ccccttatta    720
ggaatggtga ctggactttc cagatcctgg tgatgctgga aatgactccc cagcgtggag    780
atgtctacac ctgccacgtg agcaccccca gcctccagag ccccatcacc gtggagtggc    840
gggctcagtc tgaatctgcc cagagcaaga tgctgagtgg cgttggaggc ttcgtgctgg    900
ggctgatctt ccttgggctg ggccttatca tccgtcaaag gagtcagaaa gggcttctgc    960
actgactcct gagactattt taactaggat tggttatcac tcttctgtga tgcctgctta   1020
tgcctgccca gaattcccag ctgcctgtgt cagcttgtcc ccctgagatc aaagtcctac   1080
agtggctgtc acgcagccac caggtcatct cctttcatcc ccaccccaag gcgctggctg   1140
tgactctgct tcctgcactg acccagagcc tctgcctgtg catggccagc tgcgtctact   1200
caggtcccaa ggggtttctg tttctattct ttcctcagac tgctcaagag aagcacatga   1260
aaaacattac ctgactttag agcttttta cataattaaa catgatcctg agttatctgt   1320
attctgaact ttcttaattg agaagaggca ggaaatcact gcagaatgaa ggaacatccc   1380
ttgaggtgac ccagcaaacc tgtggccaga aggaggattg taccttgaaa agacactgaa   1440
agcattttgg ggtgtgaagt aagggtgggc agaggaggta gaaaataatt caattgtcgc   1500
atcattcatg gttcttaat actgatgctc agtgcattgg ccttagaata tcccagcctc   1560
tcttctggtt tggtgagtgc tgtgtaaata agcatggtag aattgtttgg agacatatat   1620
```

```
agtgatcctt ggtcactggt gtttcaaaca ttctggaaag tcacatcgat caagaatatt      1680 tttattttt aagaaagcat aaccagcaat aaaaatacta ttttgagtc taaa              1734

<210> SEQ ID NO 44
<211> LENGTH: 1642
<212> TYPE: DNA
<213> ORGANISM: Homo sapiens

<400> SEQUENCE: 44
acaggttttt attctttctg ccaggtacat cagatccatc aggtccgagc tgtgttgact        60
accactgctt ttcccttcgt ctcagttatg tcttggaaga aggctttgcg gatccccgga       120
gaccttcggg tagcaactgt caccttgatg ctggcgatgc tgagctccct actggctgag       180
ggcagagact ctcccgagga tttcgtgttc cagtttaagg gcatgtgcta cttcaccaac       240
gggacggagc gcgtgcgtct tgtgaccaga tacatctata ccgagagga gtacgcgcgc        300 ttcgacagcg acgtgggggt gtaccgcgcg gtgacgccgc aggggcggcc tgatgccgag       360
tactggaaca gccagaagga agtcctggag gggacccggg cggagttgga cacggtgtgc       420
agacacaact acgaggtggc gttccgcggg atcttgcaga ggagagtgga gcccacagtg       480
accatctccc catccaggac agaggccctc aaccaccaca acctgctggt ctgctcggtg       540
acagatttct atccaggcca gatcaaagtc cggtggtttc ggaatgatca ggaggagaca       600
gccggcgttg tgtccacccc ccttattagg aatggtgact ggactttcca gatcctggtg       660
atgctggaaa tgactcccca gcgtggagat gtctacacct gccacgtgga gcaccccagc       720
ctccagagcc ccatcaccgt ggagtggcgg gctcagtctg aatctgccca gagcaagatg       780
ctgagtggcg ttggaggctt cgtgctgggg ctgatcttcc ttgggctggg ccttatcatc       840
cgtcaaagga gtcagaaagg gcttctgcac tgactcctga ctattttta actaggattg       900 gttatcactc ttctgtgatg cctgcttatg cctgcccaga attcccagct gcctgtgtca       960
gcttgtcccc ctgagatcaa agtcctacag tggctgtcac gcagccacca ggtcatctcc      1020
tttcatcccc accccaaggc gctggctgtg actctgcttc ctgcactgac ccagagcctc      1080
tgcctgtgca tggccagctg cgtctactca ggtcccaagg ggtttctgtt tctattcttt      1140
cctcagactg ctcaagagaa gcacatgaaa acattacct gactttagag cttttttaca      1200
taattaaaca tgatcctgag ttatctgtat tctgaacttt cttaattgag aagaggcagg      1260
aaatcactgc agaatgaagg aacatcccttt gaggtgaccc agcaaacctg tggccagaag      1320
gaggattgta ccttgaaaag acactgaaag cattttgggg tgtgaagtaa gggtgggcag      1380
aggaggtaga aaataattca attgtcgcat cattcatggt tctttaatac tgatgctcag      1440
tgcattggcc ttagaatatc ccagcctctc ttctggtttg gtgagtgctg tgtaaataag      1500
catggtagaa ttgtttggag acatatatag tgatccttgg tcactggtgt ttcaaacatt      1560
ctggaaagtc acatcgatca agaatatttt ttatttttaa gaaagcataa ccagcaataa      1620
aaatactatt tttgagtcta aa                                                1642
```